(12) United States Patent
Neubert et al.

(10) Patent No.: US 7,074,742 B2
(45) Date of Patent: Jul. 11, 2006

(54) PYRIDINYL AMIDES AND IMIDES FOR USE AS FUNGICIDES

(75) Inventors: Timothy Donald Neubert, New Castle, DE (US); David Walter Piotrowski, Portage, MI (US); Michael Paul Walker, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 389 days.

(21) Appl. No.: 10/380,243

(22) PCT Filed: Sep. 17, 2001

(86) PCT No.: PCT/US01/28971

§ 371 (c)(1),
(2), (4) Date: Mar. 12, 2003

(87) PCT Pub. No.: WO02/22583

PCT Pub. Date: Mar. 21, 2002

(65) Prior Publication Data

US 2004/0044040 A1 Mar. 4, 2004

Related U.S. Application Data

(60) Provisional application No. 60/277,199, filed on Mar. 20, 2001, and provisional application No. 60/233,374, filed on Sep. 18, 2000.

(51) Int. Cl.
| | |
|---|---|
| A01N 43/40 | (2006.01) |
| A61K 31/41 | (2006.01) |
| C07D 213/62 | (2006.01) |
| C07D 213/44 | (2006.01) |
| C07D 213/181 | (2006.01) |

(52) U.S. Cl. .............. 504/130; 514/333; 514/335; 546/261; 546/262; 546/264; 546/265

(58) Field of Classification Search ............ 504/130; 514/333, 335; 546/261, 262, 264, 265
See application file for complete search history.

(56) References Cited

U.S. PATENT DOCUMENTS

| 4,006,239 A | | 2/1977 | Mayer et al. | |
|---|---|---|---|---|
| 4,966,908 A | | 10/1990 | Eckhardt et al. | |
| 5,126,358 A | * | 6/1992 | Kunz ............... | 514/333 |
| 5,506,192 A | * | 4/1996 | Anderson et al. ........ | 504/243 |
| 5,561,101 A | * | 10/1996 | Anderson et al. ........ | 504/242 |
| 5,627,137 A | * | 5/1997 | Anderson et al. ........ | 504/243 |
| 5,627,138 A | * | 5/1997 | Anderson et al. ........ | 504/243 |
| 5,852,042 A | | 12/1998 | Jakobi et al. | |
| 6,630,495 B1 | | 10/2003 | Cooke et al. | |

FOREIGN PATENT DOCUMENTS

| EP | 0 642 502 | 7/2000 |
|---|---|---|
| JP | 04124107 | 4/1992 |
| JP | 05230016 | 9/1993 |
| JP | 7 10841 | 1/1995 |
| JP | 7 25853 | 1/1995 |
| JP | 08208615 | 8/1996 |
| WO | WO 9610016 | 4/1996 |
| WO | WO 9942447 A | 8/1999 |
| WO | WO 0105769 | 1/2001 |
| WO | WO 0111965 A1 | 2/2001 |
| WO | WO 0111966 A | 2/2001 |
| WO | WO 0112604 A1 | 2/2001 |
| WO | WO 0157036 A | 8/2001 |

OTHER PUBLICATIONS

SCI Finder printouts re JP 04124107 (4 pages) and Compound Registry No. 132222–47–0 (3 pages) (2003).
Patent Abstracts of Japan, vol. 1995 No. 4 May 31, 1995 re JP 07 025853A (Ishihara Sangyo Kaisha Ltd), Jan. 27, 1995.
Patent Abstracts of Japan, vol. 017, No. 689 (C–1143) Dec. 16, 1993 re JP05 230016A (Takeda Chem Ind Ltd) Sep. 7, 1993.
Patent Abstracts of Japan, vol. 1996 No. 12, Dec. 26, 1996 re JP08 208615A (Dainippon Ink & AMP; Chem Inc), Aug. 13, 1996.
Patent Abstracts of Japan, vol. 016, No. 383 (C–0974) Aug. 17, 1992 re JP 04 124107A (Nippon Kayaku Co Ltd).

* cited by examiner

Primary Examiner—Cecilia J. Tsang
Assistant Examiner—Raymond Covington

(57) ABSTRACT

Compounds of Formula (I), their N-oxides and agriculturally suitable salts are disclosed which are useful as fungicides formula (I), (II) wherein A is a substituted pyridinyl ring; B is a substituted pyridinyl ring; W is C=L or $SO_n$ is O or S; $R^1$ and $R^2$ are each independently H; or $C_1$–$C_6$ alkyl, $C_2$–$C_6$ alkenyl, $C_2$–$C_6$ alkynyl or $C_3$–$C_6$ cycloalkyl, each optionally substituted; $R^3$ is H; or $C_1$–$C_6$ alkyl, $C_2$–$C_6$ alkenyl, $C_2$–$C_6$ alkynyl or $C_3$–$C_6$ cycloalkyl, $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl; $R^4$ is C1–C6 alkyl, $C_2$–$C_6$ alkenyl, $C_2$–$C_6$ alkynyl or $C_3$–$C_6$ cycloalkyl, each optionally substituted; X is O or S; and n is 1 or 2; provided that when W is C=O and $R^1$, $R^2$ and $R^3$ are H; then B is other than 4-trifluoromethyl-3-pyridinyl, 2-chloro-4-pyridinyl and 2,6-dihalo-4-pyridinyl. Also disclosed are compositions containing the compounds of Formula (I) and a method for controlling plant diseases caused by fungal plant pathogens that involves applying an effective amount of a compound of Formula (I)

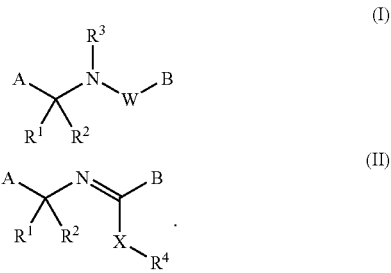

20 Claims, No Drawings

PYRIDINYL AMIDES AND IMIDES FOR USE AS FUNGICIDES

This application represents a national filing under 35 USC 371 of International Application No. PCT/US01/28971 filed Sep. 17, 2001 claiming priority of U.S. Provisional Application No. 60/277,199 filed Mar. 20, 2001 and U.S. Provisional Application No. 60/233,374 filed Sep. 18, 2000.

BACKGROUND OF THE INVENTION

This invention relates to certain pyridinyl amides and imides, their N-oxides, agriculturally suitable salts and compositions, and methods of their use as fungicides.

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds, which are more effective, less costly, less toxic, environmentally safer or have different modes of action.

WO 99/42447 discloses certain benzamides of formula i as fungicides

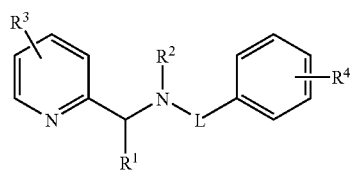

i wherein, among others,
 $R^1$ is H, alkyl or acyl;
 $R^2$ is H or alkyl; and
 L is —(C=O)—, —SO$_2$— or —(C=S)—.

SUMMARY OF THE INVENTION

This invention pertains to compounds of Formula I or Formula II including all geometric and stereoisomers, N-oxides, and agriculturally suitable salts thereof:

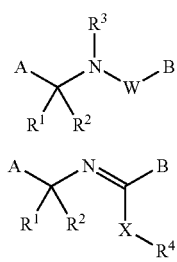

wherein
 A is a substituted pyridinyl ring;
 B is a substituted pyridinyl ring;
 W is C=L or SO$_n$;
 L is O or S;
 $R^1$ and $R^2$ are each independently H; or C$_1$–C$_6$ alkyl, C$_2$–C$_6$ alkenyl, C$_2$–C$_6$ alkynyl or C$_3$–C$_6$ cycloalkyl, each optionally substituted;
 $R^3$ is H; or C$_1$–C$_6$ alkyl, C$_2$–C$_6$ alkenyl, C$_2$–C$_6$ alkynyl or C$_3$–C$_6$ cycloalkyl, C$_2$–C$_6$ alkylcarbonyl, C$_2$–C$_6$ alkoxycarbonyl, C$_2$–C$_6$ alkylaminocarbonyl or C$_3$–C$_8$ dialkylaminocarbonyl;
 $R^4$ is C$_1$–C$_6$ alkyl, C$_2$–C$_6$ alkenyl, C$_2$–C$_6$ alkynyl or C$_3$–C$_6$ cycloalkyl, each optionally substituted;
 X is O or S; and
 n is 1 or 2; provided that when W is C=O and $R^1$, $R^2$ and $R^3$ are H; then B is other than 4-trifluoromethyl-3-pyridinyl, 2-chloro-4-pyridinyl and 2,6-dihalo-4-pyridinyl.

This invention also relates to fungicidal compositions comprising fungicidally effective amounts of the compounds of the invention and at least one additional component selected from the group consisting of surfactants, solid diluents or liquid diluents and/or at least one other fungicide having a different mode of action.

This invention also relates to a method for controlling plant diseases caused by fungal plant pathogens comprising applying to the plant or portion thereof, or to the plant seed or seedling, a fungicidally effective amount of the compounds of the invention (e.g., as a composition described herein).

DETAILS OF THE INVENTION

As noted above, A and B are each independently a substituted pyridinyl ring. The term "substituted" in connection with these A or B groups refers to groups that have at least one non-hydrogen substituent that does not extinguish the fungicidal activity. Examples of Formula I and Formula II incorporating said pyridinyl rings in which A is substituted with 1 to 4 $R^5$, B is substituted with 1 to 4 $R^6$ include the rings illustrated in Exhibit 1 wherein m and p are independently integers from 1 to 4. Note that the attachment point between $(R^5)_m$ and A and $(R^6)_p$ and B is illustrated as floating, and $(R^5)_m$ and $(R^6)_p$ can be attached to any available carbon atom of the pyridinyl rings.

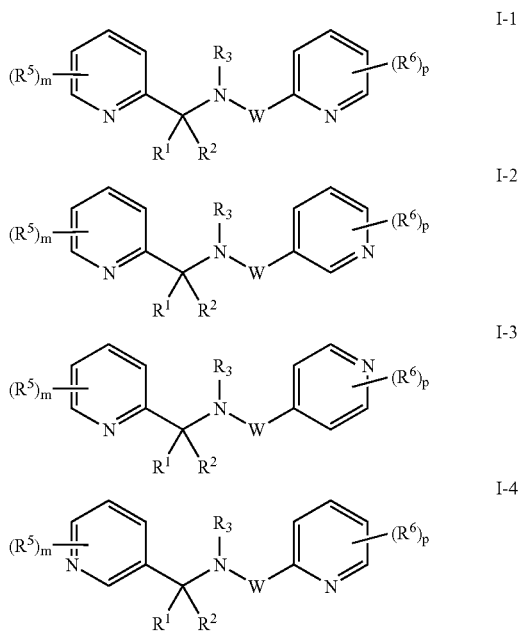

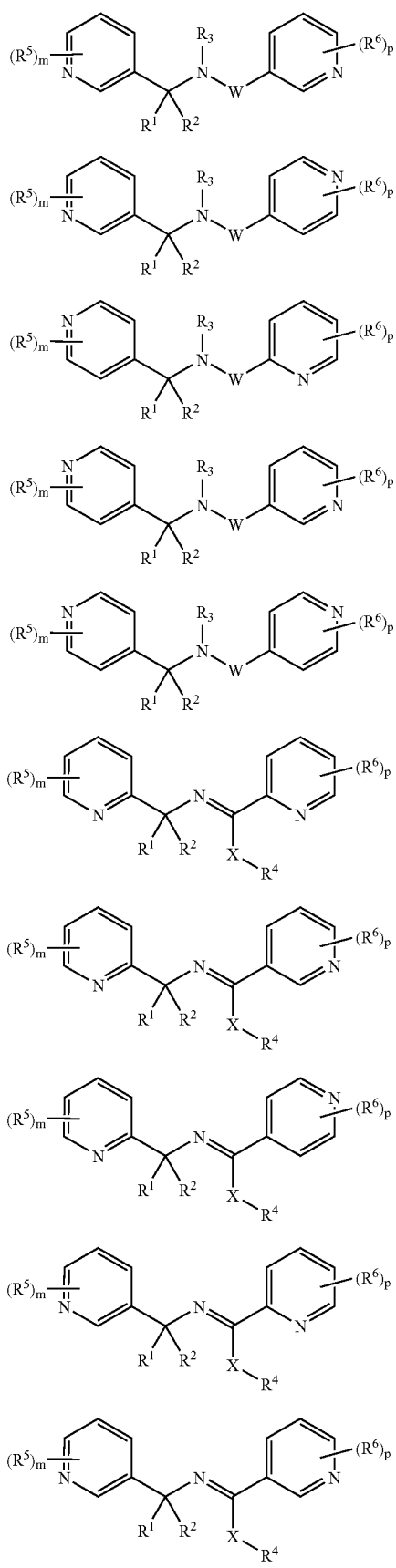
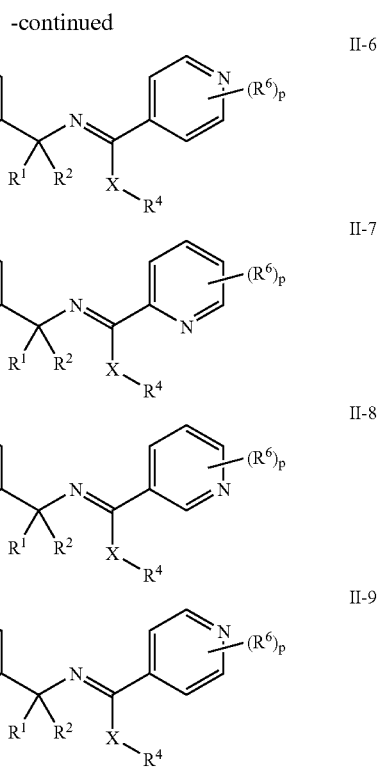

Examples of $R^5$ when attached to A and $R^6$ when attached to B include:

$R^5$ and $R^6$ are each independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or $R^5$ and $R^6$ are each independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl $C_1$–$C_4$ alkoxycarbonyl, $C_1$–$C_4$ alkylamino, $C_2$–$C_8$ dialkylamino, $C_3$–$C_6$ cycloalkylamino, $C_3$–$C_6$ (alkyl) cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

Other $R^5$ and $R^6$ groups will be evident to one of ordinary skill. For example, each $R^5$ and/or $R^6$ can be $NH_2$, NHCO($C_1$–$C_4$ alkyl) or NHCO($C_1$–$C_4$ haloalkyl); or each $R^5$ and/or $R^6$ can be phenyl, benzyl or phenoxy, each substituted with $C_5$–$C_8$ trialklylsilylalkynyl.

Of note are compounds of Formula I wherein $R^5$ and $R^6$ are each independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, NO$_2$, hydroxy, C$_1$–C$_4$ alkoxy, C$_1$–C$_4$ haloalkoxy, C$_1$–C$_4$ alkylthio, C$_1$–C$_4$ alkylsulfinyl, C$_1$–C$_4$ alkylsulfonyl, C$_1$–C$_4$ haloalkylthio, C$_1$–C$_4$ haloalkylsulfinyl, C$_1$–C$_4$ haloalkylsulfonyl, C$_1$–C$_4$ alkoxycarbonyl, C$_1$–C$_4$ alkylamino, C$_2$–C$_8$ dialkylamino, C$_3$–C$_6$ cycloalkylamino, C$_2$–C$_6$ alkylcarbonyl, C$_2$–C$_6$ alkoxycarbonyl, C$_2$–C$_6$ alkylaminocarbonyl, C$_3$–C$_8$ dialkylaminocarbonyl, C$_3$–C$_6$ trialkylsilyl; or R$^5$ and R$^6$ are each independently phenyl, benzyl or phenoxy, each optionally substituted with C$_1$–C$_4$ alkyl, C$_2$–C$_4$ alkenyl, C$_2$–C$_4$ alkynyl, C$_3$–C$_6$ cycloalkyl, C$_1$–C$_4$ haloalkyl, C$_2$–C$_4$ haloalkenyl, C$_2$–C$_4$ haloalkynyl, C$_3$–C$_6$ halocycloalkyl, halogen, CN, NO$_2$, C$_1$–C$_4$ alkoxy, C$_1$–C$_4$ haloalkoxy, C$_1$–C$_4$ alkylthio, C$_1$–C$_4$ alkylsulfinyl, C$_1$–C$_4$ alkylsulfonyl C$_1$–C$_4$ alkoxycarbonyl, C$_1$–C$_4$ alkylamino, C$_2$–C$_8$ dialkylamino, C$_3$–C$_6$ cycloalkylamino, C$_3$–C$_6$ (alkyl) cycloalkylamino, C$_2$–C$_4$ alkylcarbonyl, C$_2$–C$_6$ alkoxycarbonyl, C$_2$–C$_6$ alkylaminocarbonyl, C$_3$–C$_8$ dialkylaminocarbonyl, C$_5$–C$_8$ trialklylsilylalkynyl or C$_3$–C$_6$ trialkylsilyl.

As noted above, R$^1$ and R$^2$ are each independently H; or C$_1$–C$_6$ alkyl, C$_2$–C$_6$ alkenyl, C$_2$–C$_6$ alkynyl or C$_3$–C$_6$ cycloalkyl, each optionally substituted; and R4 is C$_1$–C$_6$ alkyl, C$_2$–C$_6$ alkenyl, C$_2$–C$_6$ alkynyl or C$_3$–C$_6$ cycloalkyl, each optionally substituted. The term "optionally substituted" in connection with these R$^1$, R$^2$ and R$^4$ groups refers to groups which are unsubstituted or have at least one non-hydrogen substituent that does not extinguish the fungicidal activity possessed by the unsubstituted analog. Examples of optionally substituted R$^1$, R$^2$ and R$^4$ groups are those that are optionally substituted with one or more substituents selected from the group consisting of halogen, CN, NO$_2$, hydroxy, C$_1$–C$_4$ alkoxy, C$_1$–C$_4$ alkylthio, C$_1$–C$_4$ alkylsulfinyl, C$_1$–C$_4$ alkylsulfonyl, C$_2$–C$_4$ alkoxycarbonyl, C$_1$–C$_4$ alkylamino, C$_2$–C$_8$ dialkylamino and C$_3$–C$_6$ cycloalkylamino. Although these substituents are listed in the examples above, it is noted that they do not need to be present since they are optional substituents.

Examples of N-oxides of Formula I or Formula II are illustrated as I-10 through I-16 and as II-10 through II-16, respectively, in Exhibit 2, wherein R$^1$, R$^2$, R$^3$, R$^4$, R$^5$, R$^6$, W, X, m and p are as defined above.

Exhibit 2

I-10
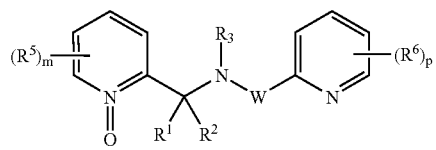

I-11
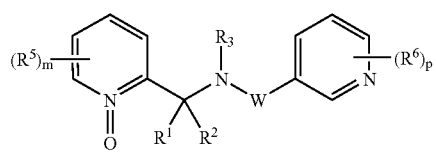

I-12
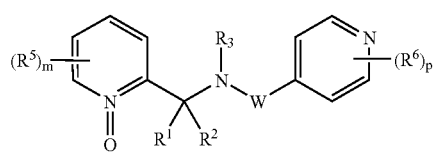

I-13
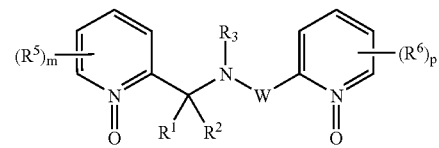

I-14
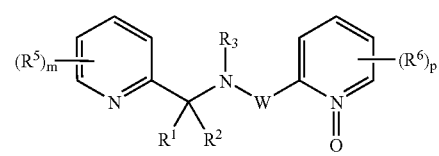

I-15
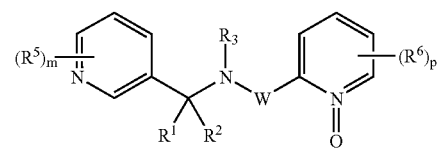

I-16
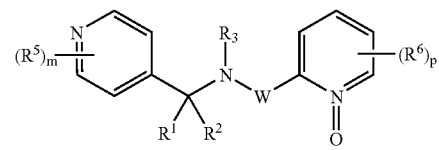

II-10
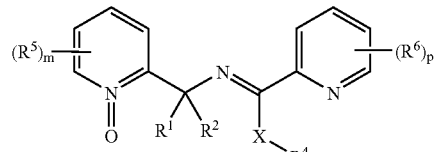

II-11
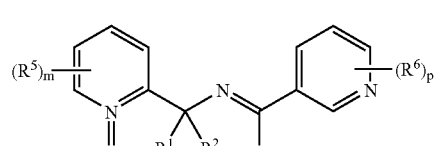

II-12
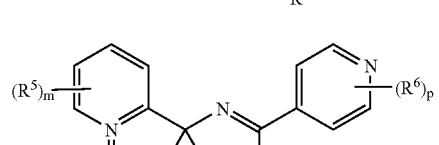

II-13
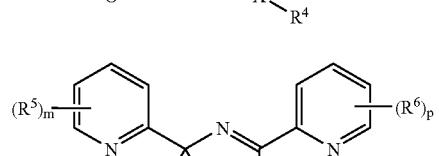

II-14
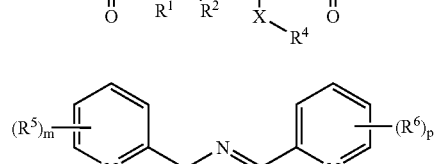

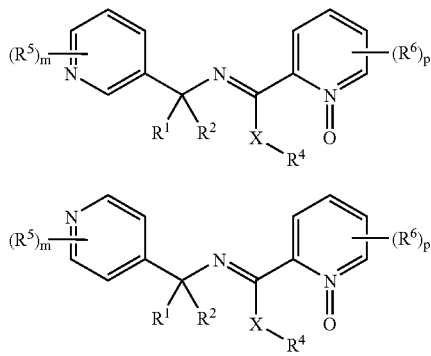

II-15

II-16

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1-2 alkyl" indicates that one or two of the available positions for that substituent may be alkyl which are independently selected. "Alkenyl" includes straight chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. The term "Alkenyloxy" includes straight chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylthioalkoxy" denotes alkylthio substitution on alkoxy. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Cyanoalkyl" denotes an alkyl group substituted with one cyano group. Examples of "cyanoalkyl" include $NCCH_2$, $NCCH_2CH_2$ and $CH_3CH(CN)CH_2$. "Alkylamino", "dialkylamino", "alkenylthio", "alkenylsulfinyl", "alkenylsulfonyl", "alkynylthio", "alkynylsulfinyl", "alkynylsulfonyl", and the like, are defined analogously to the above examples. "Cycloalkyl" includes, for example, cyclopropyl, cyclobutyl, cyclopentyl, and cyclohexyl. The term "cycloalkoxy" includes the same groups linked through an oxygen atom such as cyclopentyloxy and cyclohexyloxy.

The term "halogen", either alone or in compound words such as "haloalkyl", includes fluorine, chlorine, bromine or iodine. The term "1-2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", "haloalkylthio", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$. Examples of "haloalkoxyalkoxy" include $CF_3OCH_2O$, $ClCH_2CH_2OCH_2CH_2O$, $Cl_3CCH_2OCH_2O$ as well as branched alkyl derivatives. Examples of "alkylcarbonyl" include $C(O)CH_3$, $C(O)CH_2CH_2CH_3$ and $C(O)CH(CH_3)_2$. Examples of "alkoxycarbonyl" include $CH_3C(=O)$, $CH_3CH_2C(=O)$, $CH_3CH_2CH_2C(=O)$, $(CH_3)_2CHOC(=O)$ and the different butoxy- or pentoxycarbonyl isomers.

One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748–750, S. V. Ley, Ed., Pergamon Press; M. Tisler and B. Stanovnik in *Comprehensive Heterocyclic Chemistry*, vol. 3, pp 18–20, A. J. Boulton and A. McKillop, Eds., Pergamon Press; M. R. Grimmett and B. R. T. Keene in *Advances in Heterocyclic Chemistry*, vol. 43, pp 149–161, A. R. Katritzky, Ed., Academic Press; M. Tisler and B. Stanovnik in *Advances in Heterocyclic Chemistry*, vol. 9, pp 285–291, A. R. Katritzky and A. J. Boulton, Eds., Academic Press; and G. W. H. Cheeseman and E. S. G. Werstiuk in *Advances in Heterocyclic Chemistry*, vol. 22, pp 390–392, A. R. Katritzky and A. J. Boulton, Eds., Academic Press.

The total number of carbon atoms in a substituent group is indicated by the "$C_i$–$C_j$" prefix where i and j are numbers from 1 to 8. For example, $C_1$–$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including CH₃CH₂CH₂OCH₂ and CH₃CH₂OCH₂CH₂.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

When a group contains a substituent which can be hydrogen, for example $R^1$ or $R^2$ then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form. In particular, when $R^1$ and $R^2$ of Formula I and Formula II are different, then said formulas possess a chiral center at the carbon to which they are commonly bonded. This invention comprises racemic mixtures. In addition, this invention includes compounds that are enriched compared to the racemic mixture in an enantiomer of the formulas

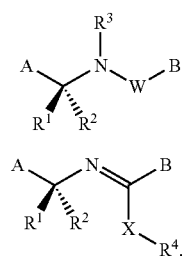

I'

II'

Included are the essentially pure enantiomers of Formula I' and Formula II'. This invention also includes compounds that are enriched compared to the racemic mixture in an enantiomer of the formulas

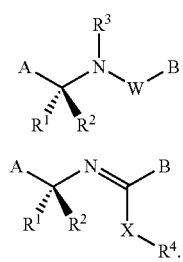

I"

II"

Included are the essentially pure enantiomers of Formula I" and Formula II".

When enantiomerically enriched, one enantiomer is present in greater amounts that the other and the extent of enrichment can be defined by an expression of enantiomer excess("ee"), which is defined as 100 (2x−1) where x is the mole fraction of the dominant enantiomer in the mixture. (e.g., an ee of 20% corresponds to a 60:40 ratio of enantiomers).

The more active enantiomer with respect to the relative positions of $R^1$, $R^2$, A and the rest of the molecule bonded through nitrogen corresponds to the configuration of the enantiomer of 2,4-dichloro-N-[(1R)-1-[3-chloro-5-(trifluoromethyl)-2-pyridinyl]ethyl]-3-pyridinecarboxamide that, when in a solution of CDCl₃, rotates plane polarized light in the (+) or dextro direction (i.e. the predominant enantiomer of Compound 31 of Index Table B).

Preferably the compositions of this invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula II can also exist as (E)- or (Z)-isomers, or as a mixture of E)- and (Z)-isomers with respect to the C═N bond shown in the structure. This invention comprises mixtures of geometric isomers as well as the individual isomers.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol.

Preferred compounds for reasons of better activity and/or ease of synthesis are:

Preferred 1. Preferred are compounds of Formula I or Formula II wherein

A is a pyridinyl ring substituted with from 1 to 4 $R^5$;

B is a pyridinyl ring substituted with from 1 to 4 $R^6$;

$R^1$ and $R^2$ are each independently H; or $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, NO₂, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino;

$R^4$ is $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, NO₂, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; and $R^5$ and $R^6$ are each independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, CO₂H, CONH₂, NO₂, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or $R^5$ and $R^6$ are each independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl $C_1$–$C_4$ alkoxycarbonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

Of note are compounds of Preferred 1 wherein each $R^5$ is independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; provided that when A is 2-pyridinyl, then $R^5$ is other than $C_1$ to $C_6$ haloalkyl; and each $R^6$ is independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or $R^5$ and $R^6$ are each independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl $C_1$–$C_4$ alkoxycarbonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

Preferred 2. Compounds of Preferred 1 of Formula I wherein W is C=O.

Of note are compounds of Preferred 2 wherein A is a substituted 3-pyridinyl ring. Also of note are compounds of Preferred 2 wherein each $R^5$ is independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; provided that when A is 2-pyridinyl, then $R^5$ is other than $C_1$ to $C_6$ haloalkyl.

Preferred 3. Compounds of Preferred 2 wherein

A is a 2-pyridinyl ring substituted with from 1 to 4 $R^5$; and

B is substituted with from 1 to 4 $R^6$, with at least one $R^6$ located in a position ortho to the link with W.

Of note are compounds of Preferred 3 wherein $R^5$ is Cl, Br, $CH_3$, $OCF_3$, $OCHF_2$, $OCH_2CF_3$, $OCF_2CF_3$, $OCF_2CF_2H$, $OCHFCF_3$, $SCF_3$, $SCHF_2$, $SCH_2CF_3$, $SCF_2CF_3$, $SCF_2CF_2H$, $SCHFCF_3$, $SOCF_3$, $SOCHF_2$, $SOCH_2CF_3$, $SOCF_2CF_3$, $SOCF_2CF_2H$, $SOCHFCF_3$, $SO_2CF_3$, $SO_2CHF_2$, $SO_2CH_2CF_3$, $SO_2CF_2CF_3$, $SO_2CF_2CF_2H$ or $SO_2CHFCF_3$. Also of note are compounds of Preferred 3 wherein B is either a 3-pyridinyl or 4-pyridinyl ring having an $R^6$ at each position ortho to the link with W (and optionally 1 to 2 additional $R^6$).

Preferred 4. Compounds of Preferred 3 wherein B is either a 3-pyridinyl or 4-pyridinyl ring having an $R^6$ at each position ortho to the link with W, and optionally 1 to 2 additional $R^6$ and $R^6$ is either halogen or methyl.

Preferred 5. Compounds of Preferred 4 wherein B is a 3-pyridinyl ring wherein one $R^6$ is Cl and is located at the 2-position ortho to the link with W, another $R^6$ is selected from Cl or methyl and is located at the 4-position ortho to the link with W and a third optional $R^6$ is methyl at the 6-position.

Preferred 6. Compounds of Preferred 5 wherein A is 3-chloro-5-$CF_3$-2-pyridinyl.

Preferred 7. Compounds of Preferred 3, but especially Preferred 4, wherein $R^1$ is H and $R^2$ is $CH_3$.

Preferred 8. Compounds of Preferred 1 of Formula II wherein

A is a 2-pyridinyl ring substituted with from 1 to 4 $R^5$; and

B is substituted with from 1 to 4 $R^6$, with at least one $R^6$ located in a position ortho to the link with the carbon that is bonded to both X and B.

Preferred 9. Compounds of Preferred 5 wherein X is S.

Preferred compounds of this invention include those of Preferred 1 through Preferred 9 wherein $R^1$ is H or $CH_3$, $R^2$ is H and (in Formula I) $R^3$ is H.

Specifically preferred are the compounds selected from the group consisting of 2,4-Dichloro-N-[[3-chloro-5-(trifluoromethyl)-2-pyridinyl]methyl]-3-pyridinecarboxamide, 2,4-Dichloro-N-[1-[3-chloro-5-(trifluoromethyl)-2-pyridinyl]ethyl]-3-pyridinecarboxamide, 2,4-Dichloro-N-[[3-chloro-5-(trifluoromethyl)-2-pyridinyl]methyl]-6-methyl-3-pyridinecarboxamide, and 2,4-Dichloro-N-[1-[3-chloro-5-(trifluoromethyl)-2-pyridinyl]ethyl]-6-methyl-3-pyridinecarboxamide.

Also specifically preferred are the compounds selected from the group consisting of 2,4-Dichloro-N-[(3,5-dichloro-2-pyridinyl)methyl]-3-pyridinecarboxamide, 2,4-Dichloro-N-[1-(3,5-dichloro-2-pyridinyl)ethyl]-3-pyridinecarboxamide, 2,4-Dichloro-N-[(3,5-dichloro-2-pyridinyl)methyl]-6-methyl-3-pyridinecarboxamide, 2,4-Dichloro-N-[1-(3,5-dichloro-2-pyridinyl)ethyl]-6-methyl-3-pyridinecarboxamide, N-[(5-bromo-3-chloro-2-pyridinyl)methyl]-2,4-dichloro-3-pyridinecarboxamide, N-[1-(5-bromo-3-chloro-2-pyridinyl)ethyl]-2,4-dichloro-3-pyridinecarboxamide, N-[(5-bromo-3-chloro-2-pyridinyl)methyl]-2,4-dichloro-6-methyl-3-pyridinecarboxamide, and N-[1-(5-bromo-3-chloro-2-pyridinyl)ethyl]-2,4-dichloro-6-methyl-3-pyridinecarboxamide.

This invention also relates to fungicidal compositions comprising fungicidally effective amounts of the compounds of the invention and at least one additional component selected from the group consisting of surfactants, solid diluents or liquid diluents. The preferred compositions of the present invention are those which comprise the above preferred compounds.

This invention also relates to a method for controlling plant diseases caused by fungal plant pathogens comprising applying to the plant or portion thereof, or to the plant seed or seedling, a fungicidally effective amount of the compounds of the invention (e.g., as a composition described herein). The preferred methods of use are those involving the above-preferred compounds.

The compounds of Formula I and Formula II can be prepared by one or more of the following methods and variations as described in Schemes 1–6. The definitions of A, B, L, W, $R^1$ through $R^6$, X and n in the compounds of Formulas 1–4 below are as defined above. Compounds of Formula 1a, 1b and 1c are subsets of Formula 1. Compounds of Formulae Ia, Ib and Ic are subsets of the compounds of Formula I, and all substituents for Formulae Ia, Ib and Ic are as defined above for Formula I. Compounds of Formula IIa are a subset of the compounds of Formula II, and all substituents for Formula IIa are as defined above for Formula II.

The compounds of Formula I can be prepared as described below in Schemes 1–5. The compounds of Formula Ic and IIa can be prepared as described below in Scheme 6.

The compounds of Formula Ia are prepared by treating amine salts of Formula 1 with an appropriate acid chloride in an inert solvent with two molar equivalents of a base (e.g. triethylamine or potassium carbonate) present. Suitable solvents are selected from the group consisting of ethers such as tetrahydrofuran, dimethoxyethane, or diethyl ether; hydrocarbons such as toluene or benzene; and halocarbons such as dichloromethane or chloroform.

Scheme 1

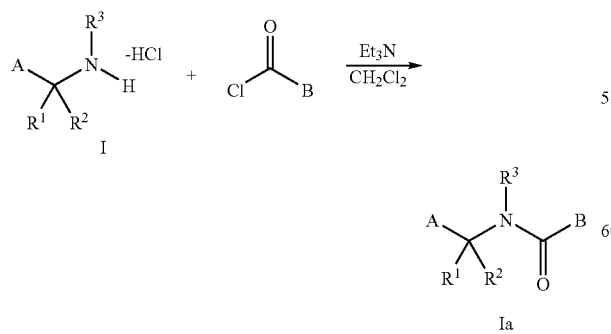

Alternatively, compounds of Formula Ia can be synthesized by reacting the amine salts of Formula 1 with an appropriate carboxylic acid in the presence of an organic dehydrating reagent such as 1,3-dicyclohexylcarbodiimide (DCC) or 1-[3-(Dimethylamino)propyl]-3-ethylcarbodiimide hydrochloride (EDC) as depicted in Scheme 2. Suitable solvents are selected from the group consisting of ethers such as tetrahydrofuran, dimethoxyethane, or diethyl ether; hydrocarbons such as toluene or benzene; and halocarbons such as dichloromethane or chloroform.

Scheme 2

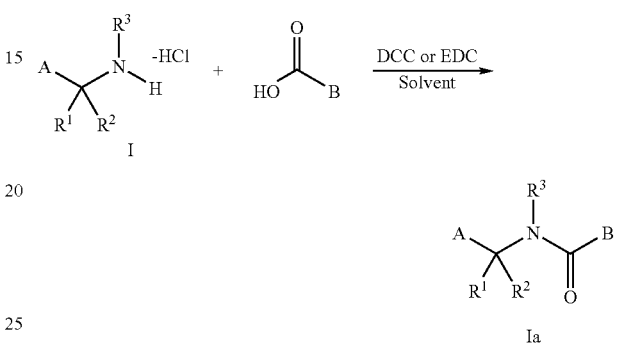

Intermediate salt 1a, wherein A is 2-pyridyl bearing the indicated substituents and $R^1$, $R^2$, and $R^3$ are hydrogen, can be prepared by reacting the commercially available imine ester 5 shown in Scheme 3 with a 2,3-dichloro-pyridine substituted with $R^5$ (of Formula 4) in the presence of a strong base such as sodium hydride in a polar, aprotic solvent such as N,N-dimethylformamide followed by heating in acidic medium in a procedure analogous to those found in WO99/42447. Compounds of Formula 1b can be prepared by similar procedures in which the intermediate anion resulting from step 1 is treated with an alkylating agent such as methyl iodide prior to heating in an acidic medium. Of note are compounds wherein $R^5$ is $CF_3$.

Scheme 3

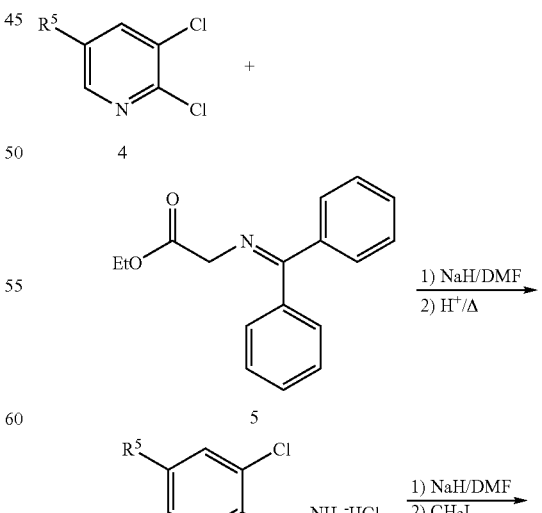

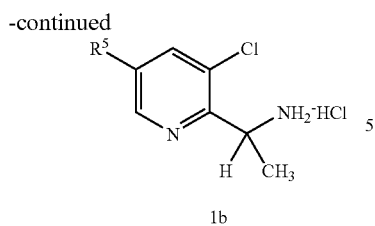

1b

Compounds of Formula 1c (wherein A is a substituted pyridinyl ring), bearing an aminomethyl group, can be synthesized from nitriles of Formula 2 (wherein A is a substituted pyridinyl ring) by reduction of the nitrile using lithium aluminum hydride in toluene to give the corresponding aminomethyl intermediates (Scheme 4).

Scheme 4

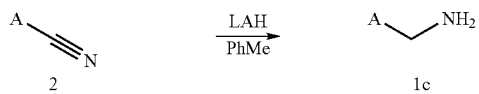

A is a substituted pyridinyl ring

Alternatively, compounds of Formula 1c (compounds in which A is as defined above and $R^1$ and $R^2$ are hydrogen) can be synthesized by reacting compounds of Formula 3 with ammonia in a protic solvent such as methanol to provide compounds of Formula 1c. Compounds of Formula 1c can also be prepared by reacting compounds of Formula 3 with a potassium salt of phthalimide followed by reaction with either aminoethanol or hydrazine in an alcohol solvent to provide the desired aminomethyl intermediates, Formula 1c (Scheme 5).

Scheme 5

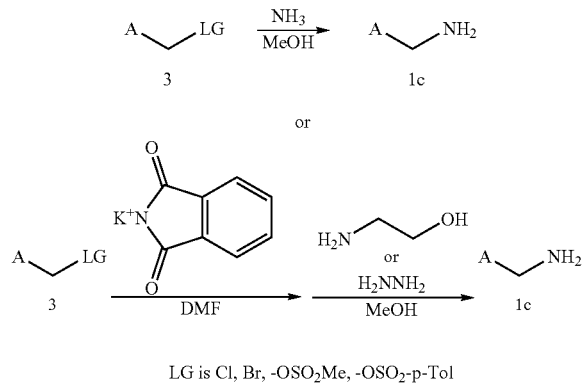

LG is Cl, Br, -OSO$_2$Me, -OSO$_2$-p-Tol

Compounds of Formula IIa (compounds in which $R^1$, $R^2$, A and B are as defined above and X is S) can be synthesized as outlined in Scheme 6. Amides of Formula Ib (compounds of Formula I in which $R^3$ is H) shown below can be converted to thioamides of Formula Ic by contacting the amide with Lawesson's reagent or phosphorus pentasulfide in an appropriate solvent (for references, see March; *J. Advanced Organic Chemistry*, 4$^{th}$ ed., pp. 893–4). The thioamide can then be alkylated using an appropriate alkylating reagent in the presence of a base such as potassium carbonate, sodium hydride or potassium hydroxide. Suitable solvents can include, but are not limited to, ethers such as tetrahydrofuran, dimethoxyethane, or diethyl ether; hydro carbons such as toluene or benzene; and halocarbons such as dichloromethane or chloroform.

Scheme 6

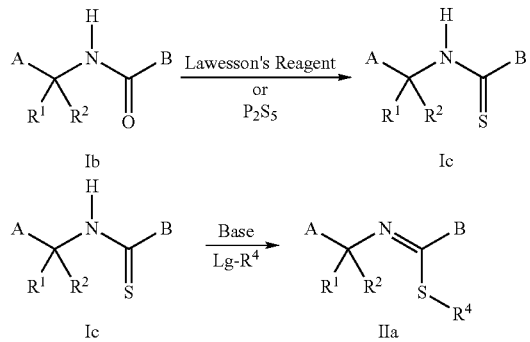

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s is singlet, d is doublet, t is triplet, q is quartet, m is multiplet, dd is doublet of doublets, dt is doublet of triplets, br s is broad singlet.

EXAMPLE 1

Preparation of 2,4-Dichloro-N-[[3-chloro-5-(trifluoromethyl)-2-pyridinyl]methyl]-6-methyl-3-pyridinecarboxamide(Compound 8 of Index Table B)

Step A: Preparation of 2,4-Dichloro-N-[[3-chloro-5-(trifluoromethyl)-2-pyridinyl]methyl]-6-methyl-3-pyridinecarboxamide Compound 8 was prepared by using 2-aminomethyl-3-chloro-5-trifluoromethylpyridine hydrochloride (prepared as described in WO99/42447). 2,4-dichloro-6-methyl-3-pyridine carbonyl chloride (0.65 g) in 2 mL of methylene chloride was added to a solution of 2-aminomethyl-3-chloro-5-trifluoromethylpyridine hydrochloride (0.79 g) and triethylamine (0.68 g) in 10 mL of methylene chloride at room temperature. The reaction mixture was stirred at room temperature overnight. The reaction mixture was then poured on top of a one-inch silica gel plug, eluted with 30 mL of methylene chloride and the eluent was rotary evaporated to yield 0.69 g of the amide (Compound 8), a compound of the invention. $^1$H NMR (CDCl$_3$; 300 MHz) δ 2.57 (s, 3H), 4.96 (m, 2H), 7.22 (s, 1H), 7.48 (bs, 1H), 8.00 (s, 1H), 8.71 (s, 1H).

EXAMPLE 2

Preparation of 2,4-Dichloro-N-[[3-chloro-5-(trifluoromethyl)-2-pyridinyl]methyl]-3-pyridinecarboxamide Step A: Preparation of 2,4-dichloropyridine A solution of 6.7 g of 4-nitropyridine N-oxide in POCl$_3$ was refluxed for 3 hours and then cooled to room temperature. The solvent was removed under vacuum to leave an oily residue. Saturated sodium bicarbonate solution (200 mL) was carefully added, followed by extraction with methylene chloride (2×). The methylene chloride was then removed under vacuum to provide an oil that was filtered through a plug of silica gel, eluting with 20% ethyl acetate in hexanes. Removal of the solvent under vacuum left 1.6 g of an oil. $^1$H NMR (CDCl$_3$; 300 MHz) δ 7.25 (d of d, 1H, J is 1.7, 5.4 Hz), 7.38 (d, 1H, J is 1.7 Hz), 8.31 (d, 1H, J is 5.4 Hz).

Step B: Preparation of 2,4-dichloro-3-pyridine carboxaldehyde

Under nitrogen, a solution of 1.6 g of 2,4-dichloropyridine in 5 mL dry tetrahydrofuran (THF) was added to a solution of 6 mL of lithium diisopropyl amide in 25 mL of THF at −70° C., followed by stirring at this temperature for 3 hours. Then 1 mL of dry N,N-dimethylformamide was added at −70° C. followed by stirring at this temperature for 1 hour. Then 25 mL of saturated ammonium chloride solution was added and the reaction mixture was stirred at room temperature overnight. The reaction mixture was diluted with 25 mL of water and extracted with ethyl acetate (2×). The combine organic phases were distilled under vacuum to give solids that were dissolved in 5 mL of methylene chloride and filtered through silica gel, eluting with 100% methylene chloride. Removal of the solvent under vacuum provided the title intermediate as a solid. $^1$H NMR (CDCl$_3$; 300 MHz) δ 7.41 (d, 1H, J is 5.3 Hz), 8.42 (d, 1H, J is 5.2 Hz), 10.5 (s, 1H).

Step C: Preparation of 2,4-dichloronicotinic acid

A solution of 0.40 g of the aldehyde from Step B was dissolved in 6 mL of THF and then added to a solution of 0.27 g of sodium chlorite and 0.29 g of sulfamic acid in 6 mL of water. The reaction mixture was stirred at room temperature overnight. The reaction mixture was diluted with 1 N sodium hydroxide (10 mL) and extracted with diethyl ether (1×). The aqueous layer was then acidified with concentrated HCl, extracted with methylene chloride (2×), and the combine methylene chloride extracts were dried over magnesium sulfate. The methylene chloride was removed under vacuum to give 0.22 g of a solid. $^1$H NMR (CDCl$_3$; 300 MHz) δ 7.38 (d, 1H J is 5.4 Hz), 8.40 (d, 1H, J is 5.5 Hz), 8.60 (bs, 1H).

Step D: Preparation of 2,4-Dichloro-N-[[3-chloro-5-(trifluoromethyl)-2-pyridinyl]methyl]-3-pyridinecarboxamide A solution of 0.22 g of the acid from Step C was refluxed in thionyl chloride for 1 hour followed by removal of the solvent under vacuum to give an oil. The oil was dissolved in 1 mL of methylene chloride and added to a solution of 2-aminomethyl-3-chloro-5-trifluoromethylpyridine hydrochloride (0.25 g) and triethylamine (0.20 g) in 9 mL of methylene chloride at room temperature. The reaction mixture was stirred at room temperature overnight. The reaction mixture was then filtered through silica gel, eluting with 100% methylene chloride. Removal of the solvent under vacuum provided the title compound as a solid, m.p. 122–124° C.

EXAMPLE 3

Preparation of 2,4-Dichloro-N-[1-[3-chloro-5-(trifluoromethyl)-2-pyridinyl]ethyl]-3-pyridinecarboxamide Step A: Preparation of 3–Chloro-α-methyl-5-(trifluoromethyl)-2-pyridinemethanamine N-(diphenylmethylene)glycine ethyl ester (2.25 g) was added to a suspension of sodium hydride (0.74 g of 60% oil dispersion) in 20 mL of dry N,N-dimethylformamide at room temperature, resulting in vigorous gas evolution. After stirring at room temperature for five minutes, 2 g of 2,3-dichloro-5-trifluoromethylpyridine was added, followed by stirring at room temperature for 1 hour. Then 0.80 mL of methyl iodide was added followed by stirring at room temperature overnight. The reaction mixture was poured onto ice water, extracted with diethyl ether (2×), and distilled under vacuum to remove the solvent leaving an oil. The oil was then refluxed in 6 N HCl overnight. The reaction mixture was cooled to room temperature, made basic with solid sodium carbonate and extracted with diethyl ether (2×). The combined extracts were dried over magnesium sulfate and distilled under vacuum to remove the solvent, leaving 1.5 g of an oil. $^1$H NMR (CDCl$_3$; 300 MHz) δ 1.4 (d, 3H, J is 6.6 Hz), 4.6 (bs, 1H), 7.88 (m, 1H), 8.75 (bs, 1H).

Step B: Preparation of 2,4-Dichloro-N-[1-[3-chloro-5-(trifluoromethyl)-2-pyridinyl]ethyl]-3-pyridinecarboxamide 2,4-Dichloronicotinoyl chloride (0.40 g), made as in Example 1, Step C, was added to a solution of the amine intermediate from Step A (0.66 g) and triethylamine (0.70 g) in 30 mL of methylene chloride at room temperature followed by stirring overnight. The reaction mixture was distilled under vacuum to remove the solvent, giving an oil that was filtered through silica gel using 100% methylene chloride as the eluent. The solvent was then removed under vacuum to give the title compound, a compound of the invention, as a red oil.

$^1$H NMR (CDCl$_3$; 300 MHz) δ 1.62 (d, 3H, J is 6.7 Hz), 5.48 (m, 1H), 7.35 (d, 1H, J is 5.2 Hz), 7.40 (d, 1H, J is 6.9), 7.99 (d, 1H, J is 1.8 Hz), 8.34 (d, 1H, J is 5.2), 8.70 (s, 1H).

EXAMPLE 4

Preparation of (+)-2,4-Dichloro-N-[1-[3-chloro-5-(trifluoromethyl)-2-pyridinyl]ethyl]-3-pyridinecarboxamide Step A: Resolution of 3-Chloro-α-methyl-5-(trifluoromethyl)-2-pyridinemethanamine:

(−)-Menthyl chloroformate (0.92 g) was added to a solution of the alpha-methyl amine from Example 3, Step A (1 g) and triethylamine (1.2 mL) in 25 mL of THF at room temperature followed by stirring at room temperature for 30 minutes. The solvent was then removed under vacuum to give an oil comprising two menthylcarbamate diastereomers that were separated via column chromatography (5% diethyl ether in hexanes as eluent) to give 0.20 g of the more polar diastereomer as an oil. This oil was then refluxed in 5 mL of trifluoroacetic acid for 4 hours to cleave the menthylcarbamate. The reaction mixture was allowed to cool to room temperature and diluted with water (30 mL), made basic with solid sodium carbonate and extracted with methylene chloride. The organic layer was dried over magnesium sulfate and distilled under vacuum to give 60 mg of the enantiomerically-enriched amine intermediate as an oil. $^1$H NMR (CDCl$_3$; 300 MHz) δ 1.41 (d, 3H, J is 6.7 Hz), 1.9 (bs, 2H), 4.60 (m, 1H), 7.88 (m, 1H), 8.74 (s, 1H).

Step B: Preparation of (+)-2,4-Dichloro-N-[1-[3-chloro-5-(trifluoromethyl)-2-pyridinyl]ethyl]-3-pyridinecarboxamide:

2,4-Dichloronicotinoyl chloride (0.56 g), made as in Example 1, Step C was added to a solution of the enantiomerically-enriched amine from Step A (60 mg) and triethylamine (54 mg) in 10 mL of methylene chloride at room temperature followed by stirring overnight. The reaction mixture was then filtered through silica gel using 100% methylene chloride as the eluent. The solvent was removed under vacuum to give the title compound, a compound of the invention, as a solid, m.p. 110–111° C. Polarimetric measurements of a solution of approximately 2 mg of the title compound in 1 mL of CDCl$_3$ rotates plane polarized light in the (+) or dextro direction.

The enantiomer of Example 4, (−)-2,4-Dichloro-N-[-1-[3-chloro-5-(trifluoromethyl)-2-pyridinyl]ethyl]-3-pyridinecarboxamide, was prepared in analogoous fashion using 3-chloro-α-methyl-5-(trifluoromethyl)-2-pyridinemethanamine that has been enriched in the opposite enantiomer from that obtained in Example 4, Step A.

EXAMPLE 5

Preparation of N-[1-(5-bromo-3-chloro-2-pyridinyl)ethyl]-2,4-dichloro-3-pyridinecarboxamide Step A: Preparation of 5-bromo-3-chloro-2(1)-pyridone A solution of 6.2 g of potassium chlorate in 100 mL of water was added to a solution of 25 g of 5-bromo-2-pyridone in 100 mL concentrated HCl pre-heated to 50° C. to 60° C. to form a thick precipitate that was stirred for 5 min. Then, 60 mL of water was added to facilitate stirring and the mixture was stirred at room temperature overnight. The reaction mixture was filtered, triturated with water (2×), and the precipitate suction-dried to yield 17.7 g of the desired intermediate as a solid. NMR (CDCl$_3$, 300 MHz): δ 7.53 (d, 1H, J is 2.6 Hz), 7.75 (d, 1H, J is 2.5 Hz)

Step B: Preparation of 5-bromo-2,3-dichloropyridine

The product of Step A (17.7 g) and 10 g of PCl$_5$ were combined into 100 mL POCl$_3$, and the mixture was refluxed for 4 hours with scrubbing. The reaction mixture was concentrated under reduced pressure to remove most of the POCl$_3$, carefully poured into warm water, cooled to room temperature and then extracted with methylene chloride (2×). The combined extracts were dried over magnesium sulfate and concentrated to give an oil which was subjected to column chromatography (8:2/hexanes:EtOAc) to give 4.2 g of the desired intermediate as an oil. NMR (CDCl$_3$; 300 MHz): δ 7.94 (d, 1H, J is 2.2 Hz), 8.37 (d, 1H, J is 2.3 Hz).

Step C: Preparation of 5-Bromo-3-chloro-α-methyl-2-pyridinemethanamine hydrochloride Under nitrogen, 4.1 g of the title compound from Step B was added to a suspension of sodium hydride (60% oil suspension) in 30 mL of dry N,N-dimethylformamide, cooled to 0° C. N-(Diphenylmethylene)glycine ethyl ester (4.6 g) was added in portions with no exotherm, and the mixture was stirred at room temperature for 3 hours. Then, 3.4 mL of methyl iodide was added at <30° C. and the reaction mixture was stirred overnight at room temperature. The reaction mixture was diluted with water and extracted with diethyl ether (2×). The combined extracts were washed with saturated brine (1×) and reduced in vacuo to an oil that was then refluxed in 50 mL of 12N HCl for 4 hours. The reaction mixture was reduced in vacuo to an oil, cooled, and slurried with diethyl ether overnight. The ether was then decanted off and the residue was dried in a vacuum oven to give 1.3 g of the desired intermediate as a solid. NMR (CDCl$_3$; 300 MHz): 1.40 and 1.46 (2 doublets, 3H, J is 7.0 Hz), 4.7 (m, 1H), 8.48 (d, 1H, J is 1.8), 8.6 (bs, 3H), 8.79 (d, 1H, J is 1.9 Hz).

Step D: Preparation of N-[1-(5-bromo-3-chloro-2-pyridinyl)ethyl]-2,4-dichloro-3-pyridinecarboxamide The product of Step C (0.80 g), 1.21 mL of triethyl amine and 0.62 g of 2,4-dichloronicotinoyl chloride were combined in that order at <20° C. in 25 mL of methylene chloride, and the mixture was stirred at room temperature overnight. The reaction mixture was reduced in vacuo to produce the title compound, a compound of the invention, as a solid. NMR (CDCl$_3$; 300 MHz): δ1.59 (d, 3H, J is 6.6 Hz), 5.75 (m, 1H), 7.3 (bs, 1H), 7.34 (d, 1H, J is 5.2 Hz), 7.91 (d, 1H, J is 1.9 Hz), 8.33 (d, 1H, J is 5.4 Hz), 8.49 (d, 1H, J is 1.9 Hz).

EXAMPLE 6

Preparation of 2,4-Dichloro-N-[1-(3,5-dichloro-2-pyridinyl)ethyl]-3-pyridinecarboxamide Example 6 was prepared in analogous fashion to Example 5 using 2-bromo-3,5-dichloropyridine as the staring material and subjecting this material to conditions analogous to those described in Steps C (to prepare 3,5-dichloro-α-methyl-2-pyridinemethanamine) and D of Example 5 to give the title compound, a compound of the invention, as a solid. NMR (CDCl$_3$; 300 MHz): δ 1.58 (d, 3H, J is 6.6 Hz), 5.7–5.8 (m, 1H), 7.4 (m, 2H), 7.77 (m, 1H), 8.35 (m, 1H), 8.40 (m, 1H).

By the procedures described herein together with methods known in the art, the following compounds of Tables 1–9 can be prepared. The following abbreviations are used in the Tables which follow: t is tertiary, s is secondary, n is normal, i is iso, c is cyclo, Me is methyl, Et is ethyl, Pr is propyl, i-Pr is isopropyl, Bu is butyl, Ph is phenyl, OMe is methoxy, OEt is ethoxy, SMe is methylthio, SEt is ethylthio, CN is cyano, NO$_2$ is nitro, TMS is trimethylsilyl, S(O)Me is methylsulfinyl, and S(O)$_2$Me is methylsulfonyl. The substituents M, Q and R are equivalent to independent R$^5$ substituents that have been located in the positions indicated. The substituents T, U and V are equivalent to independent R$^6$ substituents that have been located in the positions indicated.

TABLE 1

| T | U | V | T | U | V |
|---|---|---|---|---|---|
| Me | Me | Me | Br | Me | Me |
| Me | Me | F | Br | Me | F |
| Me | Me | Cl | Br | Me | Cl |

TABLE 1-continued

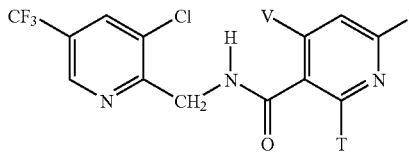

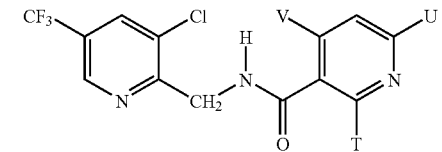

| T | U | V | T | U | V |
|---|---|---|---|---|---|
| Me | Me | Br | Br | Me | Br |
| Me | Me | CF₃ | Br | Me | CF₃ |
| Me | Me | NO₂ | Br | Me | NO₂ |
| Me | Me | OMe | Br | Me | OMe |
| F | Me | Me | CF₃ | Me | Me |
| F | Me | F | CF₃ | Me | F |
| F | Me | Cl | CF₃ | Me | Cl |
| F | Me | Br | CF₃ | Me | Br |
| F | Me | CF₃ | CF₃ | Me | CF₃ |
| F | Me | NO₂ | CF₃ | Me | NO₂ |
| F | Me | OMe | CF₃ | Me | OMe |
| Cl | Me | Me | NO₂ | Me | Me |
| Cl | Me | F | NO₂ | Me | F |
| Cl | Me | Cl | NO₂ | Me | Cl |
| Cl | Me | Br | NO₂ | Me | Br |
| Cl | Me | CF₃ | NO₂ | Me | CF₃ |
| Cl | Me | NO₂ | NO₂ | Me | NO₂ |
| Cl | Me | OMe | NO₂ | Me | OMe |
| Me | F | Me | Br | F | Me |
| Me | F | F | Br | F | F |
| Me | F | Cl | Br | F | Cl |
| Me | F | Br | Br | F | Br |
| Me | F | CF₃ | Br | F | CF₃ |
| Me | F | NO₂ | Br | F | NO₂ |
| Me | F | OMe | Br | F | OMe |
| F | F | Me | CF₃ | F | Me |
| F | F | F | CF₃ | F | F |
| F | F | Cl | CF₃ | F | Cl |
| F | F | Br | CF₃ | F | Br |
| F | F | CF₃ | CF₃ | F | CF₃ |
| F | F | NO₂ | CF₃ | F | NO₂ |
| F | F | OMe | CF₃ | F | OMe |
| Cl | F | Me | NO₂ | F | Me |
| Cl | F | F | NO₂ | F | F |
| Cl | F | Cl | NO₂ | F | Cl |
| Cl | F | Br | NO₂ | F | Br |
| Cl | F | CF₃ | NO₂ | F | CF₃ |
| Cl | F | NO₂ | NO₂ | F | NO₂ |
| Cl | F | OMe | NO₂ | F | OMe |
| Me | Cl | Me | Br | Cl | Me |
| Me | Cl | F | Br | Cl | F |
| Me | Cl | Cl | Br | Cl | Cl |
| Me | Cl | Br | Br | Cl | Br |
| Me | Cl | CF₃ | Br | Cl | CF₃ |
| Me | Cl | NO₂ | Br | Cl | NO₂ |
| Me | Cl | OMe | Br | Cl | OMe |
| F | Cl | Me | CF₃ | Cl | Me |
| F | Cl | F | CF₃ | Cl | F |
| F | Cl | Cl | CF₃ | Cl | Cl |
| F | Cl | Br | CF₃ | Cl | Br |
| F | Cl | CF₃ | CF₃ | Cl | CF₃ |
| F | Cl | NO₂ | CF₃ | Cl | NO₂ |
| F | Cl | OMe | CF₃ | Cl | OMe |
| Cl | Cl | Me | NO₂ | Cl | Me |
| Cl | Cl | F | NO₂ | Cl | F |
| Cl | Cl | Cl | NO₂ | Cl | Cl |
| Cl | Cl | Br | NO₂ | Cl | Br |
| Cl | Cl | CF₃ | NO₂ | Cl | CF₃ |
| Cl | Cl | NO₂ | NO₂ | Cl | NO₂ |
| Cl | Cl | OMe | NO₂ | Cl | OMe |
| Me | Br | Me | Br | Br | Me |
| Me | Br | F | Br | Br | F |
| Me | Br | Cl | Br | Br | Cl |
| Me | Br | Br | Br | Br | Br |
| Me | Br | CF₃ | Br | Br | CF₃ |
| Me | Br | NO₂ | Br | Br | NO₂ |
| Me | Br | OMe | Br | Br | OMe |
| F | Br | Me | CF₃ | Br | Me |
| F | Br | F | CF₃ | Br | F |
| F | Br | Cl | CF₃ | Br | Cl |
| F | Br | Br | CF₃ | Br | Br |
| F | Br | CF₃ | CF₃ | Br | CF₃ |
| F | Br | NO₂ | CF₃ | Br | NO₂ |
| F | Br | OMe | CF₃ | Br | OMe |
| Cl | Br | Me | NO₂ | Br | Me |
| Cl | Br | F | NO₂ | Br | F |
| Cl | Br | Cl | NO₂ | Br | Cl |
| Cl | Br | Br | NO₂ | Br | Br |
| Cl | Br | CF₃ | NO₂ | Br | CF₃ |
| Cl | Br | NO₂ | NO₂ | Br | NO₂ |
| Cl | Br | OMe | NO₂ | Br | OMe |
| Me | CF₃ | Me | Br | CF₃ | Me |
| Me | CF₃ | F | Br | CF₃ | F |
| Me | CF₃ | Cl | Br | CF₃ | Cl |
| Me | CF₃ | Br | Br | CF₃ | Br |
| Me | CF₃ | CF₃ | Br | CF₃ | CF₃ |
| Me | CF₃ | NO₂ | Br | CF₃ | NO₂ |
| Me | CF₃ | OMe | Br | CF₃ | OMe |
| F | CF₃ | Me | CF₃ | CF₃ | Me |
| F | CF₃ | F | CF₃ | CF₃ | F |
| F | CF₃ | Cl | CF₃ | CF₃ | Cl |
| F | CF₃ | Br | CF₃ | CF₃ | Br |
| F | CF₃ | CF₃ | CF₃ | CF₃ | CF₃ |
| F | CF₃ | NO₂ | CF₃ | CF₃ | NO₂ |
| F | CF₃ | OMe | CF₃ | CF₃ | OMe |
| Cl | CF₃ | Me | NO₂ | CF₃ | Me |
| Cl | CF₃ | F | NO₂ | CF₃ | F |
| Cl | CF₃ | Cl | NO₂ | CF₃ | Cl |
| Cl | CF₃ | Br | NO₂ | CF₃ | Br |
| Cl | CF₃ | CF₃ | NO₂ | CF₃ | CF₃ |
| Cl | CF₃ | NO₂ | NO₂ | CF₃ | NO₂ |
| Cl | CF₃ | OMe | NO₂ | CF₃ | OMe |
| Me | NO₂ | Me | Br | NO₂ | Me |
| Me | NO₂ | F | Br | NO₂ | F |
| Me | NO₂ | Cl | Br | NO₂ | Cl |
| Me | NO₂ | Br | Br | NO₂ | Br |
| Me | NO₂ | CF₃ | Br | NO₂ | CF₃ |
| Me | NO₂ | NO₂ | Br | NO₂ | NO₂ |
| Me | NO₂ | OMe | Br | NO₂ | OMe |
| F | NO₂ | Me | CF₃ | NO₂ | Me |
| F | NO₂ | F | CF₃ | NO₂ | F |
| F | NO₂ | Cl | CF₃ | NO₂ | Cl |
| F | NO₂ | Br | CF₃ | NO₂ | Br |
| F | NO₂ | CF₃ | CF₃ | NO₂ | CF₃ |
| F | NO₂ | NO₂ | CF₃ | NO₂ | NO₂ |
| F | NO₂ | OMe | CF₃ | NO₂ | OMe |
| Cl | NO₂ | Me | NO₂ | NO₂ | Me |
| Cl | NO₂ | F | NO₂ | NO₂ | F |
| Cl | NO₂ | Cl | NO₂ | NO₂ | Cl |
| Cl | NO₂ | Br | NO₂ | NO₂ | Br |
| Cl | NO₂ | CF₃ | NO₂ | NO₂ | CF₃ |
| Cl | NO₂ | NO₂ | NO₂ | NO₂ | NO₂ |
| Cl | NO₂ | OMe | NO₂ | NO₂ | OMe |
| Me | OMe | Me | Br | OMe | Me |
| Me | OMe | F | Br | OMe | F |
| Me | OMe | Cl | Br | OMe | Cl |
| Me | OMe | Br | Br | OMe | Br |
| Me | OMe | CF₃ | Br | OMe | CF₃ |
| Me | OMe | NO₂ | Br | OMe | NO₂ |
| Me | OMe | OMe | Br | OMe | OMe |
| F | OMe | Me | CF₃ | OMe | Me |
| F | OMe | F | CF₃ | OMe | F |
| F | OMe | Cl | CF₃ | OMe | Cl |
| F | OMe | Br | CF₃ | OMe | Br |
| F | OMe | CF₃ | CF₃ | OMe | CF₃ |
| F | OMe | NO₂ | CF₃ | OMe | NO₂ |

TABLE 1-continued

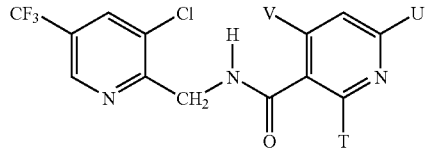

| T | U | V | T | U | V |
|---|---|---|---|---|---|
| F | OMe | OMe | CF₃ | OMe | OMe |
| Cl | OMe | Me | NO₂ | OMe | Me |
| Cl | OMe | F | NO₂ | OMe | F |
| Cl | OMe | Cl | NO₂ | OMe | Cl |
| Cl | OMe | Br | NO₂ | OMe | Br |
| Cl | OMe | CF₃ | NO₂ | OMe | CF₃ |
| Cl | OMe | NO₂ | NO₂ | OMe | NO₂ |
| Cl | OMe | OMe | NO₂ | OMe | OMe |
| Me | H | Me | Br | H | Me |
| Me | H | F | Br | H | F |
| Me | H | Cl | Br | H | Cl |
| Me | H | Br | Br | H | Br |
| Me | H | CF₃ | Br | H | CF₃ |
| Me | H | NO₂ | Br | H | NO₂ |
| Me | H | OMe | Br | H | OMe |
| F | H | Me | CF₃ | H | Me |
| F | H | F | CF₃ | H | F |
| F | H | Cl | CF₃ | H | Cl |
| F | H | Br | CF₃ | H | Br |
| F | H | CF₃ | CF₃ | H | CF₃ |
| F | H | NO₂ | CF₃ | H | NO₂ |
| F | H | OMe | CF₃ | H | OMe |
| Cl | H | Me | NO₂ | H | Me |
| Cl | H | F | NO₂ | H | F |
| Cl | H | Cl | NO₂ | H | Cl |
| Cl | H | Br | NO₂ | H | Br |
| Cl | H | CF₃ | NO₂ | H | CF₃ |
| Cl | H | NO₂ | NO₂ | H | NO₂ |
| Cl | H | OMe | NO₂ | H | OMe |
| OMe | Me | Me | OMe | Br | Me |
| OMe | Me | F | OMe | Br | F |
| OMe | Me | Cl | OMe | Br | Cl |
| OMe | Me | Br | OMe | Br | Br |
| OMe | Me | CF₃ | OMe | Br | CF₃ |
| OMe | Me | NO₂ | OMe | Br | NO₂ |
| OMe | Me | OMe | OMe | Br | OMe |
| OMe | F | Me | OMe | CF₃ | Me |
| OMe | F | F | OMe | CF₃ | F |
| OMe | F | Cl | OMe | CF₃ | Cl |
| OMe | F | Br | OMe | CF₃ | Br |
| OMe | F | CF₃ | OMe | CF₃ | CF₃ |
| OMe | F | NO₂ | OMe | CF₃ | NO₂ |
| OMe | F | OMe | OMe | CF₃ | OMe |
| OMe | Cl | Me | OMe | NO₂ | Me |
| OMe | Cl | F | OMe | NO₂ | F |
| OMe | Cl | Cl | OMe | NO₂ | Cl |
| OMe | Cl | Br | OMe | NO₂ | Br |
| OMe | Cl | CF₃ | OMe | NO₂ | CF₃ |
| OMe | Cl | NO₂ | OMe | NO₂ | NO₂ |
| OMe | Cl | OMe | OMe | NO₂ | OMe |
| OMe | H | Me | OMe | H | Br |
| OMe | H | F | OMe | H | CF₃ |
| OMe | H | Cl | OMe | H | NO₂ |
| OMe | H | OMe | OMe | OMe | Me |
| OMe | OMe | CF₃ | OMe | OMe | F |
| OMe | OMe | NO₂ | OMe | OMe | Cl |
| OMe | OMe | OMe | OMe | OMe | Br |

TABLE 2

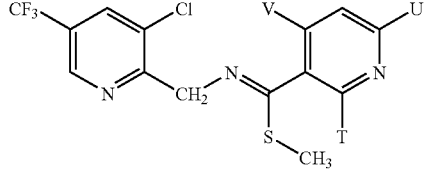

| T | U | V | T | U | V |
|---|---|---|---|---|---|
| Me | Me | Me | Br | Me | Me |
| Me | Me | F | Br | Me | F |
| Me | Me | Cl | Br | Me | Cl |
| Me | Me | Br | Br | Me | Br |
| Me | Me | CF₃ | Br | Me | CF₃ |
| Me | Me | NO₂ | Br | Me | NO₂ |
| Me | Me | OMe | Br | Me | OMe |
| F | Me | Me | CF₃ | Me | Me |
| F | Me | F | CF₃ | Me | F |
| F | Me | Cl | CF₃ | Me | Cl |
| F | Me | Br | CF₃ | Me | Br |
| F | Me | CF₃ | CF₃ | Me | CF₃ |
| F | Me | NO₂ | CF₃ | Me | NO₂ |
| F | Me | OMe | CF₃ | Me | OMe |
| Cl | Me | Me | NO₂ | Me | Me |
| Cl | Me | F | NO₂ | Me | F |
| Cl | Me | Cl | NO₂ | Me | Cl |
| Cl | Me | Br | NO₂ | Me | Br |
| Cl | Me | CF₃ | NO₂ | Me | CF₃ |
| Cl | Me | NO₂ | NO₂ | Me | NO₂ |
| Cl | Me | OMe | NO₂ | Me | OMe |
| Me | F | Me | Br | F | Me |
| Me | F | F | Br | F | F |
| Me | F | Cl | Br | F | Cl |
| Me | F | Br | Br | F | Br |
| Me | F | CF₃ | Br | F | CF₃ |
| Me | F | NO₂ | Br | F | NO₂ |
| Me | F | OMe | Br | F | OMe |
| F | F | Me | CF₃ | F | Me |
| F | F | F | CF₃ | F | F |
| F | F | Cl | CF₃ | F | Cl |
| F | F | Br | CF₃ | F | Br |
| F | F | CF₃ | CF₃ | F | CF₃ |
| F | F | NO₂ | CF₃ | F | NO₂ |
| F | F | OMe | CF₃ | F | OMe |
| Cl | F | Me | NO₂ | F | Me |
| Cl | F | F | NO₂ | F | F |
| Cl | F | Cl | NO₂ | F | Cl |
| Cl | F | Br | NO₂ | F | Br |
| Cl | F | CF₃ | NO₂ | F | CF₃ |
| Cl | F | NO₂ | NO₂ | F | NO₂ |
| Cl | F | OMe | NO₂ | F | OMe |
| Me | Cl | Me | Br | Cl | Me |
| Me | Cl | F | Br | Cl | F |
| Me | Cl | Cl | Br | Cl | Cl |
| Me | Cl | Br | Br | Cl | Br |
| Me | Cl | CF₃ | Br | Cl | CF₃ |
| Me | Cl | NO₂ | Br | Cl | NO₂ |
| Me | Cl | OMe | Br | Cl | OMe |
| F | Cl | Me | CF₃ | Cl | Me |
| F | Cl | F | CF₃ | Cl | F |
| F | Cl | Cl | CF₃ | Cl | Cl |
| F | Cl | Br | CF₃ | Cl | Br |
| F | Cl | CF₃ | CF₃ | Cl | CF₃ |
| F | Cl | NO₂ | CF₃ | Cl | NO₂ |
| F | Cl | OMe | CF₃ | Cl | OMe |
| Cl | Cl | Me | NO₂ | Cl | Me |
| Cl | Cl | F | NO₂ | Cl | F |
| Cl | Cl | Cl | NO₂ | Cl | Cl |
| Cl | Cl | Br | NO₂ | Cl | Br |
| Cl | Cl | CF₃ | NO₂ | Cl | CF₃ |
| Cl | Cl | NO₂ | NO₂ | Cl | NO₂ |
| Cl | Cl | OMe | NO₂ | Cl | OMe |
| Me | Br | Me | Br | Br | Me |
| Me | Br | F | Br | Br | F |
| Me | Br | Cl | Br | Br | Cl |
| Me | Br | Br | Br | Br | Br |

TABLE 2-continued

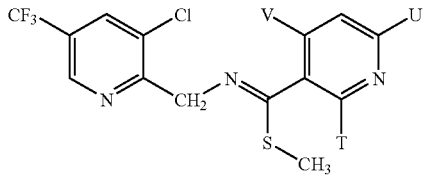

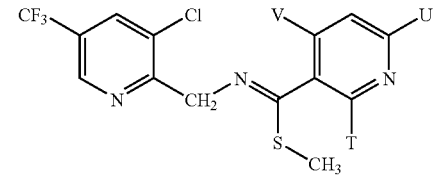

| T | U | V | T | U | V |
|---|---|---|---|---|---|
| Me | Br | CF$_3$ | Br | Br | CF$_3$ |
| Me | Br | NO$_2$ | Br | Br | NO$_2$ |
| Me | Br | OMe | Br | Br | OMe |
| F | Br | Me | CF$_3$ | Br | Me |
| F | Br | F | CF$_3$ | Br | F |
| F | Br | Cl | CF$_3$ | Br | Cl |
| F | Br | Br | CF$_3$ | Br | Br |
| F | Br | CF$_3$ | CF$_3$ | Br | CF$_3$ |
| F | Br | NO$_2$ | CF$_3$ | Br | NO$_2$ |
| F | Br | OMe | CF$_3$ | Br | OMe |
| Cl | Br | Me | NO$_2$ | Br | Me |
| Cl | Br | F | NO$_2$ | Br | F |
| Cl | Br | Cl | NO$_2$ | Br | Cl |
| Cl | Br | Br | NO$_2$ | Br | Br |
| Cl | Br | CF$_3$ | NO$_2$ | Br | CF$_3$ |
| Cl | Br | NO$_2$ | NO$_2$ | Br | NO$_2$ |
| Cl | Br | OMe | NO$_2$ | Br | OMe |
| Me | CF$_3$ | Me | Br | CF$_3$ | Me |
| Me | CF$_3$ | F | Br | CF$_3$ | F |
| Me | CF$_3$ | Cl | Br | CF$_3$ | Cl |
| Me | CF$_3$ | Br | Br | CF$_3$ | Br |
| Me | CF$_3$ | CF$_3$ | Br | CF$_3$ | CF$_3$ |
| Me | CF$_3$ | NO$_2$ | Br | CF$_3$ | NO$_2$ |
| Me | CF$_3$ | OMe | Br | CF$_3$ | OMe |
| F | CF$_3$ | Me | CF$_3$ | CF$_3$ | Me |
| F | CF$_3$ | F | CF$_3$ | CF$_3$ | F |
| F | CF$_3$ | Cl | CF$_3$ | CF$_3$ | Cl |
| F | CF$_3$ | Br | CF$_3$ | CF$_3$ | Br |
| F | CF$_3$ | CF$_3$ | CF$_3$ | CF$_3$ | CF$_3$ |
| F | CF$_3$ | NO$_2$ | CF$_3$ | CF$_3$ | NO$_2$ |
| F | CF$_3$ | OMe | CF$_3$ | CF$_3$ | OMe |
| Cl | CF$_3$ | Me | NO$_2$ | CF$_3$ | Me |
| Cl | CF$_3$ | F | NO$_2$ | CF$_3$ | F |
| Cl | CF$_3$ | Cl | NO$_2$ | CF$_3$ | Cl |
| Cl | CF$_3$ | Br | NO$_2$ | CF$_3$ | Br |
| Cl | CF$_3$ | CF$_3$ | NO$_2$ | CF$_3$ | CF$_3$ |
| Cl | CF$_3$ | NO$_2$ | NO$_2$ | CF$_3$ | NO$_2$ |
| Cl | CF$_3$ | OMe | NO$_2$ | CF$_3$ | OMe |
| Me | NO$_2$ | Me | Br | NO$_2$ | Me |
| Me | NO$_2$ | F | Br | NO$_2$ | F |
| Me | NO$_2$ | Cl | Br | NO$_2$ | Cl |
| Me | NO$_2$ | Br | Br | NO$_2$ | Br |
| Me | NO$_2$ | CF$_3$ | Br | NO$_2$ | CF$_3$ |
| Me | NO$_2$ | NO$_2$ | Br | NO$_2$ | NO$_2$ |
| Me | NO$_2$ | OMe | Br | NO$_2$ | OMe |
| F | NO$_2$ | Me | CF$_3$ | NO$_2$ | Me |
| F | NO$_2$ | F | CF$_3$ | NO$_2$ | F |
| F | NO$_2$ | Cl | CF$_3$ | NO$_2$ | Cl |
| F | NO$_2$ | Br | CF$_3$ | NO$_2$ | Br |
| F | NO$_2$ | CF$_3$ | CF$_3$ | NO$_2$ | CF$_3$ |
| F | NO$_2$ | NO$_2$ | CF$_3$ | NO$_2$ | NO$_2$ |
| F | NO$_2$ | OMe | CF$_3$ | NO$_2$ | OMe |
| Cl | NO$_2$ | Me | NO$_2$ | NO$_2$ | Me |
| Cl | NO$_2$ | F | NO$_2$ | NO$_2$ | F |
| Cl | NO$_2$ | Cl | NO$_2$ | NO$_2$ | Cl |
| Cl | NO$_2$ | Br | NO$_2$ | NO$_2$ | Br |
| Cl | NO$_2$ | CF$_3$ | NO$_2$ | NO$_2$ | CF$_3$ |
| Cl | NO$_2$ | NO$_2$ | NO$_2$ | NO$_2$ | NO$_2$ |
| Cl | NO$_2$ | OMe | NO$_2$ | NO$_2$ | OMe |
| Me | OMe | Me | Br | OMe | Me |
| Me | OMe | F | Br | OMe | F |
| Me | OMe | Cl | Br | OMe | Cl |
| Me | OMe | Br | Br | OMe | Br |
| Me | OMe | CF$_3$ | Br | OMe | CF$_3$ |
| Me | OMe | NO$_2$ | Br | OMe | NO$_2$ |
| Me | OMe | OMe | Br | OMe | OMe |
| F | OMe | Me | CF$_3$ | OMe | Me |
| F | OMe | F | CF$_3$ | OMe | F |
| F | OMe | Cl | CF$_3$ | OMe | Cl |
| F | OMe | Br | CF$_3$ | OMe | Br |
| F | OMe | CF$_3$ | CF$_3$ | OMe | CF$_3$ |
| F | OMe | NO$_2$ | CF$_3$ | OMe | NO$_2$ |
| F | OMe | OMe | CF$_3$ | OMe | OMe |
| Cl | OMe | Me | NO$_2$ | OMe | Me |
| Cl | OMe | F | NO$_2$ | OMe | F |
| Cl | OMe | Cl | NO$_2$ | OMe | Cl |
| Cl | OMe | Br | NO$_2$ | OMe | Br |
| Cl | OMe | CF$_3$ | NO$_2$ | OMe | CF$_3$ |
| Cl | OMe | NO$_2$ | NO$_2$ | OMe | NO$_2$ |
| Cl | OMe | OMe | NO$_2$ | OMe | OMe |
| Me | H | Me | Br | H | Me |
| Me | H | F | Br | H | F |
| Me | H | Cl | Br | H | Cl |
| Me | H | Br | Br | H | Br |
| Me | H | CF$_3$ | Br | H | CF$_3$ |
| Me | H | NO$_2$ | Br | H | NO$_2$ |
| Me | H | OMe | Br | H | OMe |
| F | H | Me | CF$_3$ | H | Me |
| F | H | F | CF$_3$ | H | F |
| F | H | Cl | CF$_3$ | H | Cl |
| F | H | Br | CF$_3$ | H | Br |
| F | H | CF$_3$ | CF$_3$ | H | CF$_3$ |
| F | H | NO$_2$ | CF$_3$ | H | NO$_2$ |
| F | H | OMe | CF$_3$ | H | OMe |
| Cl | H | Me | NO$_2$ | H | Me |
| Cl | H | F | NO$_2$ | H | F |
| Cl | H | Cl | NO$_2$ | H | Cl |
| Cl | H | Br | NO$_2$ | H | Br |
| Cl | H | CF$_3$ | NO$_2$ | H | CF$_3$ |
| Cl | H | NO$_2$ | NO$_2$ | H | NO$_2$ |
| Cl | H | OMe | NO$_2$ | H | OMe |
| OMe | Me | Me | OMe | Br | Me |
| OMe | Me | F | OMe | Br | F |
| OMe | Me | Cl | OMe | Br | Cl |
| OMe | Me | Br | OMe | Br | Br |
| OMe | Me | CF$_3$ | OMe | Br | CF$_3$ |
| OMe | Me | NO$_2$ | OMe | Br | NO$_2$ |
| OMe | Me | OMe | OMe | Br | OMe |
| OMe | F | Me | OMe | CF$_3$ | Me |
| OMe | F | F | OMe | CF$_3$ | F |
| OMe | F | Cl | OMe | CF$_3$ | Cl |
| OMe | F | Br | OMe | CF$_3$ | Br |
| OMe | F | CF$_3$ | OMe | CF$_3$ | CF$_3$ |
| OMe | F | NO$_2$ | OMe | CF$_3$ | NO$_2$ |
| OMe | F | OMe | OMe | CF$_3$ | OMe |
| OMe | Cl | Me | OMe | NO$_2$ | Me |
| OMe | Cl | F | OMe | NO$_2$ | F |
| OMe | Cl | Cl | OMe | NO$_2$ | Cl |
| OMe | Cl | Br | OMe | NO$_2$ | Br |
| OMe | Cl | CF$_3$ | OMe | NO$_2$ | CF$_3$ |
| OMe | Cl | NO$_2$ | OMe | NO$_2$ | NO$_2$ |
| OMe | Cl | OMe | OMe | NO$_2$ | OMe |
| OMe | H | Me | OMe | H | Br |
| OMe | H | F | OMe | H | CF$_3$ |
| OMe | H | Cl | OMe | H | NO$_2$ |
| OMe | H | OMe | OMe | OMe | Me |
| OMe | OMe | CF$_3$ | OMe | OMe | F |
| OMe | OMe | NO$_2$ | OMe | OMe | Cl |
| OMe | OMe | OMe | OMe | OMe | Br |

TABLE 3

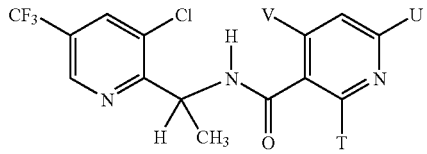

| T | U | V | T | U | V |
|---|---|---|---|---|---|
| Me | Me | Me | Br | Me | Me |
| Me | Me | F | Br | Me | F |
| Me | Me | Cl | Br | Me | Cl |
| Me | Me | Br | Br | Me | Br |
| Me | Me | CF$_3$ | Br | Me | CF$_3$ |
| Me | Me | NO$_2$ | Br | Me | NO$_2$ |
| Me | Me | OMe | Br | Me | OMe |
| F | Me | Me | CF$_3$ | Me | Me |
| F | Me | F | CF$_3$ | Me | F |
| F | Me | Cl | CF$_3$ | Me | Cl |
| F | Me | Br | CF$_3$ | Me | Br |
| F | Me | CF$_3$ | CF$_3$ | Me | CF$_3$ |
| F | Me | NO$_2$ | CF$_3$ | Me | NO$_2$ |
| F | Me | OMe | CF$_3$ | Me | OMe |
| Cl | Me | Me | NO$_2$ | Me | Me |
| Cl | Me | F | NO$_2$ | Me | F |
| Cl | Me | Cl | NO$_2$ | Me | Cl |
| Cl | Me | Br | NO$_2$ | Me | Br |
| Cl | Me | CF$_3$ | NO$_2$ | Me | CF$_3$ |
| Cl | Me | NO$_2$ | NO$_2$ | Me | NO$_2$ |
| Cl | Me | OMe | NO$_2$ | Me | OMe |
| Me | F | Me | Br | F | Me |
| Me | F | F | Br | F | F |
| Me | F | Cl | Br | F | Cl |
| Me | F | Br | Br | F | Br |
| Me | F | CF$_3$ | Br | F | CF$_3$ |
| Me | F | NO$_2$ | Br | F | NO$_2$ |
| Me | F | OMe | Br | F | OMe |
| F | F | Me | CF$_3$ | F | Me |
| F | F | F | CF$_3$ | F | F |
| F | F | Cl | CF$_3$ | F | Cl |
| F | F | Br | CF$_3$ | F | Br |
| F | F | CF$_3$ | CF$_3$ | F | CF$_3$ |
| F | F | NO$_2$ | CF$_3$ | F | NO$_2$ |
| F | F | OMe | CF$_3$ | F | OMe |
| Cl | F | Me | NO$_2$ | F | Me |
| Cl | F | F | NO$_2$ | F | F |
| Cl | F | Cl | NO$_2$ | F | Cl |
| Cl | F | Br | NO$_2$ | F | Br |
| Cl | F | CF$_3$ | NO$_2$ | F | CF$_3$ |
| Cl | F | NO$_2$ | NO$_2$ | F | NO$_2$ |
| Cl | F | OMe | NO$_2$ | F | OMe |
| Me | Cl | Me | Br | Cl | Me |
| Me | Cl | F | Br | Cl | F |
| Me | Cl | Cl | Br | Cl | Cl |
| Me | Cl | Br | Br | Cl | Br |
| Me | Cl | CF$_3$ | Br | Cl | CF$_3$ |
| Me | Cl | NO$_2$ | Br | Cl | NO$_2$ |
| Me | Cl | OMe | Br | Cl | OMe |
| F | Cl | Me | CF$_3$ | Cl | Me |
| F | Cl | F | CF$_3$ | Cl | F |
| F | Cl | Cl | CF$_3$ | Cl | Cl |
| F | Cl | Br | CF$_3$ | Cl | Br |
| F | Cl | CF$_3$ | CF$_3$ | Cl | CF$_3$ |
| F | Cl | NO$_2$ | CF$_3$ | Cl | NO$_2$ |
| F | Cl | OMe | CF$_3$ | Cl | OMe |
| Cl | Cl | Me | NO$_2$ | Cl | Me |
| Cl | Cl | F | NO$_2$ | Cl | F |
| Cl | Cl | Cl | NO$_2$ | Cl | Cl |
| Cl | Cl | Br | NO$_2$ | Cl | Br |
| Cl | Cl | CF$_3$ | NO$_2$ | Cl | CF$_3$ |
| Cl | Cl | NO$_2$ | NO$_2$ | Cl | NO$_2$ |
| Cl | Cl | OMe | NO$_2$ | Cl | OMe |
| Me | Br | Me | Br | Br | Me |
| Me | Br | F | Br | Br | F |
| Me | Br | Cl | Br | Br | Cl |
| Me | Br | Br | Br | Br | Br |
| Me | Br | CF$_3$ | Br | Br | CF$_3$ |

TABLE 3-continued

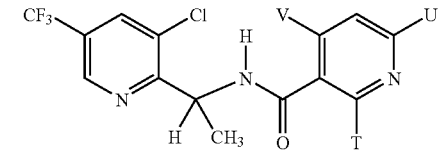

| T | U | V | T | U | V |
|---|---|---|---|---|---|
| Me | Br | NO$_2$ | Br | Br | NO$_2$ |
| Me | Br | OMe | Br | Br | OMe |
| F | Br | Me | CF$_3$ | Br | Me |
| F | Br | F | CF$_3$ | Br | F |
| F | Br | Cl | CF$_3$ | Br | Cl |
| F | Br | Br | CF$_3$ | Br | Br |
| F | Br | CF$_3$ | CF$_3$ | Br | CF$_3$ |
| F | Br | NO$_2$ | CF$_3$ | Br | NO$_2$ |
| F | Br | OMe | CF$_3$ | Br | OMe |
| Cl | Br | Me | NO$_2$ | Br | Me |
| Cl | Br | F | NO$_2$ | Br | F |
| Cl | Br | Cl | NO$_2$ | Br | Cl |
| Cl | Br | Br | NO$_2$ | Br | Br |
| Cl | Br | CF$_3$ | NO$_2$ | Br | CF$_3$ |
| Cl | Br | NO$_2$ | NO$_2$ | Br | NO$_2$ |
| Cl | Br | OMe | NO$_2$ | Br | OMe |
| Me | CF$_3$ | Me | Br | CF$_3$ | Me |
| Me | CF$_3$ | F | Br | CF$_3$ | F |
| Me | CF$_3$ | Cl | Br | CF$_3$ | Cl |
| Me | CF$_3$ | Br | Br | CF$_3$ | Br |
| Me | CF$_3$ | CF$_3$ | Br | CF$_3$ | CF$_3$ |
| Me | CF$_3$ | NO$_2$ | Br | CF$_3$ | NO$_2$ |
| Me | CF$_3$ | OMe | Br | CF$_3$ | OMe |
| F | CF$_3$ | Me | CF$_3$ | CF$_3$ | Me |
| F | CF$_3$ | F | CF$_3$ | CF$_3$ | F |
| F | CF$_3$ | Cl | CF$_3$ | CF$_3$ | Cl |
| F | CF$_3$ | Br | CF$_3$ | CF$_3$ | Br |
| F | CF$_3$ | CF$_3$ | CF$_3$ | CF$_3$ | CF$_3$ |
| F | CF$_3$ | NO$_2$ | CF$_3$ | CF$_3$ | NO$_2$ |
| F | CF$_3$ | OMe | CF$_3$ | CF$_3$ | OMe |
| Cl | CF$_3$ | Me | NO$_2$ | CF$_3$ | Me |
| Cl | CF$_3$ | F | NO$_2$ | CF$_3$ | F |
| Cl | CF$_3$ | Cl | NO$_2$ | CF$_3$ | Cl |
| Cl | CF$_3$ | Br | NO$_2$ | CF$_3$ | Br |
| Cl | CF$_3$ | CF$_3$ | NO$_2$ | CF$_3$ | CF$_3$ |
| Cl | CF$_3$ | NO$_2$ | NO$_2$ | CF$_3$ | NO$_2$ |
| Cl | CF$_3$ | OMe | NO$_2$ | CF$_3$ | OMe |
| Me | NO$_2$ | Me | Br | NO$_2$ | Me |
| Me | NO$_2$ | F | Br | NO$_2$ | F |
| Me | NO$_2$ | Cl | Br | NO$_2$ | Cl |
| Me | NO$_2$ | Br | Br | NO$_2$ | Br |
| Me | NO$_2$ | CF$_3$ | Br | NO$_2$ | CF$_3$ |
| Me | NO$_2$ | NO$_2$ | Br | NO$_2$ | NO$_2$ |
| Me | NO$_2$ | OMe | Br | NO$_2$ | OMe |
| F | NO$_2$ | Me | CF$_3$ | NO$_2$ | Me |
| F | NO$_2$ | F | CF$_3$ | NO$_2$ | F |
| F | NO$_2$ | Cl | CF$_3$ | NO$_2$ | Cl |
| F | NO$_2$ | Br | CF$_3$ | NO$_2$ | Br |
| F | NO$_2$ | CF$_3$ | CF$_3$ | NO$_2$ | CF$_3$ |
| F | NO$_2$ | NO$_2$ | CF$_3$ | NO$_2$ | NO$_2$ |
| F | NO$_2$ | OMe | CF$_3$ | NO$_2$ | OMe |
| Cl | NO$_2$ | Me | NO$_2$ | NO$_2$ | Me |
| Cl | NO$_2$ | F | NO$_2$ | NO$_2$ | F |
| Cl | NO$_2$ | Cl | NO$_2$ | NO$_2$ | Cl |
| Cl | NO$_2$ | Br | NO$_2$ | NO$_2$ | Br |
| Cl | NO$_2$ | CF$_3$ | NO$_2$ | NO$_2$ | CF$_3$ |
| Cl | NO$_2$ | NO$_2$ | NO$_2$ | NO$_2$ | NO$_2$ |
| Cl | NO$_2$ | OMe | NO$_2$ | NO$_2$ | OMe |
| Me | OMe | Me | Br | OMe | Me |
| Me | OMe | F | Br | OMe | F |
| Me | OMe | Cl | Br | OMe | Cl |
| Me | OMe | Br | Br | OMe | Br |
| Me | OMe | CF$_3$ | Br | OMe | CF$_3$ |
| Me | OMe | NO$_2$ | Br | OMe | NO$_2$ |
| Me | OMe | OMe | Br | OMe | OMe |
| F | OMe | Me | CF$_3$ | OMe | Me |
| F | OMe | F | CF$_3$ | OMe | F |
| F | OMe | Cl | CF$_3$ | OMe | Cl |

TABLE 3-continued

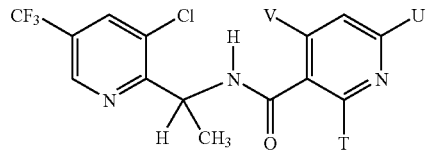

| T | U | V | T | U | V |
|---|---|---|---|---|---|
| F | OMe | Br | CF₃ | OMe | Br |
| F | OMe | CF₃ | CF₃ | OMe | CF₃ |
| F | OMe | NO₂ | CF₃ | OMe | NO₂ |
| F | OMe | OMe | CF₃ | OMe | OMe |
| Cl | OMe | Me | NO₂ | OMe | Me |
| Cl | OMe | F | NO₂ | OMe | F |
| Cl | OMe | Cl | NO₂ | OMe | Cl |
| Cl | OMe | Br | NO₂ | OMe | Br |
| Cl | OMe | CF₃ | NO₂ | OMe | CF₃ |
| Cl | OMe | NO₂ | NO₂ | OMe | NO₂ |
| Cl | OMe | OMe | NO₂ | OMe | OMe |
| Me | H | Me | Br | H | Me |
| Me | H | F | Br | H | F |
| Me | H | Cl | Br | H | Cl |
| Me | H | Br | Br | H | Br |
| Me | H | CF₃ | Br | H | CF₃ |
| Me | H | NO₂ | Br | H | NO₂ |
| Me | H | OMe | Br | H | OMe |
| F | H | Me | CF₃ | H | Me |
| F | H | F | CF₃ | H | F |
| F | H | Cl | CF₃ | H | Cl |
| F | H | Br | CF₃ | H | Br |
| F | H | CF₃ | CF₃ | H | CF₃ |
| F | H | NO₂ | CF₃ | H | NO₂ |
| F | H | OMe | CF₃ | H | OMe |
| Cl | H | Me | NO₂ | H | Me |
| Cl | H | F | NO₂ | H | F |
| Cl | H | Cl | NO₂ | H | Cl |
| Cl | H | Br | NO₂ | H | Br |
| Cl | H | CF₃ | NO₂ | H | CF₃ |
| Cl | H | NO₂ | NO₂ | H | NO₂ |
| Cl | H | OMe | NO₂ | H | OMe |
| OMe | Me | Me | OMe | Br | Me |
| OMe | Me | F | OMe | Br | F |
| OMe | Me | Cl | OMe | Br | Cl |
| OMe | Me | Br | OMe | Br | Br |
| OMe | Me | CF₃ | OMe | Br | CF₃ |
| OMe | Me | NO₂ | OMe | Br | NO₂ |
| OMe | Me | OMe | OMe | Br | OMe |
| OMe | F | Me | OMe | CF₃ | Me |
| OMe | F | F | OMe | CF₃ | F |
| OMe | F | Cl | OMe | CF₃ | Cl |
| OMe | F | Br | OMe | CF₃ | Br |
| OMe | F | CF₃ | OMe | CF₃ | CF₃ |
| OMe | F | NO₂ | OMe | CF₃ | NO₂ |
| OMe | F | OMe | OMe | CF₃ | OMe |
| OMe | Cl | Me | OMe | NO₂ | Me |
| OMe | Cl | F | OMe | NO₂ | F |
| OMe | Cl | Cl | OMe | NO₂ | Cl |
| OMe | Cl | Br | OMe | NO₂ | Br |
| OMe | Cl | CF₃ | OMe | NO₂ | CF₃ |
| OMe | Cl | NO₂ | OMe | NO₂ | NO₂ |
| OMe | Cl | OMe | OMe | NO₂ | OMe |
| OMe | H | Me | OMe | H | Br |
| OMe | H | F | OMe | H | CF₃ |
| OMe | H | Cl | OMe | H | NO₂ |
| OMe | H | OMe | OMe | OMe | Me |
| OMe | OMe | CF₃ | OMe | OMe | F |
| OMe | OMe | NO₂ | OMe | OMe | Cl |
| OMe | OMe | OMe | OMe | OMe | Br |

TABLE 4

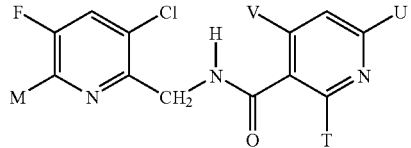

T and V are both Cl and U is H

| Q | R | M | Q | R | M |
|---|---|---|---|---|---|
| Cl | Cl | H | Cl | Cl | Me |
| Cl | Br | H | Cl | Br | Me |
| Cl | OCF₃ | H | Cl | OCF₃ | Me |
| Cl | OCHF₂ | H | Cl | OCHF₂ | Me |
| Cl | OCH₂CF₃ | H | Cl | OCH₂CF₃ | Me |
| Cl | OCF₂CF₃ | H | Cl | OCF₂CF₃ | Me |
| Cl | OCF₂CF₂H | H | Cl | OCF₂CF₂H | Me |
| Cl | OCHFCF₃ | H | Cl | OCHFCF₃ | Me |
| Cl | SCF₃ | H | Cl | SCF₃ | Me |
| Cl | SCHF₂ | H | Cl | SCHF₂ | Me |
| Cl | SCH₂CF₃ | H | Cl | SCH₂CF₃ | Me |
| Cl | SCF₂CF₃ | H | Cl | SCF₂CF₃ | Me |
| Cl | SCF₂CF₂H | H | Cl | SCF₂CF₂H | Me |
| Cl | SCHFCF₃ | H | Cl | SCHFCF₃ | Me |
| Cl | SOCF₃ | H | Cl | SOCF₃ | Me |
| Cl | SOCHF₂ | H | Cl | SOCHF₂ | Me |
| Cl | SOCH₂CF₃ | H | Cl | SOCH₂CF₃ | Me |
| Cl | SOCF₂CF₃ | H | Cl | SOCF₂CF₃ | Me |
| Cl | SOCF₂CF₂H | H | Cl | SOCF₂CF₂H | Me |
| Cl | SOCHFCF₃ | H | Cl | SOCHFCF₃ | Me |
| Cl | SO₂CF₃ | H | Cl | SO₂CF₃ | Me |
| Cl | SO₂CHF₂ | H | Cl | SO₂CHF₂ | Me |
| Cl | SO₂CH₂CF₃ | H | Cl | SO₂CH₂CF₃ | Me |
| Cl | SO₂CF₂CF₃ | H | Cl | SO₂CF₂CF₃ | Me |
| Cl | SO₂CF₂CF₂H | H | Cl | SO₂CF₂CF₂H | Me |
| Cl | SO₂CHFCF₃ | H | Cl | SO₂CHFCF₃ | Me |
| Cl | CN | H | Cl | CN | Me |
| Br | Cl | H | Br | Cl | Me |
| Br | Br | H | Br | Br | Me |
| Br | OCF₃ | H | Br | OCF₃ | Me |
| Br | OCHF₂ | H | Br | OCHF₂ | Me |
| Br | OCH₂CF₃ | H | Br | OCH₂CF₃ | Me |
| Br | OCF₂CF₃ | H | Br | OCF₂CF₃ | Me |
| Br | OCF₂CF₂H | H | Br | OCF₂CF₂H | Me |
| Br | OCHFCF₃ | H | Br | OCHFCF₃ | Me |
| Br | SCF₃ | H | Br | SCF₃ | Me |
| Br | SCHF₂ | H | Br | SCHF₂ | Me |
| Br | SCH₂CF₃ | H | Br | SCH₂CF₃ | Me |
| Br | SCF₂CF₃ | H | Br | SCF₂CF₃ | Me |
| Br | SCF₂CF₂H | H | Br | SCF₂CF₂H | Me |
| Br | SCHFCF₃ | H | Br | SCHFCF₃ | Me |
| Br | SOCF₃ | H | Br | SOCF₃ | Me |
| Br | SOCHF₂ | H | Br | SOCHF₂ | Me |
| Br | SOCH₂CF₃ | H | Br | SOCH₂CF₃ | Me |
| Br | SOCF₂CF₃ | H | Br | SOCF₂CF₃ | Me |
| Br | SOCF₂CF₂H | H | Br | SOCF₂CF₂H | Me |
| Br | SOCHFCF₃ | H | Br | SOCHFCF₃ | Me |
| Br | SO₂CF₃ | H | Br | SO₂CF₃ | Me |
| Br | SO₂CHF₂ | H | Br | SO₂CHF₂ | Me |
| Br | SO₂CH₂CF₃ | H | Br | SO₂CH₂CF₃ | Me |
| Br | SO₂CF₂CF₃ | H | Br | SO₂CF₂CF₃ | Me |
| Br | SO₂CF₂CF₂H | H | Br | SO₂CF₂CF₂H | Me |
| Br | SO₂CHFCF₃ | H | Br | SO₂CHFCF₃ | Me |
| Br | CN | H | Br | CN | Me |

T and V are both Cl and U is Me

| Q | R | S | Q | R | S |
|---|---|---|---|---|---|
| Cl | Cl | H | Cl | Cl | Me |
| Cl | Br | H | Cl | Br | Me |
| Cl | OCF₃ | H | Cl | OCF₃ | Me |
| Cl | OCHF₂ | H | Cl | OCHF₂ | Me |
| Cl | OCH₂CF₃ | H | Cl | OCH₂CF₃ | Me |
| Cl | OCF₂CF₃ | H | Cl | OCF₂CF₃ | Me |
| Cl | OCF₂CF₂H | H | Cl | OCF₂CF₂H | Me |

TABLE 4-continued

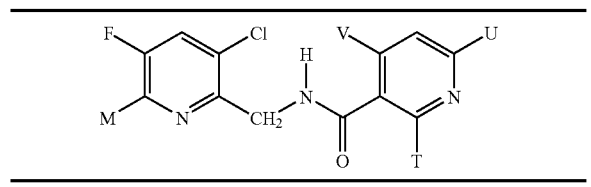

| | | | | | |
|---|---|---|---|---|---|
| Cl | OCHFCF$_3$ | H | Cl | OCHFCF$_3$ | Me |
| Cl | SCF$_3$ | H | Cl | SCF$_3$ | Me |
| Cl | SCHF$_2$ | H | Cl | SCHF$_2$ | Me |
| Cl | SCH$_2$CF$_3$ | H | Cl | SCH$_2$CF$_3$ | Me |
| Cl | SCF$_2$CF$_3$ | H | Cl | SCF$_2$CF$_3$ | Me |
| Cl | SCF$_2$CF$_2$H | H | Cl | SCF$_2$CF$_2$H | Me |
| Cl | SCHFCF$_3$ | H | Cl | SCHFCF$_3$ | Me |
| Cl | SOCF$_3$ | H | Cl | SOCF$_3$ | Me |
| Cl | SOCHF$_2$ | H | Cl | SOCHF$_2$ | Me |
| Cl | SOCH$_2$CF$_3$ | H | Cl | SOCH$_2$CF$_3$ | Me |
| Cl | SOCF$_2$CF$_3$ | H | Cl | SOCF$_2$CF$_3$ | Me |
| Cl | SOCF$_2$CF$_2$H | H | Cl | SOCF$_2$CF$_2$H | Me |
| Cl | SOCHFCF$_3$ | H | Cl | SOCHFCF$_3$ | Me |
| Cl | SO$_2$CF$_3$ | H | Cl | SO$_2$CF$_3$ | Me |
| Cl | SO$_2$C$_2$ | H | Cl | SO$_2$CH$_2$ | Me |
| Cl | SO$_2$CH$_2$CF$_3$ | H | Cl | SO$_2$CH$_2$CF$_3$ | Me |
| Cl | SO$_2$CF$_2$CF$_3$ | H | Cl | SO$_2$CF$_2$CF$_3$ | Me |
| Cl | SO$_2$CF$_2$CF$_2$H | H | Cl | SO$_2$CF$_2$CF$_2$H | Me |
| Cl | SO$_2$CHFCF$_3$ | H | Cl | SO$_2$CHFCF$_3$ | Me |
| Cl | CN | H | Cl | CN | Me |
| Br | Cl | H | Br | Cl | Me |
| Br | Br | H | Br | Br | Me |
| Br | OCF$_3$ | H | Br | OCF$_3$ | Me |
| Br | OCHF$_2$ | H | Br | OCHF$_2$ | Me |
| Br | OCH$_2$CF$_3$ | H | Br | OCH$_2$CF$_3$ | Me |
| Br | OCF$_2$CF$_3$ | H | Br | OCF$_2$CF$_3$ | Me |
| Br | OCF$_2$CF$_2$H | H | Br | OCF$_2$CF$_2$H | Me |
| Br | OCHFCF$_3$ | H | Br | OCHFCF$_3$ | Me |
| Br | SCF$_3$ | H | Br | SCF$_3$ | Me |
| Br | SCHF$_2$ | H | Br | SCHF$_2$ | Me |
| Br | SCH$_2$CF$_3$ | H | Br | SCH$_2$CF$_3$ | Me |
| Br | SCF$_2$CF$_3$ | H | Br | SCF$_2$CF$_3$ | Me |
| Br | SCF$_2$CF$_2$H | H | Br | SCF$_2$CF$_2$H | Me |
| Br | SCHFCF$_3$ | H | Br | SCHFCF$_3$ | Me |
| Br | SOCF$_3$ | H | Br | SOCF$_3$ | Me |
| Br | SOCHF$_2$ | H | Br | SOCHF$_2$ | Me |
| Br | SOCH$_2$CF$_3$ | H | Br | SOCH$_2$CF$_3$ | Me |
| Br | SOCF$_2$CF$_3$ | H | Br | SOCF$_2$CF$_3$ | Me |
| Br | SOCF$_2$CF$_2$H | H | Br | SOCF$_2$CF$_2$H | Me |
| Br | SOCHFCF$_3$ | H | Br | SOCHFCF$_3$ | Me |
| Br | SO$_2$CF$_3$ | H | Br | SO$_2$CF$_3$ | Me |
| Br | SO$_2$CHF$_2$ | H | Br | SO$_2$CHF$_2$ | Me |
| Br | SO$_2$CH$_2$CF$_3$ | H | Br | SO$_2$CH$_2$CF$_3$ | Me |
| Br | SO$_2$CF$_2$CF$_3$ | H | Br | SO$_2$CF$_2$CF$_3$ | Me |
| Br | SO$_2$CF$_2$CF$_2$H | H | Br | SO$_2$CF$_2$CF$_2$H | Me |
| Br | SO$_2$CHFCF$_3$ | H | Br | SO$_2$CHFCF$_3$ | Me |
| Br | CN | H | Br | CN | Me |
| T is Cl and V and U are both Me | | | | | |
| Cl | Cl | H | Cl | Cl | Me |
| Cl | Br | H | Cl | Br | Me |
| Cl | OCF$_3$ | H | Cl | OCF$_3$ | Me |
| Cl | OCHF$_2$ | H | Cl | OCHF$_2$ | Me |
| Cl | OCH$_2$CF$_3$ | H | Cl | OCH$_2$CF$_3$ | Me |
| Cl | OCF$_2$CF$_3$ | H | Cl | OCF$_2$CF$_3$ | Me |
| Cl | OCF$_2$CF$_2$H | H | Cl | OCF$_2$CF$_2$H | Me |
| Cl | OCHFCF$_3$ | H | Cl | OCHFCF$_3$ | Me |
| Cl | SCF$_3$ | H | Cl | SCF$_3$ | Me |
| Cl | SCHF$_2$ | H | Cl | SCHF$_2$ | Me |
| Cl | SCH$_2$CF$_3$ | H | Cl | SCH$_2$CF$_3$ | Me |
| Cl | SCF$_2$CF$_3$ | H | Cl | SCF$_2$CF$_3$ | Me |
| Cl | SCF$_2$CF$_2$H | H | Cl | SCF$_2$CF$_2$H | Me |
| Cl | SCHFCF$_3$ | H | Cl | SCHFCF$_3$ | Me |
| Cl | SOCF$_3$ | H | Cl | SOCF$_3$ | Me |
| Cl | SOCHF$_2$ | H | Cl | SOCHF$_2$ | Me |
| Cl | SOCH$_2$CF$_3$ | H | Cl | SOCH$_2$CF$_3$ | Me |
| Cl | SOCF$_2$CF$_3$ | H | Cl | SOCF$_2$CF$_3$ | Me |
| Cl | SOCF$_2$CF$_2$H | H | Cl | SOCF$_2$CF$_2$H | Me |
| Cl | SOCHFCF$_3$ | H | Cl | SOCHFCF$_3$ | Me |
| Cl | SO$_2$CF$_3$ | H | Cl | SO$_2$CF$_3$ | Me |

TABLE 4-continued

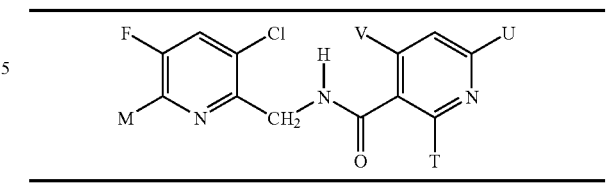

| | | | | | |
|---|---|---|---|---|---|
| Cl | SO$_2$CHF$_2$ | H | Cl | SO$_2$CHF$_2$ | Me |
| Cl | SO$_2$CH$_2$CF$_3$ | H | Cl | SO$_2$CH$_2$CF$_3$ | Me |
| Cl | SO$_2$CF$_2$CF$_3$ | H | Cl | SO$_2$CF$_2$CF$_3$ | Me |
| Cl | SO$_2$CF$_2$CF$_2$H | H | Cl | SO$_2$CF$_2$CF$_2$H | Me |
| Cl | SO$_2$CHFCF$_3$ | H | Cl | SO$_2$CHFCF$_3$ | Me |
| Cl | CN | H | Cl | CN | Me |
| Br | Cl | H | Br | Cl | Me |
| Br | Br | H | Br | Br | Me |
| Br | OCF$_3$ | H | Br | OCF$_3$ | Me |
| Br | OCHF$_2$ | H | Br | OCHF$_2$ | Me |
| Br | OCH$_2$CF$_3$ | H | Br | OCH$_2$CF$_3$ | Me |
| Br | OCF$_2$CF$_3$ | H | Br | OCF$_2$CF$_3$ | Me |
| Br | OCF$_2$CF$_2$H | H | Br | OCF$_2$CF$_2$H | Me |
| Br | OCHFCF$_3$ | H | Br | OCHFCF$_3$ | Me |
| Br | SCF$_3$ | H | Br | SCF$_3$ | Me |
| Br | SCHF$_2$ | H | Br | SCHF$_2$ | Me |
| Br | SCH$_2$CF$_3$ | H | Br | SCH$_2$CF$_3$ | Me |
| Br | SCF$_2$CF$_3$ | H | Br | SCF$_2$CF$_3$ | Me |
| Br | SCF$_2$CF$_2$H | H | Br | SCF$_2$CF$_2$H | Me |
| Br | SCHFCF$_3$ | H | Br | SCHFCF$_3$ | Me |
| Br | SOCF$_3$ | H | Br | SOCF$_3$ | Me |
| Br | SOCHF$_2$ | H | Br | SOCHF$_2$ | Me |
| Br | SOCH$_2$CF$_3$ | H | Br | SOCH$_2$CF$_3$ | Me |
| Br | SOCF$_2$CF$_3$ | H | Br | SOCF$_2$CF$_3$ | Me |
| Br | SOCF$_2$CF$_2$H | H | Br | SOCF$_2$CF$_2$H | Me |
| Br | SOCHFCF$_3$ | H | Br | SOCHFCF$_3$ | Me |
| Br | SO$_2$CF$_3$ | H | Br | SO$_2$CF$_3$ | Me |
| Br | SO$_2$CHF$_2$ | H | Br | SO$_2$CHF$_2$ | Me |
| Br | SO$_2$CH$_2$CF$_3$ | H | Br | SO$_2$CH$_2$CF$_3$ | Me |
| Br | SO$_2$CF$_2$CF$_3$ | H | Br | SO$_2$CF$_2$CF$_3$ | Me |
| Br | SO$_2$CF$_2$CF$_2$H | H | Br | SO$_2$CF$_2$CF$_2$H | Me |
| Br | SO$_2$CHFCF$_3$ | H | Br | SO$_2$CHFCF$_3$ | Me |
| Br | CN | H | Br | CN | Me |

TABLE 5

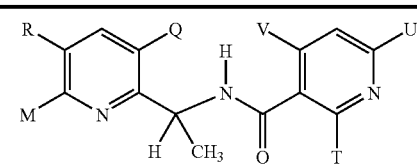

T and V are both Cl and U is H

| Q | R | M | Q | R | M |
|---|---|---|---|---|---|
| Cl | Cl | H | Cl | Cl | Me |
| Cl | Br | H | Cl | Br | Me |
| Cl | OCF$_3$ | H | Cl | OCF$_3$ | Me |
| Cl | OCHF$_2$ | H | Cl | OCHF$_2$ | Me |
| Cl | OCH$_2$CF$_3$ | H | Cl | OCH$_2$CF$_3$ | Me |
| Cl | OCF$_2$CF$_3$ | H | Cl | OCF$_2$CF$_3$ | Me |
| Cl | OCF$_2$CF$_2$ | H | Cl | OCF$_2$CF$_2$H | Me |
| Cl | OCHFCF$_3$ | H | Cl | OCHFCF$_3$ | Me |
| Cl | SCF$_3$ | H | Cl | SCF$_3$ | Me |
| Cl | SCHF$_2$ | H | Cl | SCHF$_2$ | Me |
| Cl | SCH$_2$CF$_3$ | H | Cl | SCH$_2$CF$_3$ | Me |
| Cl | SCF$_2$CF$_3$ | H | Cl | SCF$_2$CF$_3$ | Me |
| Cl | SCF$_2$CF$_2$ | H | Cl | SCF$_2$CF$_2$H | Me |
| Cl | SCHFCF$_3$ | H | Cl | SCHFCF$_3$ | Me |
| Cl | SOCF$_3$ | H | Cl | SOCF$_3$ | Me |
| Cl | SOCHF$_2$ | H | Cl | SOCHF$_2$ | Me |
| Cl | SOCH$_2$CF$_3$ | H | Cl | SOCH$_2$CF$_3$ | Me |
| Cl | SOCF$_2$CF$_3$ | H | Cl | SOCF$_2$CF$_3$ | Me |
| Cl | SOCF$_2$CF$_2$H | H | Cl | SOCF$_2$CF$_2$H | Me |
| Cl | SOCHFCF$_3$ | H | Cl | SOCHFCF$_3$ | Me |

TABLE 5-continued

![Structure with R, Q, M, N on left pyridine ring connected via NH-CH(CH3)-C(=O) to right pyridine ring with V, U, T]

| | | | | | |
|---|---|---|---|---|---|
| Cl | SO2CF3 | H | Cl | SO2CF3 | Me |
| Cl | SO2CHF2 | H | Cl | SO2CHF2 | Me |
| Cl | SO2CH2CF3 | H | Cl | SO2CH2CF3 | Me |
| Cl | SO2CF2CF3 | H | Cl | SO2CF2CF3 | Me |
| Cl | SO2CF2CF2H | H | Cl | SO2CF2CF2H | Me |
| Cl | SO2CHFCF3 | H | Cl | SO2CHFCF3 | Me |
| Cl | CN | H | Cl | CN | Me |
| Br | Cl | H | Br | Cl | Me |
| Br | Br | H | Br | Br | Me |
| Br | OCF3 | H | Br | OCF3 | Me |
| Br | OCHF2 | H | Br | OCHF2 | Me |
| Br | OCH2CF3 | H | Br | OCH2CF3 | Me |
| Br | OCF2CF3 | H | Br | OCF2CF3 | Me |
| Br | OCF2CF2H | H | Br | OCF2CF2H | Me |
| Br | OCHFCF3 | H | Br | OCHFCF3 | Me |
| Br | SCF3 | H | Br | SCF3 | Me |
| Br | SCHF2 | H | Br | SCHF2 | Me |
| Br | SCH2CF3 | H | Br | SCH2CF3 | Me |
| Br | SCF2CF3 | H | Br | SCF2CF3 | Me |
| Br | SCF2CF2H | H | Br | SCF2CF2H | Me |
| Br | SCHFCF3 | H | Br | SCHFCF3 | Me |
| Br | SOCF3 | H | Br | SOCF3 | Me |
| Br | SOCHF2 | H | Br | SOCHF2 | Me |
| Br | SOCH2CF3 | H | Br | SOCH2CF3 | Me |
| Br | SOCF2CF3 | H | Br | SOCF2CF3 | Me |
| Br | SOCF2CF2H | H | Br | SOCF2CF2H | Me |
| Br | SOCHFCF3 | H | Br | SOCHFCF3 | Me |
| Br | SO2CF3 | H | Br | SO2CF3 | Me |
| Br | SO2CHF2 | H | Br | SO2CHF2 | Me |
| Br | SO2CH2CF3 | H | Br | SO2CH2CF3 | Me |
| Br | SO2CF2CF3 | H | Br | SO2CF2CF3 | Me |
| Br | SO2CF2CF2H | H | Br | SO2CF2CF2H | Me |
| Br | SO2CHFCF3 | H | Br | SO2CHFCF3 | Me |
| Br | CN | H | Br | CN | Me |

T and V are both Cl and U is Me

| Q | R | S | Q | R | S |
|---|---|---|---|---|---|
| Cl | Cl | H | Cl | Cl | Me |
| Cl | Br | H | Cl | Br | Me |
| Cl | OCF3 | H | Cl | OCF3 | Me |
| Cl | OCHF2 | H | Cl | OCHF3 | Me |
| Cl | OCH2CF3 | H | Cl | OCH2CF3 | Me |
| Cl | OCF2CF3 | H | Cl | OCF2CF3 | Me |
| Cl | OCF2CF2H | H | Cl | OCF2CF2H | Me |
| Cl | OCHFCF3 | H | Cl | OCHFCF3 | Me |
| Cl | SCF3 | H | Cl | SCF3 | Me |
| Cl | SCHF2 | H | Cl | SCHF2 | Me |
| Cl | SCH2CF3 | H | Cl | SCH2CF3 | Me |
| Cl | SCF2CF3 | H | Cl | SCF2CF3 | Me |
| Cl | SCF2CF2H | H | Cl | SCF2CF2H | Me |
| Cl | SCHFCF3 | H | Cl | SCHFCF3 | Me |
| Cl | SOCF3 | H | Cl | SOCF3 | Me |
| Cl | SOCHF2 | H | Cl | SOCHF2 | Me |
| Cl | SOCH2CF3 | H | Cl | SOCH2CF3 | Me |
| Cl | SOCF2CF3 | H | Cl | SOCF2CF3 | Me |
| Cl | SOCF2CF2H | H | Cl | SOCF2CF2H | Me |
| Cl | SOCHFCF3 | H | Cl | SOCHFCF3 | Me |
| Cl | SO2CF3 | H | Cl | SO2CF3 | Me |
| Cl | SO2CHF2 | H | Cl | SO2CHF2 | Me |
| Cl | SO2CH2CF3 | H | Cl | SO2CH2CF3 | Me |
| Cl | SO2CF2CF3 | H | Cl | SO2CF2CF3 | Me |
| Cl | SO2CF2CF2H | H | Cl | SO2CF2CF2H | Me |
| Cl | SO2CHFCF3 | H | Cl | SO2CHFCF3 | Me |
| Cl | CN | H | Cl | CN | Me |
| Br | Cl | H | Br | Cl | Me |
| Br | Br | H | Br | Br | Me |
| Br | OCF3 | H | Br | OCF3 | Me |
| Br | OCHF2 | H | Br | OCHF2 | Me |
| Br | OCH2CF3 | H | Br | OCH2CF3 | Me |
| Br | OCF2CF3 | H | Br | OCF2CF3 | Me |
| Br | OCF2CF2H | Cl | Br | OCF2CF H | Me |
| Br | OCHFCF3 | H | Br | OCHFCF3 | Me |
| Br | SCF3 | H | Br | SCF3 | Me |
| Br | SCHF2 | H | Br | SCHF2 | Me |
| Br | SCH2CF3 | H | Br | SCH2CF3 | Me |
| Br | SCF2CF3 | H | Br | SCF2CF3 | Me |
| Br | SCF2CF2H | H | Br | SCF2CF2H | Me |
| Br | SCHFCF3 | H | Br | SCHFCF3 | Me |
| Br | SOCF3 | H | Br | SOCF3 | Me |
| Br | SOCHF2 | H | Br | SOCHF2 | Me |
| Br | SOCH2CF3 | H | Br | SOCH2CF3 | Me |
| Br | SOCF2CF3 | H | Br | SOCF2CF3 | Me |
| Br | SOCF2CF2H | H | Br | SOCF2CF2H | Me |
| Br | SOCHFCF3 | H | Br | SOCHFCF3 | Me |
| Br | SO2CF3 | H | Br | SO2CF3 | Me |
| Br | SO2CHF2 | H | Br | SO2CHF2 | Me |
| Br | SO2CH2CF3 | H | Br | SO2CH2CF3 | Me |
| Br | SO2CF2CF3 | H | Br | SO2CF2CF3 | Me |
| Br | SO2CF2CF2H | H | Br | SO2CF2CF2H | Me |
| Br | SO2CHFCF3 | H | Br | SO2CHFCF3 | Me |
| Br | CN | H | Br | CN | Me |

T is Cl and V and U are both Me

| Cl | Cl | H | Cl | Cl | Me |
| Cl | Br | H | Cl | Br | Me |
| Cl | OCF3 | H | Cl | OCF3 | Me |
| Cl | OCHF2 | H | Cl | OCHF3 | Me |
| Cl | OCH2CF3 | H | Cl | OCH2CF3 | Me |
| Cl | OCF2CF3 | H | Cl | OCF2CF3 | Me |
| Cl | OCF2CF2H | H | Cl | OCF2CF2H | Me |
| Cl | OCHFCF3 | H | Cl | OCHFCF3 | Me |
| Cl | SCF3 | H | Cl | SCF3 | Me |
| Cl | SCHF2 | H | Cl | SCHF2 | Me |
| Cl | SCH2CF3 | H | Cl | SCH2CF3 | Me |
| Cl | SCF2CF3 | H | Cl | SCF2CF3 | Me |
| Cl | SCF2CF2H | H | Cl | SCF2CF2H | Me |
| Cl | SCHFCF3 | H | Cl | SCHFCF3 | Me |
| Cl | SOCF3 | H | Cl | SOCF3 | Me |
| Cl | SOCHF2 | H | Cl | SOCHF2 | Me |
| Cl | SOCH2CF3 | H | Cl | SOCH2CF3 | Me |
| Cl | SOCF2CF3 | H | Cl | SOCF2CF3 | Me |
| Cl | SOCF2CF2H | H | Cl | SOCF2CF2H | Me |
| Cl | SOCHFCF3 | H | Cl | SOCHFCF3 | Me |
| Cl | SO2CF3 | H | Cl | SO2CF3 | Me |
| Cl | SO2CHF2 | H | Cl | SO2CHF2 | Me |
| Cl | SO2CH2CF3 | H | Cl | SO2CH2CF3 | Me |
| Cl | SO2CF2CF3 | H | Cl | SO2CF2CF3 | Me |
| Cl | SO2CF2CF2H | H | Cl | SO2CF2CF2H | Me |
| Cl | SO2CHFCF3 | H | Cl | SO2CHFCF3 | Me |
| Cl | CN | H | Cl | CN | Me |
| Br | Cl | H | Br | Cl | Me |
| Br | Br | H | Br | Br | Me |
| Br | OCF3 | H | Br | OCF3 | Me |
| Br | OCHF2 | H | Br | OCHF2 | Me |
| Br | OCH2CF3 | H | Br | OCH2CF3 | Me |
| Br | OCF2CF3 | H | Br | OCF2CF3 | Me |
| Br | OCF2CF2H | H | Br | OCF2CF2H | Me |
| Br | OCHFCF3 | H | Br | OCHFCF3 | Me |
| Br | SCF3 | H | Br | SCF3 | Me |
| Br | SCHF2 | H | Br | SCHF2 | Me |
| Br | SCH2CF3 | H | Br | SCH2CF3 | Me |
| Br | SCF2CF3 | H | Br | SCF2CF3 | Me |
| Br | SCF2CF2H | H | Br | SCF2CF2H | Me |
| Br | SCHFCF3 | H | Br | SCHFCF3 | Me |
| Br | SOCF3 | H | Br | SOCF3 | Me |
| Br | SOCHF2 | H | Br | SOCHF2 | Me |
| Br | SOCH2CF3 | H | Br | SOCH2CF3 | Me |
| Br | SOCF2CF3 | H | Br | SOCF2CF3 | Me |

TABLE 5-continued

Structure: pyridine with R, Q, M substituents, connected via -CH(CH3)-NH-C(=O)- to another pyridine with V, U, T substituents.

| | | | | | |
|---|---|---|---|---|---|
| Br | SOCF₂CF₂H | H | Br | SOCF₂CF₂H | Me |
| Br | SOCHFCF₃ | H | Br | SOCHFCF₃ | Me |
| Br | SO₂CF₃ | H | Br | SO₂CF₃ | Me |
| Br | SO₂CHF₂ | H | Br | SO₂CHF₂ | Me |
| Br | SO₂CH₂CF₃ | H | Br | SO₂CH₂CF₃ | Me |
| Br | SO₂CF₂CF₃ | H | Br | SO₂CF₂CF₃ | Me |
| Br | SO₂CF₂CF₂H | H | Br | SO₂CF₂CF₂H | Me |
| Br | SO₂CHFCF₃ | H | Br | SO₂CHFCF₃ | Me |
| Br | CN | H | Br | CN | Me |

TABLE 6

Structure: pyridine with R, Q, M substituents, connected via -CH₂-NH-C(=O)- to another pyridine with V, U, T substituents.

T and V are both Cl and U is H

| Q | R | M | Q | R | M |
|---|---|---|---|---|---|
| Cl | Cl | H | Cl | Cl | Me |
| Cl | Br | H | Cl | Br | Me |
| Cl | CF₃ | H | Cl | CF₃ | Me |
| Cl | OCF₃ | H | Cl | OCF₃ | Me |
| Cl | OCHF₂ | H | Cl | OCHF₂ | Me |
| Cl | OCH₂CF₃ | H | Cl | OCH₂CF₃ | Me |
| Cl | OCF₂CF₃ | H | Cl | OCF₂CF₃ | Me |
| Cl | OCF₂CF₂H | H | Cl | OCF₂CF₂H | Me |
| Cl | OCHFCF₃ | H | Cl | OCHFCF₃ | Me |
| Cl | SCF₃ | H | Cl | SCF₃ | Me |
| Cl | SCHF₂ | H | Cl | SCHF₂ | Me |
| Cl | SCH₂CF₃ | H | Cl | SCH₂CF₃ | Me |
| Cl | SCF₂CF₃ | H | Cl | SCF₂CF₃ | Me |
| Cl | SCF₂CF₂H | H | Cl | SCF₂CF₂H | Me |
| Cl | SCHFCF₃ | H | Cl | SCHFCF₃ | Me |
| Cl | SOCF₃ | H | Cl | SOCF₃ | Me |
| Cl | SOCHF₂ | H | Cl | SOCHF₂ | Me |
| Cl | SOCH₂CF₃ | H | Cl | SOCH₂CF₃ | Me |
| Cl | SOCF₂CF₃ | H | Cl | SOCF₂CF₃ | Me |
| Cl | SOCF₂CF₂H | H | Cl | SOCF₂CF₂H | Me |
| Cl | SOCHFCF₃ | H | Cl | SOCHFCF₃ | Me |
| Cl | SO₂CF₃ | H | Cl | SO₂CF₃ | Me |
| Cl | SO₂CHF₂ | H | Cl | SO₂CHF₂ | Me |
| Cl | SO₂CH₂CF₃ | H | Cl | SO₂CH₂CF₃ | Me |
| Cl | SO₂CF₂CF₃ | H | Cl | SO₂CF₂CF₃ | Me |
| Cl | SO₂CF₂CF₂H | H | Cl | SO₂CF₂CF₂H | Me |
| Cl | SO₂CHFCF₃ | H | Cl | SO₂CHFCF₃ | Me |
| Cl | CN | H | Cl | CN | Me |
| Cl | H | Cl | Cl | Me | Cl |
| Cl | H | Br | Cl | Me | Br |
| Cl | H | CF₃ | Cl | Me | CF₃ |
| Cl | H | OCF₃ | Cl | Me | OCF₃ |
| Cl | H | OCHF₂ | Cl | Me | OCHF₂ |
| Cl | H | OCH₂CF₃ | Cl | Me | OCH₂CF₃ |
| Cl | H | OCF₂CF₂H | Cl | Me | OCF₂CF₂H |
| Cl | H | SCF₃ | Cl | Me | SCF₃ |
| Cl | H | SCHF₂ | Cl | Me | SCHF₂ |
| Br | Cl | H | Br | Cl | Me |
| Br | Br | H | Br | Br | Me |
| Br | CF₃ | H | Br | CF₃ | Me |
| Br | OCF₃ | H | Br | OCF₃ | Me |
| Br | OCHF₂ | H | Br | OCHF₂ | Me |
| Br | OCH₂CF₃ | H | Br | OCH₂CF₃ | Me |
| Br | OCF₂CF₃ | H | Br | OCF₂CF₃ | Me |

TABLE 6-continued

| | | | | | |
|---|---|---|---|---|---|
| Br | OCF₂CF₂H | H | Br | OCF₂CF₂H | Me |
| Br | OCHFCF₃ | H | Br | OCHFCF₃ | Me |
| Br | SCF₃ | H | Br | SCF₃ | Me |
| Br | SCHF₂ | H | Br | SCHF₂ | Me |
| Br | SCH₂CF₃ | H | Br | SCH₂CF₃ | Me |
| Br | SCF₂CF₃ | H | Br | SCF₂CF₃ | Me |
| Br | SCF₂CF₂H | H | Br | SCF₂CF₂H | Me |
| Br | SCHFCF₃ | H | Br | SCHFCF₃ | Me |
| Br | SOCF₃ | H | Br | SOCF₃ | Me |
| Br | SOCHF₂ | H | Br | SOCHF₂ | Me |
| Br | SOCH₂CF₃ | H | Br | SOCH₂CF₃ | Me |
| Br | SOCF₂CF₃ | H | Br | SOCF₂CF₃ | Me |
| Br | SOCF₂CF₂H | H | Br | SOCF₂CF₂H | Me |
| Br | SOCHFCF₃ | H | Br | SOCHFCF₃ | Me |
| Br | SO₂CF₃ | H | Br | SO₂CF₃ | Me |
| Br | SO₂CHF₂ | H | Br | SO₂CHF₂ | Me |
| Br | SO₂CH₂CF₃ | H | Br | SO₂CH₂CF₃ | Me |
| Br | SO₂CF₂CF₃ | H | Br | SO₂CF₂CF₃ | Me |
| Br | SO9 CF₂CF₂H | H | Br | SO₂CF₂CF₂H | Me |
| Br | SO₂CHFCF₃ | H | Br | SO₂CHFCF₃ | Me |
| Br | CN | H | Br | CN | Me |
| H | Cl | Cl | Me | Cl | Cl |
| H | Br | Cl | Me | Br | Cl |
| H | CF₃ | Cl | Me | CF₃ | Cl |
| H | OCF₃ | Cl | Me | OCF₃ | Cl |
| H | OCHF₂ | Cl | Me | OCHF₂ | Cl |
| H | OCH₂CF₃ | Cl | Me | OCH₂CF₃ | Cl |
| H | OCF₂CF₃ | Cl | Me | OCF₂CF₃ | Cl |
| H | OCF₂CF₂H | Cl | Me | OCF₂CF₂H | Cl |
| H | OCHFCF₃ | Cl | Me | OCHFCF₃ | Cl |
| H | SCF₃ | Cl | Me | SCF₃ | Cl |
| H | SCHF₂ | Cl | Me | SCHF₂ | Cl |
| H | SCH₂CF₃ | Cl | Me | SCH₂CF₃ | Cl |
| H | SCF₂CF₃ | Cl | Me | SCF₂CF₃ | Cl |
| H | SCF₂CF₂H | Cl | Me | SCF₂CF₂H | Cl |
| H | SCHFCF₃ | Cl | Me | SCHFCF₃ | Cl |
| H | SOCF₃ | Cl | Me | SOCF₃ | Cl |
| H | SOCHF₂ | Cl | Me | SOCHF₂ | Cl |
| H | SOCH₂CF₃ | Cl | Me | SOCH₂CF₃ | Cl |
| H | SOCF₂CF₃ | Cl | Me | SOCF₂CF₃ | Cl |
| H | SOCF₂CF₂H | Cl | Me | SOCF₂CF₂H | Cl |
| H | SOCHFCF₃ | Cl | Me | SOCHFCF₃ | Cl |
| H | SO₂CF₃ | Cl | Me | SO₂CF₃ | Cl |
| H | SO₂CHF₂ | Cl | Me | SO₂CHF₂ | Cl |
| H | SO₂CH₂CF₃ | Cl | Me | SO₂CH₂CF₃ | Cl |
| H | SO₂CF₂CF₃ | Cl | Me | SO₂CF₂CF₃ | Cl |
| H | SO₂CF₂CF₂H | Cl | Me | SO₂CF₂CF₂H | Cl |
| H | SO₂CHFCF₃ | Cl | Me | SO₂CHFCF₃ | Cl |
| H | CN | Cl | Me | CN | Cl |
| Cl | Cl | H | Cl | Cl | Me |
| Cl | Br | H | Cl | Br | Me |
| Cl | CF₃ | H | Cl | CF₃ | Me |
| Cl | OCF₃ | H | Cl | OCF₃ | Me |
| Cl | OCHF₂ | H | Cl | OCHF₂ | Me |
| Cl | OCH₂CF₃ | H | Cl | OCH₂CF₃ | Me |
| Cl | OCF₂CF₃ | H | Cl | OCF₂CF₃ | Me |
| Cl | OCF₂CF₂H | H | Cl | OCF₂CF₂H | Me |
| Cl | OCFCF₃ | H | Cl | OCHFCF₃ | Me |
| Cl | SCF₃ | H | Cl | SCF₃ | Me |
| Cl | SCHF₂ | H | Cl | SCHF₂ | Me |
| Cl | SCH₂CF₃ | H | Cl | SCH₂CF₃ | Me |
| Cl | SCF₂CF₃ | H | Cl | SCF₂CF₃ | Me |
| Cl | SCF₂CF₂H | H | Cl | SCF₂CF₂H | Me |
| Cl | SCHFCF₃ | H | Cl | SCHFCF₃ | Me |
| Cl | SOCF₃ | H | Cl | SOCF₃ | Me |
| Cl | SOCHF₂ | H | Cl | SOCHF₂ | Me |
| Cl | SOCH₂CF₃ | H | Cl | SOCH₂CF₃ | Me |
| Cl | SOCF₂CF₃ | H | Cl | SOCF₂CF₃ | Me |
| Cl | SOCF₂CF₂H | H | Cl | SOCF₂CF₂H | Me |
| Cl | SOCHFCF₃ | H | Cl | SOCHFCF₃ | Me |

TABLE 6-continued

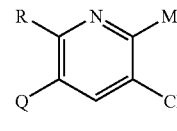

| | | | | | |
|---|---|---|---|---|---|
| Cl | SO₂CF₃ | H | Cl | SO₂CF₃ | Me |
| Cl | SO₂CHF₂ | H | Cl | SO₂CHF₂ | Me |
| Cl | SO₂CH₂CF₃ | H | Cl | SO₂CH₂CF₃ | Me |
| Cl | SO₂CF₂CF₃ | H | Cl | SO₂CF₂CF₃ | Me |
| Cl | SO₂CF₂CF₂H | H | Cl | SO₂CF₂CF₂H | Me |
| Cl | SO₂CHFCF₃ | H | Cl | SO₂CHFCF₃ | Me |
| Cl | CN | H | Cl | CN | Me |
| Cl | H | Cl | Cl | Me | Cl |
| Cl | H | Br | Cl | Me | Br |
| Cl | H | CF₃ | Cl | Me | CF₃ |
| Cl | H | OCF₃ | Cl | Me | OCF₃ |
| Cl | H | OCHF₂ | Cl | Me | OCHF₂ |
| Cl | H | OCH₂CF₃ | Cl | Me | OCH₂CF₃ |
| Cl | H | OCF₂CF₂H | Cl | Me | OCF₂CF₂H |
| Cl | H | SCF₃ | Cl | Me | SCF₃ |
| Cl | H | SCHF₂ | Cl | Me | SCHF₂ |
| Br | SCF₃ | H | Br | SCF₃ | Me |
| Br | SCHF₂ | H | Br | SCHF₂ | Me |
| Br | SCH₂CF₃ | H | Br | SCH₂CF₃ | Me |
| Br | SCF₂CF₃ | H | Br | SCF₂CF₃ | Me |
| Br | SCF₂CF₂H | H | Br | SCF₂CF₂H | Me |
| Br | SCHFCF₃ | H | Br | SCHFCF₃ | Me |
| Br | SOCF₃ | H | Br | SOCF₃ | Me |
| Br | SOCHF₂ | H | Br | SOCHF₂ | Me |
| Br | SOCH₂CF₃ | H | Br | SOCH₂CF₃ | Me |
| Br | SOCF₂CF₃ | H | Br | SOCF₂CF₃ | Me |
| Br | SOCF₂CF₂H | H | Br | SOCF₂CF₂H | Me |
| Br | SOCHFCF₃ | H | Br | SOCHFCF₃ | Me |
| Br | SO₂CF₃ | H | Br | SO₂CF₃ | Me |
| Br | SO₂CHF₂ | H | Br | SO₂CHF₂ | Me |
| Br | SO₂CH₂CF₃ | H | Br | SO₂CH₂CF₃ | Me |
| Br | SO₂CF₂CF₃ | H | Br | SO₂CF₂CF₃ | Me |
| Br | SO₂CF₂CF₂H | H | Br | SO₂CF₂CF₂H | Me |
| Br | SO₂CHFCF₃ | H | Br | SO₂CHFCF₃ | Me |
| Br | CN | H | Br | CN | Me |
| H | Cl | Cl | Me | Cl | Cl |
| H | Br | Cl | Me | Br | Cl |
| H | CF₃ | Cl | Me | CF₃ | Cl |
| H | OCF₃ | Cl | Me | OCF₃ | Cl |
| H | OCHF₂ | Cl | Me | OCHF₂ | Cl |
| H | OCH₂CF₃ | Cl | Me | OCH₂CF₃ | Cl |
| H | OCF₂CF₃ | Cl | Me | OCF₂CF₃ | Cl |
| H | OCF₂CF₂H | Cl | Me | OCF₂CF₂H | Cl |
| H | OCHFCF₃ | Cl | Me | OCHFCF₃ | Cl |
| H | SCF₃ | Cl | Me | SCF₃ | Cl |
| H | SCHF₂ | Cl | Me | SCHF₂ | Cl |
| H | SCH₂CF₃ | Cl | Me | SCH₂CF₃ | Cl |
| H | SCF₂CF₃ | Cl | Me | SCF₂CF₃ | Cl |
| H | SCF₂CF₂H | Cl | Me | SCF₂CF₂H | Cl |
| H | SCHFCF₃ | Cl | Me | SCHFCF₃ | Cl |
| H | SOCF₃ | Cl | Me | SOCF₃ | Cl |
| H | SOCHF₂ | Cl | Me | SOCHF₂ | Cl |
| H | SOCH₂CF₃ | Cl | Me | SOCH₂CF₃ | Cl |
| H | SOCF₂CF₃ | Cl | Me | SOCF₂CF₃ | Cl |
| H | SOCF₂CF₂H | Cl | Me | SOCF₂CF₂H | Cl |
| H | SOCHFCF₃ | Cl | Me | SOCHFCF₃ | Cl |
| H | SO₂CF₃ | Cl | Me | SO₂CF₃ | Cl |
| H | SO₂CHF₂ | Cl | Me | SO₂CHF₂ | Cl |
| H | SO₂CH₂CF₃ | Cl | Me | SO₂CH₂CF₃ | Cl |
| H | SO₂CF₂CF₃ | Cl | Me | SO₂CF₂CF₃ | Cl |
| H | SO₂CF₂CF₂H | Cl | Me | SO₂CF₂CF₂H | Cl |
| H | SO₂CHFCF₃ | Cl | Me | SO₂CHFCF₃ | Cl |
| H | CN | Cl | Me | CN | Cl |

T is Cl and V and U are both Me

| Q | R | S | Q | R | S |
|---|---|---|---|---|---|
| Cl | Cl | H | Cl | Cl | Me |
| Cl | Br | H | Cl | Br | Me |

TABLE 6-continued

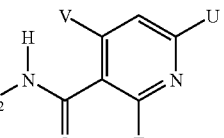

| | | | | | |
|---|---|---|---|---|---|
| Cl | CF₃ | H | Cl | CF₃ | Me |
| Cl | OCF₃ | H | Cl | OCF₃ | Me |
| Cl | OCHF₂ | H | Cl | OCHF₂ | Me |
| Cl | OCH₂CF₃ | H | Cl | OCH₂CF₃ | Me |
| Cl | OCF₂CF₃ | H | Cl | OCF₂CF₃ | Me |
| Cl | OCF₂CF₂H | H | Cl | OCF₂CF₂H | Me |
| Cl | OCHFCF₃ | H | Cl | OCHFCF₃ | Me |
| Cl | SCF₃ | H | Cl | SCF₃ | Me |
| Cl | SCHF₂ | H | Cl | SCHF₂ | Me |
| Cl | SCH₂CF₃ | H | Cl | SCH₂CF₃ | Me |
| Cl | SCF₂CF₃ | H | Cl | SCF₂CF₃ | Me |
| Cl | SCF₂CF₂H | H | Cl | SCF₂CF₂H | Me |
| Cl | SCHFCF₃ | H | Cl | SCHFCF₃ | Me |
| Cl | SOCF₃ | H | Cl | SOCF₃ | Me |
| Cl | SOCHF₂ | H | Cl | SOCHF₂ | Me |
| Cl | SOCH₂CF₃ | H | Cl | SOCH₂CF₃ | Me |
| Cl | SOCF₂CF₃ | H | Cl | SOCF₂CF₃ | Me |
| Cl | SOCF₂CF₂H | H | Cl | SOCF₂CF₂H | Me |
| Cl | SOCHFCF₃ | H | Cl | SOCHFCF₃ | Me |
| Cl | SO₂CF₃ | H | Cl | SO₂CF₃ | Me |
| Cl | SO₂CHF₂ | H | Cl | SO₂CHF₂ | Me |
| Cl | SO₂CH₂CF₃ | H | Cl | SO₂CH₂CF₃ | Me |
| Cl | SO₂CF₂CF₃ | H | Cl | SO₂CF₂CF₃ | Me |
| Cl | SO₂CF₂CF₂H | H | Cl | SO₂CF₂CF₂H | Me |
| Cl | SO₂CHFCF₃ | H | Cl | SO₂CHFCF₃ | Me |
| Cl | CN | H | Cl | CN | Me |
| Cl | H | Cl | Cl | Me | Cl |
| Cl | H | Br | Cl | Me | Br |
| Cl | H | CF₃ | Cl | Me | CF₃ |
| Cl | H | OCF₃ | Cl | Me | OCF₃ |
| Cl | H | OCHF₂ | Cl | Me | OCHF₂ |
| Cl | H | OCH₂CF₃ | Cl | Me | OCH₂CF₃ |
| Cl | H | OCF₂CF₂H | Cl | Me | OCF₂CF₂H |
| Cl | H | SCF₃ | Cl | Me | SCF₃ |
| Cl | H | SCHF₂ | Cl | Me | SCHF₂ |
| Br | SCF₃ | H | Br | SCF₃ | Me |
| Br | SCHF₂ | H | Br | SCHF₂ | Me |
| Br | SCH₂CF₃ | H | Br | SCH₂CF₃ | Me |
| Br | SCF₂CF₃ | H | Br | SCF₂CF₃ | Me |
| Br | SCF₂CF₂H | H | Br | SCF₂CF₂H | Me |
| Br | SCHFCF₃ | H | Br | SCHFCF₃ | Me |
| Br | SOCF₃ | H | Br | SOCF₃ | Me |
| Br | SOCHF₂ | H | Br | SOCHF₂ | Me |
| Br | SOCH₂CF₃ | H | Br | SOCH₂CF₃ | Me |
| Br | SOCF₂CF₃ | H | Br | SOCF₂CF₃ | Me |
| Br | SOCF₂CF₂H | H | Br | SOCF₂CF₂H | Me |
| Br | SOCHFCF₃ | H | Br | SOCHFCF₃ | Me |
| Br | SO₂CF₃ | H | Br | SO₂CF₃ | Me |
| Br | SO₂CHF₂ | H | Br | SO₂CHF₂ | Me |
| Br | SO₂CH₂CF₃ | H | Br | SO₂CH₂CF₃ | Me |
| Br | SO₂CF₂CF₃ | H | Br | SO₂CF₂CF₃ | Me |
| Br | SO₂CF₂CF₂H | H | Br | SO₂CF₂CF₂H | Me |
| Br | SO₂CHFCF₃ | H | Br | SO₂CHFCF₃ | Me |
| Br | CN | H | Br | CN | Me |
| H | Cl | Cl | Me | Cl | Cl |
| H | Br | Cl | Me | Br | Cl |
| H | CF₃ | Cl | Me | CF₃ | Cl |
| H | OCF₃ | Cl | Me | OCF₃ | Cl |
| H | OCHF₂ | Cl | Me | OCHF₂ | Cl |
| H | OCH₂CF₃ | Cl | Me | OCH₂CF₃ | Cl |
| H | OCF₂CF₃ | Cl | Me | OCF₂CF₃ | Cl |
| H | OCF₂CF₂H | Cl | Me | OCF₂CF₂H | Cl |
| H | OCHFCF₃ | Cl | Me | OCHFCF₃ | Cl |
| H | SCF₃ | Cl | Me | SCF₃ | Cl |
| H | SCHF₂ | Cl | Me | SCHF₂ | Cl |
| H | SCH₂CF₃ | Cl | Me | SCH₂CF₃ | Cl |
| H | SCF₂CF₃ | Cl | Me | SCF₂CF₃ | Cl |
| H | SCF₂CF₂H | Cl | Me | SCF₂CF₂H | Cl |
| H | SCHFCF₃ | Cl | Me | SCHFCF₃ | Cl |
| H | SOCF₃ | Cl | Me | SOCF₃ | Cl |

TABLE 6-continued

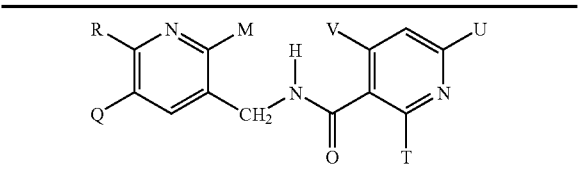

| Q | R | M | V | T | U |
|---|---|---|---|---|---|
| H | SOCHF₂ | Cl | Me | SOCHF₂ | Cl |
| H | SOCH₂CF₃ | Cl | Me | SOCH₂CF₃ | Cl |
| H | SOCF₂CF₃ | Cl | Me | SOCF₂CF₃ | Cl |
| H | SOCF₂CF₂H | Cl | Me | SOCF₂CF₂H | Cl |
| H | SOCHFCF₃ | Cl | Me | SOCHFCF₃ | Cl |
| H | SO₂CF₃ | Cl | Me | SO₂CF₃ | Cl |
| H | SO₂CHF₂ | Cl | Me | SO₂CHF₂ | Cl |
| H | SO₂CH₂CF₃ | Cl | Me | SO₂CH₂CF₃ | Cl |
| H | SO₂CF₂CF₃ | Cl | Me | SO₂CF₂CF₃ | Cl |
| H | SO₂CF₂CF₂H | Cl | Me | SO₂CF₂CF₂H | Cl |
| H | SO₂CHFCF₃ | Cl | Me | SO₂CHFCF₃ | Cl |
| H | CN | Cl | Me | CN | Cl |

TABLE 7

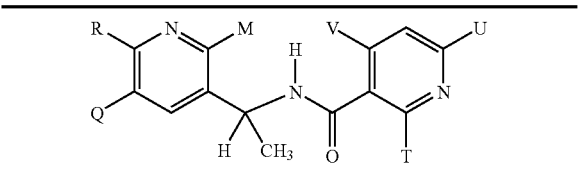

T and V are both Cl and U is H

| Q | R | M | Q | R | M |
|---|---|---|---|---|---|
| Cl | Cl | H | Cl | Cl | Me |
| Cl | Br | H | Cl | Br | Me |
| Cl | CF₃ | H | Cl | CF₃ | Me |
| Cl | OCF₃ | H | Cl | OCF₃ | Me |
| Cl | OCHF₂ | H | Cl | OCHF₂ | Me |
| Cl | OCH₂CF₃ | H | Cl | OCH₂CF₃ | Me |
| Cl | OCF₂CF₃ | H | Cl | OCF₂CF₃ | Me |
| Cl | OCF₂CF₂H | H | Cl | OCF₂CF₂H | Me |
| Cl | OCHFCF₃ | H | Cl | OCHFCF₃ | Me |
| Cl | SCF₃ | H | Cl | SCF₃ | Me |
| Cl | SCHF₂ | H | Cl | SCHF₂ | Me |
| Cl | SCH₂CF₃ | H | Cl | SCH₂CF₃ | Me |
| Cl | SCF₂CF₃ | H | Cl | SCF₂CF₃ | Me |
| Cl | SCF₂CF₂H | H | Cl | SCF₂CF₂H | Me |
| Cl | SCHFCF₃ | H | Cl | SCHFCF₃ | Me |
| Cl | SOCF₃ | H | Cl | SOCF₃ | Me |
| Cl | SOCHF₂ | H | Cl | SOCHF₂ | Me |
| Cl | SOCH₂CF₃ | H | Cl | SOCH₂CF₃ | Me |
| Cl | SOCF₂CF₃ | H | Cl | SOCF₂CF₃ | Me |
| Cl | SOCF₂CF₂H | H | Cl | SOCF₂CF₂H | Me |
| Cl | SOCHFCF₃ | H | Cl | SOCHFCF₃ | Me |
| Cl | SO₂CF₃ | H | Cl | SO₂CF₃ | Me |
| Cl | SO₂CHF₂ | H | Cl | SO₂CHF₂ | Me |
| Cl | SO₂CH₂CF₃ | H | Cl | SO₂CH₂CF₃ | Me |
| Cl | SO₂CF₂CF₃ | H | Cl | SO₂CF₂CF₃ | Me |
| Cl | SO₂CF₂CF₂H | H | Cl | SO₂CF₂CF₂H | Me |
| Cl | SO₂CHFCF₃ | H | Cl | SO₂CHFCF₃ | Me |
| Cl | CN | H | Cl | CN | Me |
| Cl | H | Cl | Cl | Me | Cl |
| Cl | H | Br | Cl | Me | Br |
| Cl | H | CF₃ | Cl | Me | CF₃ |
| Cl | H | OCF₃ | Cl | Me | OCF₃ |
| Cl | H | OCHF₂ | Cl | Me | OCHF₂ |
| Cl | H | OCH₂CF₃ | Cl | Me | OCH₂CF₃ |
| Cl | H | OCF₂CF₂H | Cl | Me | OCF₂CF₂H |
| Cl | H | SCF₃ | Cl | Me | SCF₃ |
| Cl | H | SCHF₂ | Cl | Me | SCHF₂ |
| Br | Cl | H | Br | Cl | Me |
| Br | Br | H | Br | Br | Me |
| Br | CF₃ | H | Br | CF₃ | Me |
| Br | OCF₃ | H | Br | OCF₃ | Me |

TABLE 7-continued

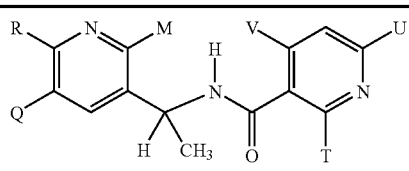

| Q | R | M | Q | R | M |
|---|---|---|---|---|---|
| Br | OCHF₂ | H | Br | OCHF₂ | Me |
| Br | OCH₂CF₃ | H | Br | OCH₂CF₃ | Me |
| Br | OCF₂CF₃ | H | Br | OCF₂CF₃ | Me |
| Br | OCF₂CF₂H | H | Br | OCF₂CF₂H | Me |
| Br | OCHFCF₃ | H | Br | OCHFCF₃ | Me |
| Br | SCF₃ | H | Br | SCF₃ | Me |
| Br | SCHF₂ | H | Br | SCHF₂ | Me |
| Br | SCH₂CF₃ | H | Br | SCH₂CF₃ | Me |
| Br | SCF₂CF₃ | H | Br | SCF₂CF₃ | Me |
| Br | SCF₂CF₂H | H | Br | SCF₂CF₂H | Me |
| Br | SCHFCF₃ | H | Br | SCHFCF₃ | Me |
| Br | SOCF₃ | H | Br | SOCF₃ | Me |
| Br | SOCHF₂ | H | Br | SOCHF₂ | Me |
| Br | SOCH₂CF₃ | H | Br | SOCH₂CF₃ | Me |
| Br | SOCF₂CF₃ | H | Br | SOCF₂CF₃ | Me |
| Br | SOCF₂CF₂H | H | Br | SOCF₂CF₂H | Me |
| Br | SOCHFCF₃ | H | Br | SOCHFCF₃ | Me |
| Br | SO₂CF₃ | H | Br | SO₂CF₃ | Me |
| Br | SO₂CHF₂ | H | Br | SO₂CHF₂ | Me |
| Br | SO₂CH₂CF₃ | H | Br | SO₂CH₂CF₃ | Me |
| Br | SO₂CF₂CF₃ | H | Br | SO₂CF₂CF₃ | Me |
| Br | SO₂CF₂CF₂H | H | Br | SO₂CF₂CF₂H | Me |
| Br | SO₂CHFCF₃ | H | Br | SO₂CHFCF₃ | Me |
| Br | CN | H | Br | CN | Me |
| H | Cl | Cl | Me | Cl | Cl |
| H | Br | Cl | Me | Br | Cl |
| H | CF₃ | Cl | Me | CF₃ | Cl |
| H | OCF₃ | Cl | Me | OCF₃ | Cl |
| H | OCHF₂ | Cl | Me | OCHF₂ | Cl |
| H | OCH₂CF₃ | Cl | Me | OCH₂CF₃ | Cl |
| H | OCF₂CF₃ | Cl | Me | OCF₂CF₃ | Cl |
| H | OCF₂CF₂H | Cl | Me | OCF₂CF₂H | Cl |
| H | OCHFCF₃ | Cl | Me | OCHFCF₃ | Cl |
| H | SCF₃ | Cl | Me | SCF₃ | Cl |
| H | SCHF₂ | Cl | Me | SCHF₂ | Cl |
| H | SCH₂CF₃ | Cl | Me | SCH₂CF₃ | Cl |
| H | SCF₂CF₃ | Cl | Me | SCF₂CF₃ | Cl |
| H | SCF₂CF₂H | Cl | Me | SCF₂CF₂H | Cl |
| H | SCHFCF₃ | Cl | Me | SCHFCF₃ | Cl |
| H | SOCF₃ | Cl | Me | SOCF₃ | Cl |
| H | SOCHF₂ | Cl | Me | SOCHF₂ | Cl |
| H | SOCH₂CF₃ | Cl | Me | SOCH₂CF₃ | Cl |
| H | SOCF₂CF₃ | Cl | Me | SOCF₂CF₃ | Cl |
| H | SOCF₂CF₂H | Cl | Me | SOCF₂CF₂H | Cl |
| H | SOCHFCF₃ | Cl | Me | SOCHFCF₃ | Cl |
| H | SO₂CF₃ | Cl | Me | SO₂CF₃ | Cl |
| H | SO₂CHF₂ | Cl | Me | SO₂CHF₂ | Cl |
| H | SO₂CH₂CF₃ | Cl | Me | SO₂CH₂CF₃ | Cl |
| H | SO₂CF₂CF₃ | Cl | Me | SO₂CF₂CF₃ | Cl |
| H | SO₂CF₂CF₂H | Cl | Me | SO₂CF₂CF₂H | Cl |
| H | SO₂CHFCF₃ | Cl | Me | SO₂CHFCF₃ | Cl |
| H | CN | Cl | Me | CN | Cl |

T and V are both Cl and U is Me

| Q | R | S | Q | R | S |
|---|---|---|---|---|---|
| Cl | Cl | H | Cl | Cl | Me |
| Cl | Br | H | Cl | Br | Me |
| Cl | CF₃ | H | Cl | CF₃ | Me |
| Cl | OCF₃ | H | Cl | OCF₃ | Me |
| Cl | OCHF₂ | H | Cl | OClHF₂ | Me |
| Cl | OCH₂CF₃ | H | Cl | OCH₂CF₃ | Me |
| Cl | OCF₂CF₃ | H | Cl | OCF₂CF₃ | Me |
| Cl | OCF₂CF₂H | H | Cl | OCF₂CF₂H | Me |
| Cl | OCHFCF₃ | H | Cl | OCHFCF₃ | Me |
| Cl | SCF₃ | H | Cl | SCF₃ | Me |
| Cl | SCHF₂ | H | Cl | SCHF₂ | Me |
| Cl | SCH₂CF₃ | H | Cl | SCH₂CF₃ | Me |
| Cl | SCF₂CF₃ | H | Cl | SCF₂CF₃ | Me |

TABLE 7-continued

| R | M | Q | V | U | T |
|---|---|---|---|---|---|
| Cl | SCF$_2$CF$_2$H | H | Cl | SCF$_2$CF$_2$H | Me |
| Cl | SCHFCF$_3$ | H | Cl | SCHFCF$_3$ | Me |
| Cl | SOCF$_3$ | H | Cl | SOCF$_3$ | Me |
| Cl | SOCHF$_2$ | H | Cl | SOCHF$_2$ | Me |
| Cl | SOCH$_2$CF$_3$ | H | Cl | SOCH$_2$CF$_3$ | Me |
| Cl | SOCF$_2$CF$_3$ | H | Cl | SOCF$_2$CF$_3$ | Me |
| Cl | SOCF$_2$CF$_2$H | H | Cl | SOCF$_2$CF$_2$H | Me |
| Cl | SOCHFCF$_3$ | H | Cl | SOCHFCF$_3$ | Me |
| Cl | SO$_2$CF$_3$ | H | Cl | SO$_2$CF$_3$ | Me |
| Cl | SO$_2$CHF$_2$ | H | Cl | SO$_2$CHF$_2$ | Me |
| Cl | SO$_2$CH$_2$CF$_3$ | H | CL | SO$_2$CH$_2$CF$_3$ | Me |
| Cl | SO$_2$CF$_2$CF$_3$ | H | Cl | SO$_2$CF$_2$CF$_3$ | Me |
| Cl | SO$_2$CF$_2$CF$_2$H | H | Cl | SO$_2$CF$_2$CF$_2$H | Me |
| Cl | SO$_2$CHFCF$_3$ | H | Cl | SO$_2$CHFCF$_3$ | Me |
| Cl | CN | H | Cl | CN | Me |
| Cl | H | Cl | Cl | Me | Cl |
| Cl | H | Br | Cl | Me | Br |
| Cl | H | CF$_3$ | Cl | Me | CF$_3$ |
| Cl | H | OCF$_3$ | Cl | Me | OCF$_3$ |
| Cl | H | OCHF$_2$ | Cl | Me | OCHF$_2$ |
| Cl | H | OCH$_2$CF$_3$ | Cl | Me | OCH$_2$CF$_3$ |
| Cl | H | OCF$_2$CF$_2$H | Cl | Me | OCF$_2$CF$_2$H |
| Cl | H | SCF$_3$ | Cl | Me | SCF$_3$ |
| Cl | H | SCHF$_2$ | Cl | Me | SCHF$_2$ |
| Br | SCF$_3$ | H | Br | SCF$_3$ | Me |
| Br | SCHF$_2$ | H | Br | SCHF$_2$ | Me |
| Br | SCH$_2$CF$_3$ | H | Br | SCH$_2$CF$_3$ | Me |
| Br | SCF$_2$CF$_3$ | H | Br | SCF$_2$CF$_3$ | Me |
| Br | SCF$_2$CF$_2$H | H | Br | SCF$_2$CF$_2$H | Me |
| Br | SCHFCF$_3$ | H | Br | SCHFCF$_3$ | Me |
| Br | SOCF$_3$ | H | Br | SOCF$_3$ | Me |
| Br | SOCHF$_2$ | H | Br | SOCHF$_2$ | Me |
| Br | SOCH$_2$CF$_3$ | H | Br | SOCH$_2$CF$_3$ | Me |
| Br | SOCF$_2$CF$_3$ | H | Br | SOCF$_2$CF$_3$ | Me |
| Br | SOCF$_2$CF$_2$H | H | Br | SOCF$_2$CF$_2$H | Me |
| Br | SOCHFCF$_3$ | H | Br | SOCHFCF$_3$ | Me |
| Br | SO$_2$CF$_3$ | H | Br | SO$_2$CF$_3$ | Me |
| Br | SO$_2$CHF$_2$ | H | Br | SO$_2$CHF$_2$ | Me |
| Br | SO$_2$CH$_2$CF$_3$ | H | Br | SO$_2$CH$_2$CF$_3$ | Me |
| Br | SO$_2$CF$_2$CF$_3$ | H | Br | SO$_2$CF$_2$CF$_3$ | Me |
| Br | SO$_2$CF$_2$CF$_2$H | H | Br | SO$_2$CF$_2$CF$_2$H | Me |
| Br | SO$_2$CHFCF$_3$ | H | Br | SO$_2$CHFCF$_3$ | Me |
| Br | CN | H | Br | CN | Me |
| H | Cl | Cl | Me | Cl | Cl |
| H | Br | Cl | Me | Br | Cl |
| H | CF$_3$ | Cl | Me | CF$_3$ | Cl |
| H | OCF$_3$ | Cl | Me | OCF$_3$ | Cl |
| H | OCHF$_2$ | Cl | Me | OCHF$_2$ | Cl |
| H | OCH$_2$CF$_3$ | Cl | Me | OCH$_2$CF$_3$ | Cl |
| H | OCF$_2$CF$_3$ | Cl | Me | OCF$_2$CF$_3$ | Cl |
| H | OCF$_2$CF$_2$H | Cl | Me | OCF$_2$CF$_2$H | Cl |
| H | OCHFCF$_3$ | Cl | Me | OCHFCF$_3$ | Cl |
| H | SCF$_3$ | Cl | Me | SCF$_3$ | Cl |
| H | SCHF$_2$ | Cl | Me | SCHF$_2$ | Cl |
| H | SCH$_2$CF$_3$ | Cl | Me | SCH$_2$CF$_3$ | Cl |
| H | SCF$_2$CF$_3$ | Cl | Me | SCF$_2$CF$_3$ | Cl |
| H | SCF$_2$CF$_2$H | Cl | Me | SCF$_2$CF$_2$H | Cl |
| H | SCHFCF$_3$ | Cl | Me | SCHFCF$_3$ | Cl |
| H | SOCF$_3$ | Cl | Me | SOCF$_3$ | Cl |
| H | SOCHF$_2$ | Cl | Me | SOCHF$_2$ | Cl |
| H | SOCH$_2$CF$_3$ | Cl | Me | SOCH$_2$CF$_3$ | Cl |
| H | SOCF$_2$CF$_3$ | Cl | Me | SOCF$_2$CF$_3$ | Cl |
| H | SOCF$_2$CF$_2$H | Cl | Me | SOCF$_2$CF$_2$H | Cl |
| H | SOCHFCF$_3$ | Cl | Me | SOCHFCF$_3$ | Cl |
| H | SO$_2$CF$_3$ | Cl | Me | SO$_2$CF$_3$ | Cl |
| H | SO$_2$CHF$_2$ | Cl | Me | SO$_2$CHF$_2$ | Cl |
| H | SO$_2$CH$_2$CF$_3$ | Cl | Me | SO$_2$CH$_2$CF$_3$ | Cl |
| H | SO$_2$CF$_2$CF$_3$ | Cl | Me | SO$_2$CF$_2$CF$_3$ | Cl |
| H | SO$_2$CF$_2$CF$_2$H | Cl | Me | SO$_2$CF$_2$CF$_2$H | Cl |
| H | SO$_2$CHFCF$_3$ | Cl | Me | SO$_2$CHFCF$_3$ | Cl |
| H | CN | Cl | Me | CN | Cl |
| Cl | Cl | H | Cl | Cl | Me |
| Cl | Br | H | Cl | Br | Me |
| Cl | CF$_3$ | H | Cl | CF$_3$ | Me |
| Cl | OCF$_3$ | H | Cl | OCF$_3$ | Me |
| Cl | OCHF$_2$ | H | Cl | OCHF$_2$ | Me |
| Cl | OCH$_2$CF$_3$ | H | Cl | OCH$_2$CF$_3$ | Me |
| Cl | OCF$_2$CF$_3$ | H | Cl | OCF$_2$CF$_3$ | Me |
| Cl | OCF$_2$CF$_2$H | H | Cl | OCF$_2$CF$_2$H | Me |
| Cl | OCHFCF$_3$ | H | Cl | OCHFCF$_3$ | Me |
| Cl | SCF$_3$ | H | Cl | SCF$_3$ | Me |
| Cl | SCHF$_2$ | H | Cl | SCHF$_2$ | Me |
| Cl | SCH$_2$CF$_3$ | H | Cl | SCH$_2$CF$_3$ | Me |
| Cl | SCF$_2$CF$_3$ | H | Cl | SCF$_2$CF$_3$ | Me |
| Cl | SCF$_2$CF$_2$H | H | Cl | SCF$_2$CF$_2$H | Me |
| Cl | SCHFCF$_3$ | H | Cl | SCHFCF$_3$ | Me |
| Cl | SOCF$_3$ | H | Cl | SOCF$_3$ | Me |
| Cl | SOCIIF$_2$ | H | Cl | SOCHF$_2$ | Me |
| Cl | SOCH$_2$CF$_3$ | H | Cl | SOCH$_2$CF$_3$ | Me |
| Cl | SOCF$_2$CF$_3$ | H | Cl | SOCF$_2$CF$_3$ | Me |
| Cl | SOCF$_2$CF$_2$H | H | Cl | SOCF$_2$CF$_2$H | Me |
| Cl | SOCHFCF$_3$ | H | Cl | SOCHFCF$_3$ | Me |
| Cl | SO$_2$CF$_3$ | H | Cl | SO$_2$CF$_3$ | Me |
| Cl | SO$_2$CHF$_2$ | H | Cl | SO$_2$CHF$_2$ | Me |
| Cl | SO$_2$CH$_2$CF$_3$ | H | Cl | SO$_2$CH$_2$CF$_3$ | Me |
| Cl | SO$_2$CF$_2$CF$_3$ | H | Cl | SO$_2$CF$_2$CF$_3$ | Me |
| Cl | SO$_2$CF$_2$CF$_2$H | H | Cl | SO$_2$CF$_2$CF$_2$H | Me |
| Cl | SO$_2$CHFCF$_3$ | H | Cl | SO$_2$CHFCF$_3$ | Me |
| Cl | CN | H | Cl | CN | Me |
| Cl | H | Cl | Cl | Me | Cl |
| Cl | H | Br | Cl | Me | Br |
| Cl | H | CF$_3$ | Cl | Me | CF$_3$ |
| Cl | H | OCF$_3$ | Cl | Me | OCF$_3$ |
| Cl | H | OCHF$_2$ | Cl | Me | OCHF$_2$ |
| Cl | H | OCH$_2$CF$_3$ | Cl | Me | OCH$_2$CF$_3$ |
| Cl | H | OCF$_2$CF$_2$H | Cl | Me | OCF$_2$CF$_2$H |
| Cl | H | SCF$_3$ | Cl | Me | SCF$_3$ |
| Cl | H | SCHF$_2$ | Cl | Me | SCHF$_2$ |
| Br | SCF$_3$ | H | Br | SCF$_3$ | Me |
| Br | SCHF$_2$ | H | Br | SCHF$_2$ | Me |
| Br | SCH$_2$CF$_3$ | H | Br | SCH$_2$CF$_3$ | Me |
| Br | SCF$_2$CF$_3$ | H | Br | SCF$_2$CF$_3$ | Me |
| Br | SCF$_2$CF$_2$H | H | Br | SCF$_2$CF$_2$H | Me |
| Br | SCHFCF$_3$ | H | Br | SCHFCF$_3$ | Me |
| Br | SOCF$_3$ | H | Br | SOCF$_3$ | Me |
| Br | SOCHF$_2$ | H | Br | SOCHF$_2$ | Me |
| Br | SOCH$_2$CF$_3$ | H | Br | SOCH$_2$CF$_3$ | Me |
| Br | SOCF$_2$CF$_3$ | H | Br | SOCF$_2$CF$_3$ | Me |
| Br | SOCF$_2$CF$_2$H | H | Br | SOCF$_2$CF$_2$H | Me |
| Br | SOCHFCF$_3$ | H | Br | SOCHFCF$_3$ | Me |
| Br | SO$_2$CF$_3$ | H | Br | SO$_2$CF$_3$ | Me |
| Br | SO$_2$CHF$_2$ | H | Br | SO$_2$CHF$_2$ | Me |
| Br | SO$_2$CH$_2$CF$_3$ | H | Br | SO$_2$CH$_2$CF$_3$ | Me |
| Br | SO$_2$CF$_2$CF$_3$ | H | Br | SO$_2$CF$_2$CF$_3$ | Me |
| Br | SO$_2$CF$_2$CF$_2$H | H | Br | SO$_2$CF$_2$CF$_2$H | Me |
| Br | SO$_2$CHFCF$_3$ | H | Br | SO$_2$CHFCF$_3$ | Me |
| Br | CN | H | Br | CN | Me |
| H | Cl | Cl | Me | Cl | Cl |
| H | Br | Cl | Me | Br | Cl |
| H | CF$_3$ | Cl | Me | CF$_3$ | Cl |
| H | OCF$_3$ | Cl | Me | OCF$_3$ | Cl |
| H | OCHF$_2$ | Cl | Me | OCHF$_2$ | Cl |
| H | OCH$_2$CF$_3$ | Cl | Me | OCH$_2$CF$_3$ | Cl |
| H | OCF$_2$CF$_3$ | Cl | Me | OCF$_2$CF$_3$ | Cl |
| H | OCF$_2$CF$_2$H | Cl | Me | OCF$_2$CF$_2$H | Cl |
| H | OCHFCF$_3$ | Cl | Me | OCHFCF$_3$ | Cl |
| H | SCF$_3$ | Cl | Me | SCF$_3$ | Cl |
| H | SCHF$_2$ | Cl | Me | SCHF$_2$ | Cl |
| H | SCH$_2$CF$_3$ | Cl | Me | SCH$_2$CF$_3$ | Cl |
| H | SCF$_2$CF$_3$ | Cl | Me | SCF$_2$CF$_3$ | Cl |

TABLE 7-continued

| | | | | | |
|---|---|---|---|---|---|
| H | SCF$_2$CF$_2$H | Cl | Me | SCF$_2$CF$_2$H | Cl |
| H | SCHFCF$_3$ | Cl | Me | SCHFCF$_3$ | Cl |
| H | SOCF$_3$ | Cl | Me | SOCF$_3$ | Cl |
| H | SOCHF$_2$ | Cl | Me | SOCHF$_2$ | Cl |
| H | SOCH$_2$CF$_3$ | Cl | Me | SOCH$_2$CF$_3$ | Cl |
| H | SOCF$_2$CF$_3$ | Cl | Me | SOCF$_2$CF$_3$ | Cl |
| H | SOCF$_2$CF$_2$H | Cl | Me | SOCF$_2$CF$_2$H | Cl |
| H | SOCHFCF$_3$ | Cl | Me | SOCHFCF$_3$ | Cl |
| H | SO$_2$CF$_3$ | Cl | Me | SO$_2$CF$_3$ | Cl |
| H | SO$_2$CHF$_2$ | Cl | Me | SO$_2$CHF$_2$ | Cl |
| H | SO$_2$CH$_2$CF$_3$ | Cl | Me | SO$_2$CH$_2$CF$_3$ | Cl |
| H | SO$_2$CF$_2$CF$_3$ | Cl | Me | SO2CF$_2$CF$_3$ | Cl |
| H | SO$_2$CF$_2$CF$_2$H | Cl | Me | SO$_2$CF$_2$CF$_2$H | Cl |
| H | SO$_2$CHFCF$_3$ | Cl | Me | SO$_2$CHFCF$_3$ | Cl |
| H | CN | Cl | Me | CN | Cl |

TABLE 8

T and V are both Cl and u is H

| Q | R | M | Q | R | M |
|---|---|---|---|---|---|
| Cl | Cl | H | Cl | Cl | Me |
| Cl | Br | H | Cl | Br | Me |
| Cl | CF$_3$ | H | Cl | CF$_3$ | Me |
| Cl | OCF$_3$ | H | Cl | OCF$_3$ | Me |
| Cl | OCHF$_2$ | H | Cl | OCHF$_2$ | Me |
| Cl | OCH$_2$CF$_3$ | H | Cl | OCH$_2$CF$_3$ | Me |
| Cl | OCF$_2$CF$_3$ | H | Cl | OCF$_2$CF$_3$ | Me |
| Cl | OCF$_2$CF$_2$H | H | Cl | OCF$_2$CF$_2$H | Me |
| Cl | OCHFCF$_3$ | H | Cl | OCHFCF$_3$ | Me |
| Cl | SCF$_3$ | H | Cl | SCF$_3$ | Me |
| Cl | SCHF$_2$ | H | Cl | SCHF$_2$ | Me |
| Cl | SCH$_2$CF$_3$ | H | Cl | SCH$_2$CF$_3$ | Me |
| Cl | SCF$_2$CF$_3$ | H | Cl | SCF$_2$CF$_3$ | Me |
| Cl | SCF$_2$CF$_2$H | H | Cl | SCF$_2$CF$_2$H | Me |
| Cl | SCHFCF$_3$ | H | Cl | SCHFCF$_3$ | Me |
| Cl | SOCF$_3$ | H | Cl | SOCF$_3$ | Me |
| Cl | SOCHF$_2$ | H | Cl | SOCHF$_2$ | Me |
| Cl | SOCH$_2$CF$_3$ | H | Cl | SOCH$_2$CF$_3$ | Me |
| Cl | SOCF$_2$CF$_3$ | H | Cl | SOCF$_2$CF$_3$ | Me |
| Cl | SOCF$_2$CF$_2$H | H | Cl | SOCF$_2$CF$_2$H | Me |
| Cl | SOCHFCF$_3$ | H | Cl | SOCHFCF$_3$ | Me |
| Cl | SO$_2$CF$_3$ | H | Cl | SO$_2$CF$_3$ | Me |
| Cl | SO$_2$CHF$_2$ | H | Cl | SO$_2$CHF$_2$ | Me |
| Cl | SO$_2$CH$_2$CF$_3$ | H | Cl | SO$_2$CH$_2$CF$_3$ | Me |
| Cl | SO$_2$CF$_2$CF$_3$ | H | Cl | SO$_2$CF$_2$CF$_3$ | Me |
| Cl | SO$_2$CF$_2$CF$_2$H | H | Cl | SO$_2$CF$_2$CF$_2$H | Me |
| Cl | SO$_2$CHFCF$_3$ | H | Cl | SO$_2$CHFCF$_3$ | Me |
| Cl | CN | H | Cl | CN | Me |
| Cl | H | Cl | Cl | Me | Cl |
| Cl | H | Br | Cl | Me | Br |
| Cl | H | CF3 | Cl | Me | CF3 |
| Cl | H | OCF3 | Cl | Me | OCF3 |
| Cl | H | OCHF2 | Cl | Me | OCHF2 |
| Cl | H | OCH2CF3 | Cl | Me | OCH2CF3 |
| Cl | H | OCF2CF2H | Cl | Me | OCF2CF2H |
| Cl | H | SCF3 | Cl | Me | SCF3 |
| Cl | H | SCHF2 | Cl | Me | SCHF2 |
| Br | Cl | H | Br | Cl | Me |

TABLE 8-continued

| | | | | | |
|---|---|---|---|---|---|
| Br | Br | H | Br | Br | Me |
| Br | CF$_3$ | H | Br | CF$_3$ | Me |
| Br | OCF$_3$ | H | Br | OCF$_3$ | Me |
| Br | OCHF$_2$ | H | Br | OCHF$_2$ | Me |
| Br | OCH$_2$CF$_3$ | H | Br | OCH$_2$CF$_3$ | Me |
| Br | OCF$_2$CF$_3$ | H | Br | OCF$_2$CF$_3$ | Me |
| Br | OCF$_2$CF$_2$H | H | Br | OCF$_2$CF$_2$H | Me |
| Br | OCHFCF$_3$ | H | Br | OCHFCF$_3$ | Me |
| Br | SCF$_3$ | H | Br | SCF$_3$ | Me |
| Br | SCHF$_2$ | H | Br | SCHF$_2$ | Me |
| Br | SCH$_2$CF$_3$ | H | Br | SCH$_2$CF$_3$ | Me |
| Br | SCF$_2$CF$_3$ | H | Br | SCF$_2$CF$_3$ | Me |
| Br | SCF$_2$CF$_2$H | H | Br | SCF$_2$CF$_2$H | Me |
| Br | SCHFCF$_3$ | H | Br | SCHFCF$_3$ | Me |
| Br | SOCF$_3$ | H | Br | SOCF$_3$ | Me |
| Br | SOCHF$_2$ | H | Br | SOCHF$_2$ | Me |
| Br | SOCH$_2$CF$_3$ | H | Br | SOCH$_2$CF$_3$ | Me |
| Br | SOCF$_2$CF$_3$ | H | Br | SOCF$_2$CF$_3$ | Me |
| Br | SOCF$_2$CF$_2$H | H | Br | SOCF$_2$CF$_2$H | Me |
| Br | SOCHFCF$_3$ | H | Br | SOCHFCF$_3$ | Me |
| Br | SO$_2$CF$_3$ | H | Br | SO$_2$CF$_3$ | Me |
| Br | SO$_2$CHF$_2$ | H | Br | SO$_2$CHF$_2$ | Me |
| Br | SO$_2$CH$_2$CF$_3$ | H | Br | SO$_2$CH$_2$CF$_3$ | Me |
| Br | SO$_2$CF$_2$CF$_3$ | H | Br | SO$_2$CF$_2$CF$_3$ | Me |
| Br | SO$_2$CF$_2$CF$_2$H | H | Br | SO$_2$CF$_2$CF$_2$H | Me |
| Br | SO$_2$CHFCF$_3$ | H | Br | SO$_2$CHFCF$_3$ | Me |
| Br | CN | H | Br | CN | Me |
| H | Cl | Cl | Me | Cl | Cl |
| H | Br | Cl | Me | Br | Cl |
| H | CF$_3$ | Cl | Me | CF$_3$ | Cl |
| H | OCF$_3$ | Cl | Me | OCF$_3$ | Cl |
| H | OCHF$_2$ | Cl | Me | OCHF$_2$ | Cl |
| H | OCH$_2$CF$_3$ | Cl | Me | OCH$_2$CF$_3$ | Cl |
| H | OCF$_2$CF$_3$ | Cl | Me | OCF$_2$CF$_3$ | Cl |
| H | OCF$_2$CF$_2$H | Cl | Me | OCF$_2$CF$_2$H | Cl |
| H | OCHFCF$_3$ | Cl | Me | OCHFCF$_3$ | Cl |
| H | SCF$_3$ | Cl | Me | SCF$_3$ | Cl |
| H | SCHF$_2$ | Cl | Me | SCHF$_2$ | Cl |
| H | SCH$_2$CF$_3$ | Cl | Me | SCH$_2$CF$_3$ | Cl |
| H | SCF$_2$CF$_3$ | Cl | Me | SCF$_2$CF$_3$ | Cl |
| H | SCF$_2$CF$_2$H | Cl | Me | SCF$_2$CF$_2$H | Cl |
| H | SCHFCF$_3$ | Cl | Me | SCHFCF$_3$ | Cl |
| H | SOCF$_3$ | Cl | Me | SOCF$_3$ | Cl |
| H | SOCHF$_2$ | Cl | Me | SOCHF$_2$ | Cl |
| H | SOCH$_2$CF$_3$ | Cl | Me | SOCH$_2$CF$_3$ | Cl |
| H | SOCF$_2$CF$_3$ | Cl | Me | SOCF$_2$CF$_3$ | Cl |
| H | SOCF$_2$CF$_2$H | Cl | Me | SOCF$_2$CF$_2$H | Cl |
| H | SOCHFCF$_3$ | Cl | Me | SOCHFCF$_3$ | Cl |
| H | SO$_2$CF$_3$ | Cl | Me | SO$_2$CF$_3$ | Cl |
| H | SO$_2$CHF$_2$ | Cl | Me | SO$_2$CHF$_2$ | Cl |
| H | SO$_2$CH$_2$CF$_3$ | Cl | Me | SO$_2$CH$_2$CF$_3$ | Cl |
| H | SO$_2$CF$_2$CF$_3$ | Cl | Me | SO$_2$CF$_2$CF$_3$ | Cl |
| H | SO$_2$CF$_2$CF$_2$H | Cl | Me | SO$_2$CF$_2$CF$_2$H | Cl |
| H | SO$_2$CHFCF$_3$ | Cl | Me | SO$_2$CHFCF$_3$ | Cl |
| H | CN | Cl | Me | CN | Cl |

T and V are both Cl and U is Me

| Q | R | S | Q | R | S |
|---|---|---|---|---|---|
| Cl | Cl | H | Cl | Cl | Me |
| Cl | Br | H | Cl | Br | Me |
| Cl | CF$_3$ | H | Cl | CF$_3$ | Me |
| Cl | OCF$_3$ | H | Cl | OCF$_3$ | Me |
| Cl | OCHF$_2$ | H | Cl | OCHF$_2$ | Me |
| Cl | OCH$_2$CF$_3$ | H | Cl | OCH$_2$CF$_3$ | Me |
| Cl | OCF$_2$CF$_3$ | H | Cl | OCF$_2$CF$_3$ | Me |
| Cl | OCF$_2$CF$_2$H | H | Cl | OCF$_2$CF$_2$H | Me |
| Cl | OCHFCF$_3$ | H | Cl | OCHFCF$_3$ | Me |
| Cl | SCF$_3$ | H | Cl | SCF$_3$ | Me |

TABLE 8-continued

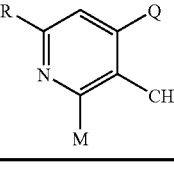

| R | Q | M | V | T | U |
|---|---|---|---|---|---|
| Cl | SCHF₂ | H | Cl | SCHF₂ | Me |
| Cl | SCH₂CF₃ | H | Cl | SCH₂CF₃ | Me |
| Cl | SCF₂CF₃ | H | Cl | SCF₂CF₃ | Me |
| Cl | SCF₂CF₂H | H | Cl | SCF₂CF₂H | Me |
| Cl | SCHFCF₃ | H | Cl | SCHFCF₃ | Me |
| Cl | SOCF₃ | H | Cl | SOCF₃ | Me |
| Cl | SOCHF₂ | H | Cl | SOCHF₂ | Me |
| Cl | SOCH₂CF₃ | H | Cl | SOCH₂CF₃ | Me |
| Cl | SOCF₂CF₃ | H | Cl | SOCF₂CF₃ | Me |
| Cl | SOCF₂CF₂H | H | Cl | SOCF₂CF₂H | Me |
| Cl | SOCHFCF₃ | H | Cl | SOCHFCF₃ | Me |
| Cl | SO₂CF₃ | H | Cl | SO₂CF₃ | Me |
| Cl | SO₂CHF₂ | H | Cl | SO₂CHF₂ | Me |
| Cl | SO₂CH₂CF₃ | H | Cl | SO₂CH₂CF₃ | Me |
| Cl | SO₂CF₂CF₃ | H | Cl | SO₂CF₂CF₃ | Me |
| Cl | SO₂CF₂CF₂H | H | Cl | SO₂CF₂CF₂H | Me |
| Cl | SO₂CHFCF₃ | H | Cl | SO₂CHFCF₃ | Me |
| Cl | CN | H | Cl | CN | Me |
| Cl | H | Cl | Cl | Me | Cl |
| Cl | H | Br | Cl | Me | Br |
| Cl | H | CF₃ | Cl | Me | CF₃ |
| Cl | H | OCF₃ | Cl | Me | OCF₃ |
| Cl | H | OCHF₂ | Cl | Me | OCHF₂ |
| Cl | H | OCH₂CF₃ | Cl | Me | OCH₂CF₃ |
| Cl | H | OCF₂CF₂H | Cl | Me | OCF₂CF₂H |
| Cl | H | SCF₃ | Cl | Me | SCF₃ |
| Cl | H | SCHF₂ | Cl | Me | SCHF₂ |
| Br | SCF₃ | H | Br | SCF₃ | Me |
| Br | SCHF₂ | H | Br | SCHF₂ | Me |
| Br | SCH₂CF₃ | H | Br | SCH₂CF₃ | Me |
| Br | SCF₂CF₃ | H | Br | SCF₂CF₃ | Me |
| Br | SCF₂CF₂H | H | Br | SCF₂CF₂H | Me |
| Br | SCHFCF₃ | H | Br | SCHFCF₃ | Me |
| Br | SOCF₃ | H | Br | SOCF₃ | Me |
| Br | SOCHF₂ | H | Br | SOCHF₂ | Me |
| Br | SOCH₂CF₃ | H | Br | SOCH₂CF₃ | Me |
| Br | SOCF₂CF₃ | H | Br | SOCF₂CF₃ | Me |
| Br | SOCF₂CF₂H | H | Br | SOCF₂CF₂H | Me |
| Br | SOCHFCF₃ | H | Br | SOCHFCF₃ | Me |
| Br | SO₂CF₃ | H | Br | SO₂CF₃ | Me |
| Br | SO₂CHF₂ | H | Br | SO₂CHF₂ | Me |
| Br | SO₂CH₂CF₃ | H | Br | SO₂CH₂CF₃ | Me |
| Br | SO₂CF₂CF₃ | H | Br | SO₂CF₂CF₃ | Me |
| Br | SO₂CF₂CF₂H | H | Br | SO₂CF₂CF₂H | Me |
| Br | SO₂CHFCF₃ | H | Br | SO₂CHFCF₃ | Me |
| Br | CN | H | Br | CN | Me |
| H | Cl | Cl | Me | Cl | Cl |
| H | Br | Cl | Me | Br | Cl |
| H | CF₃ | Cl | Me | CF₃ | Cl |
| H | OCF₃ | Cl | Me | OCF₃ | Cl |
| H | OCHF₂ | Cl | Me | OCHF₂ | Cl |
| H | OCH₂CF₃ | Cl | Me | OCH₂CF₃ | Cl |
| H | OCF₂CF₃ | Cl | Me | OCF₂CF₃ | Cl |
| H | OCF₂CF₂H | Cl | Me | OCF₂CF₂H | Cl |
| H | OCHFCF₃ | Cl | Me | OCHFCF₃ | Cl |
| H | SCF₃ | Cl | Me | SCF₃ | Cl |
| H | SCHF₂ | Cl | Me | SCHF₂ | Cl |
| H | SCH₂CF₃ | Cl | Me | SCH₂CF₃ | Cl |
| H | SCF₂CF₃ | Cl | Me | SCF₂CF₃ | Cl |
| H | SCF₂CF₂H | Cl | Me | SCF₂CF₂H | Cl |
| H | SCHFCF₃ | Cl | Me | SCHFCF₃ | Cl |
| H | SOCF₃ | Cl | Me | SOCF₃ | Cl |
| H | SOCHF₂ | Cl | Me | SOCHF₂ | Cl |
| H | SOCH₂CF₃ | Cl | Me | SOCH₂CF₃ | Cl |
| H | SOCF₂CF₃ | Cl | Me | SOCF₂CF₃ | Cl |
| H | SOCF₂CF₂H | Cl | Me | SOCF₂CF₂H | Cl |
| H | SOCHFCF₃ | Cl | Me | SOCHFCF₃ | Cl |
| H | SO₂CF₃ | Cl | Me | SO₂CF₃ | Cl |
| H | SO₂CHF₂ | Cl | Me | SO₂CHF₂ | Cl |
| H | SO₂CH₂CF₃ | Cl | Me | SO₂CH₂CF₃ | Cl |
| H | SO₂CF₂CF₃ | Cl | Me | SO₂CF₂CF₃ | Cl |
| H | SO₂CF₂CF₂H | Cl | Me | SO₂CF₂CF₂H | Cl |
| H | SO₂CHFCF₃ | Cl | Me | SO₂CHFCF₃ | Cl |
| H | CN | Cl | Me | CN | Cl |

T is Cl and V and U are both Me

| Q | R | S | Q | R | S |
|---|---|---|---|---|---|
| Cl | Cl | H | Cl | Cl | Me |
| Cl | Br | H | Cl | Br | Me |
| Cl | CF₃ | H | Cl | CF₃ | Me |
| Cl | OCF₃ | H | Cl | OCF₃ | Me |
| Cl | OCHF₂ | H | Cl | OCHF₂ | Me |
| Cl | OCH₂CF₃ | H | Cl | OCH₂CF₃ | Me |
| Cl | OCF₂CF₃ | H | Cl | OCF₂CF₃ | Me |
| Cl | OCF₂CF₂H | H | Cl | OCF₂CF₂H | Me |
| Cl | OCHFCF₃ | H | Cl | OCHFCF₃ | Me |
| Cl | SCF₃ | H | Cl | SCF₃ | Me |
| Cl | SCHF₂ | H | Cl | SCHF₂ | Me |
| Cl | SCH₂CF₃ | H | Cl | SCH₂CF₃ | Me |
| Cl | SCF₂CF₃ | H | Cl | SCF₂CF₃ | Me |
| Cl | SCF₂CF₂H | H | Cl | SCF₂CF₂H | Me |
| Cl | SCHFCF₃ | H | Cl | SCHFCF₃ | Me |
| Cl | SOCF₃ | H | Cl | SOCF₃ | Me |
| Cl | SOCHF₂ | H | Cl | SOCHF₂ | Me |
| Cl | SOCH₂CF₃ | H | Cl | SOCH₂CF₃ | Me |
| Cl | SOCF₂CF₃ | H | Cl | SOCF₂CF₃ | Me |
| Cl | SOCF₂CF₂H | H | Cl | SOCF₂CF₂H | Me |
| Cl | SOCHFCF₃ | H | Cl | SOCHFCF₃ | Me |
| Cl | SO₂CF₃ | H | Cl | SO₂CF₃ | Me |
| Cl | SO₂CHF₂ | H | Cl | SO₂CHF₂ | Me |
| Cl | SO₂CH₂CF₃ | H | Cl | SO₂CH₂CF₃ | Me |
| Cl | SO₂CF₂CF₃ | H | Cl | SO₂CF₂CF₃ | Me |
| Cl | SO₂CF₂CF₂H | H | Cl | SO₂CF₂CF₂H | Me |
| Cl | SO₂CHFCF₃ | H | Cl | SO₂CHFCF₃ | Me |
| Cl | CN | H | Cl | CN | Me |
| Cl | H | Cl | Cl | Me | Cl |
| Cl | H | Br | Cl | Me | Br |
| Cl | H | CF3 | Cl | Me | CF3 |
| Cl | H | OCF3 | Cl | Me | OCF3 |
| Cl | H | OCHF2 | Cl | Me | OCHF2 |
| Cl | H | OCH2CF3 | Cl | Me | OCH2CF3 |
| Cl | H | OCF2CF2H | Cl | Me | OCF2CF2H |
| Cl | H | SCF₃ | Cl | Me | SCF₃ |
| Cl | H | SCHF₂ | Cl | Me | SCHF₂ |
| Br | SCF₃ | H | Br | SCF₃ | Me |
| Br | SCHF₂ | H | Br | SCHF₂ | Me |
| Br | SCH₂CF₃ | H | Br | SCH₂CF₃ | Me |
| Br | SCF₂CF₃ | H | Br | SCF₂CF₃ | Me |
| Br | SCF₂CF₂H | H | Br | SCF₂CF₂H | Me |
| Br | SCHFCF₃ | H | Br | SCHFCF₃ | Me |
| Br | SOCF₃ | H | Br | SOCF₃ | Me |
| Br | SOCHF₂ | H | Br | SOCHF₂ | Me |
| Br | SOCH₂CF₃ | H | Br | SOCH₂CF₃ | Me |
| Br | SOCF₂CF₃ | H | Br | SOCF₂CF₃ | Me |
| Br | SOCF₂CF₂H | H | Br | SOCF₂CF₂H | Me |
| Br | SOCHFCF₃ | H | Br | SOCHFCF₃ | Me |
| Br | SO₂CF₃ | H | Br | SO₂CF₃ | Me |
| Br | SO₂CHF₂ | H | Br | SO₂CHF₂ | Me |
| Br | SO₂CH₂CF₃ | H | Br | SO₂CH₂CF₃ | Me |
| Br | SO₂CF₂CF₃ | H | Br | SO₂CF₂CF₃ | Me |
| Br | SO₂CF₂CF₂H | H | Br | SO₂CF₂CF₂H | Me |
| Br | SO₂CHFCF₃ | H | Br | SO₂CHFCF₃ | Me |
| Br | CN | H | Br | CN | Me |
| H | Cl | Cl | Me | Cl | Cl |
| H | Br | Cl | Me | Br | Cl |
| H | CF₃ | Cl | Me | CF₃ | Cl |
| H | OCF₃ | Cl | Me | OCF₃ | Cl |
| H | OCHF₂ | Cl | Me | OCHF₂ | Cl |

TABLE 8-continued

![Structure: R-Q-pyridine(N,M)-CH2-NH-C(=O)-pyridine(T,N,U)-V]

| R | Q | M | V | U | T |
|---|---|---|---|---|---|
| H | OCH$_2$CF$_3$ | Cl | Me | OCH$_2$CF$_3$ | Cl |
| H | OCF$_2$CF$_3$ | Cl | Me | OCF$_2$CF$_3$ | Cl |
| H | OCF$_2$CF$_2$H | Cl | Me | OCF$_2$CF$_2$H | Cl |
| H | OCHFCF$_3$ | Cl | Me | OCHFCF$_3$ | Cl |
| H | SCF$_3$ | Cl | Me | SCF$_3$ | Cl |
| H | SCHF$_2$ | Cl | Me | SCHF$_2$ | Cl |
| H | SCH$_2$CF$_3$ | Cl | Me | SCH$_2$CF$_3$ | Cl |
| H | SCF$_2$CF$_3$ | Cl | Me | SCF$_2$CF$_3$ | Cl |
| H | SCF$_2$CF$_2$H | Cl | Me | SCF$_2$CF$_2$H | Cl |
| H | SCHFCF$_3$ | Cl | Me | SCHFCF$_3$ | Cl |
| H | SOCF$_3$ | Cl | Me | SOCF$_3$ | Cl |
| H | SOCHF$_2$ | Cl | Me | SOCHF$_2$ | Cl |
| H | SOCH$_2$CF$_3$ | Cl | Me | SOCH$_2$CF$_3$ | Cl |
| H | SOCF$_2$CF$_3$ | Cl | Me | SOCF$_2$CF$_3$ | Cl |
| H | SOCF$_2$CF$_2$H | Cl | Me | SOCF$_2$CF$_2$H | Cl |
| H | SOCHFCF$_3$ | Cl | Me | SOCHFCF$_3$ | Cl |
| H | SO$_2$CF$_3$ | Cl | Me | SO$_2$CF$_3$ | Cl |
| H | SO$_2$CHF$_2$ | Cl | Me | SO$_2$CHF$_2$ | Cl |
| H | SO$_2$CH$_2$CF$_3$ | Cl | Me | SO$_2$CH$_2$CF$_3$ | Cl |
| H | SO$_2$CF$_2$CF$_3$ | Cl | Me | SO$_2$CF$_2$CF$_3$ | Cl |
| H | SO$_2$CF$_2$CF$_2$H | Cl | Me | SO$_2$CF$_2$CF$_2$H | Cl |
| H | SO$_2$CHFCF$_3$ | Cl | Me | SO$_2$CHFCF$_3$ | Cl |
| H | CN | Cl | Me | CN | Cl |

TABLE 9

![Structure: R-Q-pyridine(N,M)-CH(CH3)-NH-C(=O)-pyridine(T,N,U)-V]

T and V are both Cl and U is H

| Q | R | M | Q | R | M |
|---|---|---|---|---|---|
| Cl | Cl | H | Cl | Cl | Me |
| Cl | Br | H | Cl | Br | Me |
| Cl | CF$_3$ | H | Cl | CF$_3$ | Me |
| Cl | OCF$_3$ | H | Cl | OCF$_3$ | Me |
| Cl | OCHF$_2$ | H | Cl | OCHF$_2$ | Me |
| Cl | OCH$_2$CF$_3$ | H | Cl | OCH$_2$CF$_3$ | Me |
| Cl | OCF$_2$CF$_3$ | H | Cl | OCF$_2$CF$_3$ | Me |
| Cl | OCF$_2$CF$_2$H | H | Cl | OCF$_2$CF$_2$H | Me |
| Cl | OCHFCF$_3$ | H | Cl | OCHFCF$_3$ | Me |
| Cl | SCF$_3$ | H | Cl | SCF$_3$ | Me |
| Cl | SCHF$_2$ | H | Cl | SCHF$_2$ | Me |
| Cl | SCH$_2$CF$_3$ | H | Cl | SCH$_2$CF$_3$ | Me |
| Cl | SCF$_2$CF$_3$ | H | Cl | SCF$_2$CF$_3$ | Me |
| Cl | SCF$_2$CF$_2$H | H | Cl | SCF$_2$CF$_2$H | Me |
| Cl | SCHFCF$_3$ | H | Cl | SCHFCF$_3$ | Me |
| Cl | SOCF$_3$ | H | Cl | SOCF$_3$ | Me |
| Cl | SOCHF$_2$ | H | Cl | SOCHF$_2$ | Me |
| Cl | SOCH$_2$CF$_3$ | H | Cl | SOCH$_2$CF$_3$ | Me |
| Cl | SOCF$_2$CF$_3$ | H | Cl | SOCF$_2$CF$_3$ | Me |
| Cl | SOCF$_2$CF$_2$H | H | Cl | SOCF$_2$CF$_2$H | Me |
| Cl | SOCHFCF$_3$ | H | Cl | SOCHFCF$_3$ | Me |
| Cl | SO$_2$CF$_3$ | H | Cl | SO$_2$CF$_3$ | Me |
| Cl | SO$_2$CHF$_2$ | H | Cl | SO$_2$CHF$_2$ | Me |
| Cl | SO$_2$CH$_2$CF$_3$ | H | Cl | SO$_2$CH$_2$CF$_3$ | Me |
| Cl | SO$_2$CF$_2$CF$_3$ | H | Cl | SO$_2$CF$_2$CF$_3$ | Me |
| Cl | SO$_2$CF$_2$CF$_2$H | H | Cl | SO$_2$CF$_2$CF$_2$H | Me |
| Cl | SO$_2$CHFCF$_3$ | H | Cl | SO$_2$CHFCF$_3$ | Me |
| Cl | CN | H | Cl | CN | Me |
| Cl | H | Cl | Cl | Me | Cl |
| Cl | H | Br | Cl | Me | Br |

TABLE 9-continued

![Structure: R-Q-pyridine(N,M)-CH(CH3)-NH-C(=O)-pyridine(T,N,U)-V]

| R | Q | M | V | U | T |
|---|---|---|---|---|---|
| Cl | H | CF$_3$ | Cl | Me | CF$_3$ |
| Cl | H | OCF$_3$ | Cl | Me | OCF$_3$ |
| Cl | H | OCHF$_2$ | Cl | Me | OCHF$_2$ |
| Cl | H | OCH$_2$CF$_3$ | Cl | Me | OCH$_2$CF$_3$ |
| Cl | H | OCF$_2$CF$_2$H | Cl | Me | OCF$_2$CF$_2$H |
| Cl | H | SCF$_3$ | Cl | Me | SCF$_3$ |
| Cl | H | SCHF$_2$ | Cl | Me | SCHF$_2$ |
| Br | Cl | H | Br | Cl | Me |
| Br | Br | H | Br | Br | Me |
| Br | CF$_3$ | H | Br | CF$_3$ | Me |
| Br | OCF$_3$ | H | Br | OCF$_3$ | Me |
| Br | OCHF$_2$ | H | Br | OCHF$_2$ | Me |
| Br | OCH$_2$CF$_3$ | H | Br | OCH$_2$CF$_3$ | Me |
| Br | OCF$_2$CF$_3$ | H | Br | OCF$_2$CF$_3$ | Me |
| Br | OCF$_2$CF$_2$H | H | Br | OCF$_2$CF$_2$H | Me |
| Br | OCHFCF$_3$ | H | Br | OCHFCF$_3$ | Me |
| Br | SCF$_3$ | H | Br | SCF$_3$ | Me |
| Br | SCHF$_2$ | H | Br | SCHF$_2$ | Me |
| Br | SCH$_2$CF$_3$ | H | Br | SCH$_2$CF$_3$ | Me |
| Br | SCF$_2$CF$_3$ | H | Br | SCF$_2$CF$_3$ | Me |
| Br | SCF$_2$CF$_2$H | H | Br | SCF$_2$CF$_2$H | Me |
| Br | SCHFCF$_3$ | H | Br | SCHFCF$_3$ | Me |
| Br | SOCF$_3$ | H | Br | SOCF$_3$ | Me |
| Br | SOCHF$_2$ | H | Br | SOCHF$_2$ | Me |
| Br | SOCH$_2$CF$_3$ | H | Br | SOCH$_2$CF$_3$ | Me |
| Br | SOCF$_2$CF$_3$ | H | Br | SOCF$_2$CF$_3$ | Me |
| Br | SOCF$_2$CF$_2$H | H | Br | SOCF$_2$CF$_2$H | Me |
| Br | SOCHFCF$_3$ | H | Br | SOCHFCF$_3$ | Me |
| Br | SO$_2$CF$_3$ | H | Br | SO$_2$CF$_3$ | Me |
| Br | SO$_2$CHF$_2$ | H | Br | SO$_2$CHF$_2$ | Me |
| Br | SO$_2$CH$_2$CF$_3$ | H | Br | SO$_2$CH$_2$CF$_3$ | Me |
| Br | SO$_2$CF$_2$CF$_3$ | H | Br | SO$_2$CF$_2$CF$_3$ | Me |
| Br | SO$_2$CF$_2$CF$_2$H | H | Br | SO$_2$CF$_2$CF$_2$H | Me |
| Br | SO$_2$CHFCF$_3$ | H | Br | SO$_2$CHFCF$_3$ | Me |
| Br | CN | H | Br | CN | Me |
| H | Cl | Cl | Me | Cl | Cl |
| H | Br | Cl | Me | Br | Cl |
| H | CF$_3$ | Cl | Me | CF$_3$ | Cl |
| H | OCF$_3$ | Cl | Me | OCF$_3$ | Cl |
| H | OCHF$_2$ | Cl | Me | OCHF$_2$ | Cl |
| H | OCH$_2$CF$_3$ | Cl | Me | OCH$_2$CF$_3$ | Cl |
| H | OCF$_2$CF$_3$ | Cl | Me | OCF$_2$CF$_3$ | Cl |
| H | OCF$_2$CF$_2$H | Cl | Me | OCF$_2$CF$_2$H | Cl |
| H | OCHFCF$_3$ | Cl | Me | OCHFCF$_3$ | Cl |
| H | SCF$_3$ | Cl | Me | SCF$_3$ | Cl |
| H | SCHF$_2$ | Cl | Me | SCHF$_2$ | Cl |
| H | SCH$_2$CF$_3$ | Cl | Me | SCH$_2$CF$_3$ | Cl |
| H | SCF$_2$CF$_3$ | Cl | Me | SCF$_2$CF$_3$ | Cl |
| H | SCF$_2$CF$_2$H | Cl | Me | SCF$_2$CF$_2$H | Cl |
| H | SCHFCF$_3$ | Cl | Me | SCHFCF$_3$ | Cl |
| H | SOCF$_3$ | Cl | Me | SOCF$_3$ | Cl |
| H | SOCHF$_2$ | Cl | Me | SOCHF$_2$ | Cl |
| H | SOCH$_2$CF$_3$ | Cl | Me | SOCH$_2$CF$_3$ | Cl |
| H | SOCF$_2$CF$_3$ | Cl | Me | SOCF$_2$CF$_3$ | Cl |
| H | SOCF$_2$CF$_2$H | Cl | Me | SOCF$_2$CF$_2$H | Cl |
| H | SOCHFCF$_3$ | Cl | Me | SOCHFCF$_3$ | Cl |
| H | SO$_2$CF$_3$ | Cl | Me | SO$_2$CF$_3$ | Cl |
| H | SO$_2$CHF$_2$ | Cl | Me | SO$_2$CHF$_2$ | Cl |
| H | SO$_2$CH$_2$CF$_3$ | Cl | Me | SO$_2$CH$_2$CF$_3$ | Cl |
| H | SO$_2$CF$_2$CF$_3$ | Cl | Me | SO$_2$CF$_2$CF$_3$ | Cl |
| H | SO$_2$CF$_2$CF$_2$H | Cl | Me | SO$_2$CF$_2$CF$_2$H | Cl |
| H | SO$_2$CHFCF$_3$ | Cl | Me | SO$_2$CHFCF$_3$ | Cl |
| H | CN | Cl | Me | CN | Cl |

T and V are both Cl and U is Me

| Q | R | S | Q | R | S |
|---|---|---|---|---|---|
| Cl | Cl | H | Cl | Cl | Me |
| Cl | Br | H | Cl | Br | Me |

TABLE 9-continued

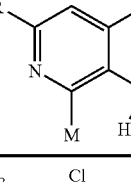

| R | Q | M | V | U | T |
|---|---|---|---|---|---|
| Cl | CF₃ | H | Cl | CF₃ | Me |
| Cl | OCF₃ | H | Cl | OCF₃ | Me |
| Cl | OCHF₂ | H | Cl | OCHF₂ | Me |
| Cl | OCH₂CF₃ | H | Cl | OCH₂CF₃ | Me |
| Cl | OCF₂CF₃ | H | Cl | OCF₂CF₃ | Me |
| Cl | OCF₂CF₂H | H | Cl | OCF₂CF₂H | Me |
| Cl | OCHFCF₃ | H | Cl | OCHFCF₃ | Me |
| Cl | SCF₃ | H | Cl | SCF₃ | Me |
| Cl | SCHF₂ | H | Cl | SCHF₂ | Me |
| Cl | SCH₂CF₃ | H | Cl | SCH₂CF₃ | Me |
| Cl | SCF₂CF₃ | H | Cl | SCF₂CF₃ | Me |
| Cl | SCF₂CF₂H | H | Cl | SCF₂CF₂H | Me |
| Cl | SCHFCF₃ | H | Cl | SCHFCF₃ | Me |
| Cl | SOCF₃ | H | Cl | SOCF₃ | Me |
| Cl | SOCHF₂ | H | Cl | SOCHF₂ | Me |
| Cl | SOCH₂CF₃ | H | Cl | SOCH₂CF₃ | Me |
| Cl | SOCF₂CF₃ | H | Cl | SOCF₂CF₃ | Me |
| Cl | SOCF₂CF₂H | H | Cl | SOCF₂CF₂H | Me |
| Cl | SOCHFCF₃ | H | Cl | SOCHFCF₃ | Me |
| Cl | SO₂CF₃ | H | Cl | SO₂CF₃ | Me |
| Cl | SO₂CHF₂ | H | Cl | SO₂CHF₂ | Me |
| Cl | SO₂CH₂CF₃ | H | Cl | SO₂CH₂CF₃ | Me |
| Cl | SO₂CF₂CF₃ | H | Cl | SO₂CF₂CF₃ | Me |
| Cl | SO₂CF₂CF₂H | H | Cl | SO₂CF₂CF₂H | Me |
| Cl | SO₂CHFCF₃ | H | Cl | SO₂CHFCF₃ | Me |
| Cl | CN | H | Cl | CN | Me |
| Cl | H | Cl | Cl | Me | Cl |
| Cl | H | Br | Cl | Me | Br |
| Cl | H | CF₃ | Cl | Me | CF₃ |
| Cl | H | OCF₃ | Cl | Me | OCF₃ |
| Cl | H | OCHF₂ | Cl | Me | OCHF₂ |
| Cl | H | OCH₂CF₃ | Cl | Me | OCH₂CF₃ |
| Cl | H | OCF₂CF₂H | Cl | Me | OCF₂CF₂H |
| Cl | H | SCF₃ | Cl | Me | SCF₃ |
| Cl | H | SCHF₂ | Cl | Me | SCHF₂ |
| Br | SCF₃ | H | Br | SCF₃ | Me |
| Br | SCHF₂ | H | Br | SCHF₂ | Me |
| Br | SCH₂CF₃ | H | Br | SCH₂CF₃ | Me |
| Br | SCF₂CF₃ | H | Br | SCF₂CF₃ | Me |
| Br | SCF₂CF₂H | H | Br | SCF₂CF₂H | Me |
| Br | SCHFCF₃ | H | Br | SCHFCF₃ | Me |
| Br | SOCF₃ | H | Br | SOCF₃ | Me |
| Br | SOCHF₂ | H | Br | SOCHF₂ | Me |
| Br | SOCH₂CF₃ | H | Br | SOCH₂CF₃ | Me |
| Br | SOCF₂CF₃ | H | Br | SOCF₂CF₃ | Me |
| Br | SOCF₂CF₂H | H | Br | SOCF₂CF₂H | Me |
| Br | SOCFCF₃ | H | Br | SOCFCF₃CF₃ | Me |
| Br | SO₂CF₃ | H | Br | SO₂CF₃ | Me |
| Br | SO₂CHF₂ | H | Br | SO₂CHF₂ | Me |
| Br | SO₂CH₂CF₃ | H | Br | SO₂CH₂CF₃ | Me |
| Br | SO₂CF₂CF₃ | H | Br | SO₂CF₂CF₃ | Me |
| Br | SO₂CF₂CF₂H | H | Br | SO₂CF₂CF₂H | Me |
| Br | SO₂CHFCF₃ | H | Br | SO₂CHFCF₃ | Me |
| Br | CN | H | Br | CN | Me |
| H | Cl | Cl | Me | Cl | Cl |
| H | Br | Cl | Me | Br | Cl |
| H | CF₃ | Cl | Me | CF₃ | Cl |
| H | OCF₃ | Cl | Me | OCF₃ | Cl |
| H | OCHF₂ | Cl | Me | OCHF₂ | Cl |
| H | OCH₂CF₃ | Cl | Me | OCH₂CF₃ | Cl |
| H | OCF₂CF₃ | Cl | Me | OCF₂CF₃ | Cl |
| H | OCF₂CF₂H | Cl | Me | OCF₂CF₂H | Cl |
| H | OCHFCF₃ | Cl | Me | OCHFCF₃ | Cl |
| H | SCF₃ | Cl | Me | SCF₃ | Cl |
| H | SCHF₂ | Cl | Me | SCHF₂ | Cl |
| H | SCH₂CF₃ | Cl | Me | SCH₂CF₃ | Cl |
| H | SCF₂CF₃ | Cl | Me | SCF₂CF₃ | Cl |
| H | SCF₂CF₂H | Cl | Me | SCF₂CF₂H | Cl |
| H | SCHFCF₃ | Cl | Me | SCHFCF₃ | Cl |
| H | SOCF₃ | Cl | Me | SOCF₃ | Cl |

TABLE 9-continued

| R | Q | M | V | U | T |
|---|---|---|---|---|---|
| H | SOCHF₂ | Cl | Me | SOCHF₂ | Cl |
| H | SOCH₂CF₃ | Cl | Me | SOCH₂CF₃ | Cl |
| H | SOCF₂CF₃ | Cl | Me | SOCF₂CF₃ | Cl |
| H | SOCF₂CF₂H | Cl | Me | SOCF₂CF₂H | Cl |
| H | SOCHFCF₃ | Cl | Me | SOCHFCF₃ | Cl |
| H | SO₂CF₃ | Cl | Me | SO₂CF₃ | Cl |
| H | SO₂CHF₂ | Cl | Me | SO₂CHF₂ | Cl |
| H | SO₂CH₂CF₃ | Cl | Me | SO₂CH₂CF₃ | Cl |
| H | SO₂CF₂CF₃ | Cl | Me | SO₂CF₂CF₃ | Cl |
| H | SO₂CF₂CF₂H | Cl | Me | SO₂CF₂CF₂H | Cl |
| H | SO₂CHFCF₃ | Cl | Me | SO₂CHFCF₃ | Cl |
| H | CN | Cl | Me | CN | Cl |

T is Cl and U are both Me

| Q | R | S | Q | R | S |
|---|---|---|---|---|---|
| Cl | Cl | H | Cl | Cl | Me |
| Cl | Br | H | Cl | Br | Me |
| Cl | CF₃ | H | Cl | CF₃ | Me |
| Cl | OCF₃ | H | Cl | OCF₃ | Me |
| Cl | OCHF₂ | H | Cl | OCHF₂ | Me |
| Cl | OCH₂CF₃ | H | Cl | OCH₂CF₃ | Me |
| Cl | OCF₂CF₃ | H | Cl | OCF₂CF₃ | Me |
| Cl | OCF₂CF₂H | H | Cl | OCF₂CF₂H | Me |
| Cl | OCHFCF₃ | H | Cl | OCHFCF₃ | Me |
| Cl | SCF₃ | H | Cl | SCF₃ | Me |
| Cl | SCHF₂ | H | Cl | SCHF₂ | Me |
| Cl | SCH₂CF₃ | H | Cl | SCH₂CF₃ | Me |
| Cl | SCF₂CF₃ | H | Cl | SCF₂CF₃ | Me |
| Cl | SCF₂CF₂H | H | Cl | SCF₂CF₂H | Me |
| Cl | SCHFCF₃ | H | Cl | SCHFCF₃ | Me |
| Cl | SOCF₃ | H | Cl | SOCF₃ | Me |
| Cl | SOCHF₂ | H | Cl | SOCHF₂ | Me |
| Cl | SOCH₂CF₃ | H | Cl | SOCH₂CF₃ | Me |
| Cl | SOCF₂CF₃ | H | Cl | SOCF₂CF₃ | Me |
| Cl | SOCF9CF₂H | H | Cl | SOCF₂CF₂H | Me |
| Cl | SOCHFCF₃ | H | Cl | SOCHFCF₃Me |  |
| Cl | SO₂CF₃ | H | Cl | SO₂CF₃ | Me |
| Cl | SO₂CHF₂ | H | Cl | SO₂CHF₂ | Me |
| Cl | SO₂CH₂CF₃ | H | Cl | SO₂CH₂CF₃Me |  |
| Cl | SO₂CF₂CF₃ | H | Cl | SO₂CF₂CF₃ | Me |
| Cl | SO₂CF₂CF₂H | H | Cl | SO₂CF₂CF₂H | Me |
| Cl | SO₂CHFCF₃ | H | Cl | SO₂CHFCF₃ | Me |
| Cl | CN | H | Cl | CN | Me |
| Cl | H | Cl | Cl | Me | Cl |
| Cl | H | Br | Cl | Me | Br |
| Cl | H | CF₃ | Cl | Me | CF₃ |
| Cl | H | OCF₃ | Cl | Me | OCF₃ |
| Cl | H | OCHF₂ | Cl | Me | OCHF₂ |
| Cl | H | OCH₂CF₃ | Cl | Me | OCH₂CF₃ |
| Cl | H | OCF₂CF₂H | Cl | Me | OCF₂CF₂H |
| Cl | H | SCF₃ | Cl | Me | SCF₃ |
| Cl | H | SCHF₂ | Cl | Me | SCHF₂ |
| Br | SCF₃ | H | Br | SCF₃ | Me |
| Br | SCHF₂ | H | Br | SCHF₂ | Me |
| Br | SCH₂CF₃ | H | Br | SCH₂CF₃ | Me |
| Br | SCF₂CF₃ | H | Br | SCF₂CF₃ | Me |
| Br | SCF₂CF₂H | H | Br | SCF₂CF₂H | Me |
| Br | SCHFCF₃ | H | Br | SCHFCF₃ | Me |
| Br | SOCF₃ | H | Br | SOCF₃ | Me |
| Br | SOCHF₂ | H | Br | SOCHF₂ | Me |
| Br | SOCH₂CF₃ | H | Br | SOCH₂CF₃ | Me |
| Br | SOCF₂CF₃ | H | Br | SOCF₂CF₃ | Me |
| Br | SOCF₂CF₂H | H | Br | SOCF₂CF₂H | Me |
| Br | SOCHFCF₃ | H | Br | SOCHFCF₃ | Me |
| Br | SO₂CF₃ | H | Br | SO₂CF₃ | Me |
| Br | SO₂CHF₂ | H | Br | SO₂CHF₂ | Me |
| Br | SO₂CH₂CF₃ | H | Br | SO₂CH₂CF₃ | Me |
| Br | SO₂CF₂CF₃ | H | Br | SO₂CF₂CF₃ | Me |

TABLE 9-continued

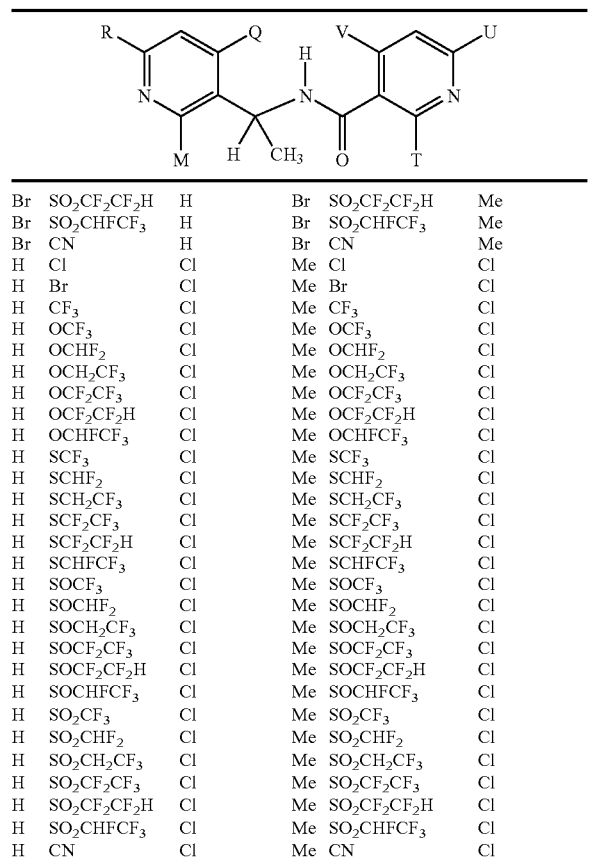

| R | Q | V | U | T | M/CH3 |
|---|---|---|---|---|---|
| Br | SO2CF2CF2H | H | Br | SO2CF2CF2H | Me |
| Br | SO2CHFCF3 | H | Br | SO2CHFCF3 | Me |
| Br | CN | H | Br | CN | Me |
| H | Cl | Cl | Me | Cl | Cl |
| H | Br | Cl | Me | Br | Cl |
| H | CF3 | Cl | Me | CF3 | Cl |
| H | OCF3 | Cl | Me | OCF3 | Cl |
| H | OCHF2 | Cl | Me | OCHF2 | Cl |
| H | OCH2CF3 | Cl | Me | OCH2CF3 | Cl |
| H | OCF2CF3 | Cl | Me | OCF2CF3 | Cl |
| H | OCF2CF2H | Cl | Me | OCF2CF2H | Cl |
| H | OCHFCF3 | Cl | Me | OCHFCF3 | Cl |
| H | SCF3 | Cl | Me | SCF3 | Cl |
| H | SCHF2 | Cl | Me | SCHF2 | Cl |
| H | SCH2CF3 | Cl | Me | SCH2CF3 | Cl |
| H | SCF2CF3 | Cl | Me | SCF2CF3 | Cl |
| H | SCF2CF2H | Cl | Me | SCF2CF2H | Cl |
| H | SCHFCF3 | Cl | Me | SCHFCF3 | Cl |
| H | SOCF3 | Cl | Me | SOCF3 | Cl |
| H | SOCHF2 | Cl | Me | SOCHF2 | Cl |
| H | SOCH2CF3 | Cl | Me | SOCH2CF3 | Cl |
| H | SOCF2CF3 | Cl | Me | SOCF2CF3 | Cl |
| H | SOCF2CF2H | Cl | Me | SOCF2CF2H | Cl |
| H | SOCHFCF3 | Cl | Me | SOCHFCF3 | Cl |
| H | SO2CF3 | Cl | Me | SO2CF3 | Cl |
| H | SO2CHF2 | Cl | Me | SO2CHF2 | Cl |
| H | SO2CH2CF3 | Cl | Me | SO2CH2CF3 | Cl |
| H | SO2CF2CF3 | Cl | Me | SO2CF2CF3 | Cl |
| H | SO2CF2CF2H | Cl | Me | SO2CF2CF2H | Cl |
| H | SO2CHFCF3 | Cl | Me | SO2CHFCF3 | Cl |
| H | CN | Cl | Me | CN | Cl |

TABLE 10

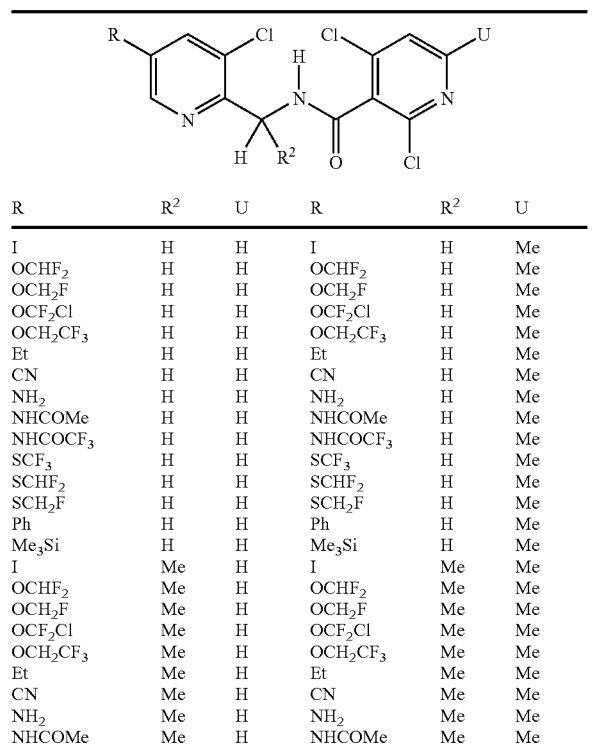

| R | R2 | U | R | R2 | U |
|---|---|---|---|---|---|
| I | H | H | I | H | Me |
| OCHF2 | H | H | OCHF2 | H | Me |
| OCH2F | H | H | OCH2F | H | Me |
| OCF2Cl | H | H | OCF2Cl | H | Me |
| OCH2CF3 | H | H | OCH2CF3 | H | Me |
| Et | H | H | Et | H | Me |
| CN | H | H | CN | H | Me |
| NH2 | H | H | NH2 | H | Me |
| NHCOMe | H | H | NHCOMe | H | Me |
| NHCOCF3 | H | H | NHCOCF3 | H | Me |
| SCF3 | H | H | SCF3 | H | Me |
| SCHF2 | H | H | SCHF2 | H | Me |
| SCH2F | H | H | SCH2F | H | Me |
| Ph | H | H | Ph | H | Me |
| Me3Si | H | H | Me3Si | H | Me |
| I | Me | H | I | Me | Me |
| OCHF2 | Me | H | OCHF2 | Me | Me |
| OCH2F | Me | H | OCH2F | Me | Me |
| OCF2Cl | Me | H | OCF2Cl | Me | Me |
| OCH2CF3 | Me | H | OCH2CF3 | Me | Me |
| Et | Me | H | Et | Me | Me |
| CN | Me | H | CN | Me | Me |
| NH2 | Me | H | NH2 | Me | Me |
| NHCOMe | Me | H | NHCOMe | Me | Me |

TABLE 10-continued

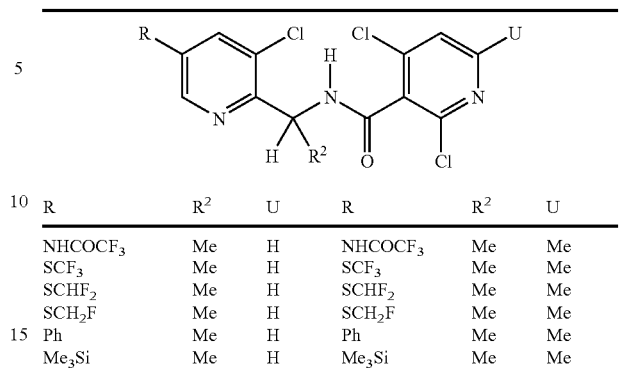

| R | R2 | U | R | R2 | U |
|---|---|---|---|---|---|
| NHCOCF3 | Me | H | NHCOCF3 | Me | Me |
| SCF3 | Me | H | SCF3 | Me | Me |
| SCHF2 | Me | H | SCHF2 | Me | Me |
| SCH2F | Me | H | SCH2F | Me | Me |
| Ph | Me | H | Ph | Me | Me |
| Me3Si | Me | H | Me3Si | Me | Me |

TABLE 11

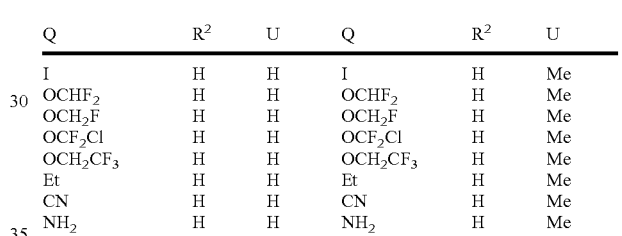

| Q | R2 | U | Q | R2 | U |
|---|---|---|---|---|---|
| I | H | H | I | H | Me |
| OCHF2 | H | H | OCHF2 | H | Me |
| OCH2F | H | H | OCH2F | H | Me |
| OCF2Cl | H | H | OCF2Cl | H | Me |
| OCH2CF3 | H | H | OCH2CF3 | H | Me |
| Et | H | H | Et | H | Me |
| CN | H | H | CN | H | Me |
| NH2 | H | H | NH2 | H | Me |
| NHCOMe | H | H | NHCOMe | H | Me |
| NHCOCF3 | H | H | NHCOCF3 | H | Me |
| SCF3 | H | H | SCF3 | H | Me |
| SCHF2 | H | H | SCHF2 | H | Me |
| SCH2F | H | H | SCH2F | H | Me |
| Ph | H | H | Ph | H | Me |
| Me3Si | H | H | Me3Si | H | Me |
| I | Me | H | I | Me | Me |
| OCHF2 | Me | H | OCHF2 | Me | Me |
| OCH2F | Me | H | OCH2F | Me | Me |
| OCF2Cl | Me | H | OCF2Cl | Me | Me |
| OCH2CF3 | Me | H | OCH2CF3 | Me | Me |
| Et | Me | H | Et | Me | Me |
| CN | Me | H | CN | Me | Me |
| NH2 | Me | H | NH2 | Me | Me |
| NHCOMe | Me | H | NHCOMe | Me | Me |
| NHCOCF3 | Me | H | NHCOCF3 | Me | Me |
| SCF3 | Me | H | SCF3 | Me | Me |
| SCHF2 | Me | H | SCHF2 | Me | Me |
| SCH2F | Me | H | SCH2F | Me | Me |
| Ph | Me | H | Ph | Me | Me |
| Me3Si | Me | H | Me3Si | Me | Me |

TABLE 12

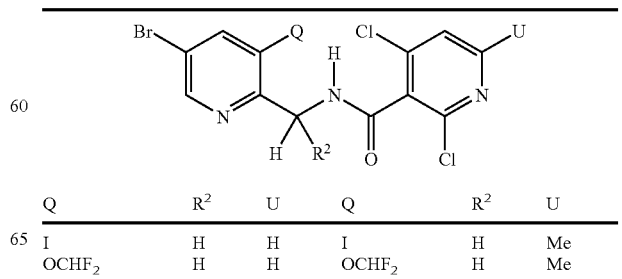

| Q | R2 | U | Q | R2 | U |
|---|---|---|---|---|---|
| I | H | H | I | H | Me |
| OCHF2 | H | H | OCHF2 | H | Me |

TABLE 12-continued

| Q | R² | U | Q | R² | U |
|---|---|---|---|---|---|
| OCH₂F | H | H | OCH₂F | H | Me |
| OCF₂Cl | H | H | OCF₂Cl | H | Me |
| OCH₂CF₃ | H | H | OCH₂CF₃ | H | Me |
| Et | H | H | Et | H | Me |
| CN | H | H | CN | H | Me |
| NH₂ | H | H | NH₂ | H | Me |
| NHCOMe | H | H | NHCOMe | H | Me |
| NHCOCF₃ | H | H | NHCOCF₃ | H | Me |
| SCF₃ | H | H | SCF₃ | H | Me |
| SCHF₂ | H | H | SCHF₂ | H | Me |
| SCH₂F | H | H | SCH₂F | H | Me |
| Ph | H | H | Ph | H | Me |
| Me₃Si | H | H | Me₃Si | H | Me |
| I | Me | H | I | Me | Me |
| OCHF₂ | Me | H | OCHF₂ | Me | Me |
| OCH₂F | Me | H | OCH₂F | Me | Me |
| OCF₂Cl | Me | H | OCF₂Cl | Me | Me |
| OCH₂CF₃ | Me | H | OCH₂CF₃ | Me | Me |
| Et | Me | H | Et | Me | Me |
| CN | Me | H | CN | Me | Me |
| NH₂ | Me | H | NH₂ | Me | Me |
| NHCOMe | Me | H | NHCOMe | Me | Me |
| NHCOCF₃ | Me | H | NHCOCF₃ | Me | Me |
| SCF₃ | Me | H | SCF₃ | Me | Me |
| SCHF₂ | Me | H | SCHF₂ | Me | Me |
| SCH₂F | Me | H | SCH₂F | Me | Me |
| Ph | Me | H | Ph | Me | Me |
| Me₃Si | Me | H | Me₃Si | Me | Me |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts (e.g. from 0.01–99.99 weight percent) of active ingredient together with diluent and/or surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates and Suspension Concentrates) | 5–50 | 40–95 | 0–25 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Preferred suspension concentrates include those containing, in addition to the active ingredient, from 5 to 20% nonionic surfactant (for example, polyethoxylated fatty alcohols) optionally combined with 50–65% liquid diluents and up to 5% anionic surfactants. Granules and pellets can be prepared by spraying the active material upon preformed granular carriers or by agglomeration techniques. See Browning, "Agglomeration", *Chemical Engineering,* Dec. 4, 1967, pp 147–48, *Perry's Chemical Enigineer's Handbook,* 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Tables A–D.

EXAMPLE A

Wettable Powder

| | |
|---|---|
| Compound 8 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

Granule

| | |
|---|---|
| Compound 8 | 10.0% |
| attapulgite granules (low volatile matter, 0.71/0.30 mm; U.S.S. No. 25–50 sieves) | 90.0%. |

EXAMPLE C

Extruded Pellet

| | |
|---|---|
| Compound 8 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

Emulsifiable Concentrate

| | |
|---|---|
| Compound 8 | 20.0% |
| blend of oil soluble sulfonates and polyoxyethylene ethers | 10.0% |
| isophorone | 70.0%. |

Of note are suspension concentrates comprising 15–25% active ingredient, 10–20% nonionic surfactants, 0–5% anionic surfactants, 0–10% organic diluents, and 45–60% water.

EXAMPLE E

| | | |
|---|---|---|
| Compound 2 | | 20.0% |
| polyethoxylated fatty alcohol | nonionic surfactant | 15.0% |
| ester derivative of montan wax | | 3.0% |
| calcium lignosulfonate | anionic surfactant | 2.0% |
| polyethoxylated/polypropoxylated polyglycol block copolymer | surfactant | 1.0% |
| propylene glycol | diluent | 6.4% |
| poly(dimethylsiloxane) | antifoam agent | 0.6% |
| antimicrobial agent | | 0.1% |
| water | diluent | 51.9% |

The formulation ingredients are mixed together as a syrup, Compound 2 is added and the mixture is homogenized in a blender. The resulting slurry is then wet-milled to form a suspension concentrate.

EXAMPLE F

| | | |
|---|---|---|
| Compound 5 | | 20.0% |
| polyethoxylated fatty alcohol | nonionic surfactant | 15.0% |
| ester derivative of montan wax | | 3.0% |
| calcium lignosulfonate | anionic surfactant | 2.0% |
| polyethoxylated/polypropoxylated polyglycol block copolymer | surfactant | 1.0% |
| propylene glycol | diluent | 6.4% |
| poly(dimethylsiloxane) | antifoam agent | 0.6% |
| antimicrobial agent | | 0.1% |
| water | diluent | 51.9% |

The formulation ingredients are mixed together as a syrup, Compound 5 is added and the mixture is homogenized in a blender. The resulting slurry is then wet-milled to form a suspension concentrate.

EXAMPLE G

| | | |
|---|---|---|
| Compound 8 | | 20.0% |
| polyethoxylated fatty alcohol | nonionic surfactant | 15.0% |
| ester derivative of montan wax | | 3.0% |
| calcium lignosulfonate | anionic surfactant | 2.0% |
| polyethoxylated/polypropoxylated polyglycol block copolymer | surfactant | 1.0% |
| propylene glycol | diluent | 6.4% |
| poly(dimethylsiloxane) | antifoam agent | 0.6% |
| antimicrobial agent | | 0.1% |
| water | diluent | 51.9% |

The formulation ingredients are mixed together as a syrup, Compound 8 is added and the mixture is homogenized in a blender. The resulting slurry is then wet-milled to form a suspension concentrate.

EXAMPLE H

| | | |
|---|---|---|
| Compound 28 | | 20.0% |
| polyethoxylated fatty alcohol | nonionic surfactant | 15.0% |
| ester derivative of montan wax | | 3.0% |
| calcium lignosulfonate | anionic surfactant | 2.0% |
| polyethoxylated/polypropoxylated | | |

-continued

| | | |
|---|---|---|
| polyglycol block copolymer | surfactant | 1.0% |
| propylene glycol | diluent | 6.4% |
| poly(dimethylsiloxane) | antifoam agent | 0.6% |
| antimicrobial agent | | 0.1% |
| water | diluent | 51.9% |

The formulation ingredients are mixed together as a syrup, Compound 28 is added and the mixture is homogenized in a blender. The resulting slurry is then wet-milled to form a suspension concentrate.

EXAMPLE I

| | | |
|---|---|---|
| Compound 29 | | 20.0% |
| polyethoxylated fatty alcohol | nonionic surfactant | 15.0% |
| ester derivative of montan wax | | 3.0% |
| calcium lignosulfonate | anionic surfactant | 2.0% |
| polyethoxylated/polypropoxylated polyglycol block copolymer | surfactant | 1.0% |
| propylene glycol | diluent | 6.4% |
| poly(dimethylsiloxane) | antifoam agent | 0.6% |
| antimicrobial agent | | 0.1% |
| water | diluent | 51.9% |

The formulation ingredients are mixed together as a syrup, Compound 29 is added and the mixture is homogenized in a blender. The resulting slurry is then wet-milled to form a suspension concentrate.

EXAMPLE J

| | | |
|---|---|---|
| Compound 30 | | 20.0% |
| polyethoxylated fatty alcohol | nonionic surfactant | 15.0% |
| ester derivative of montan wax | | 3.0% |
| calcium lignosulfonate | anionic surfactant | 2.0% |
| polyethoxylated/polypropoxylated polyglycol block copolymer | surfactant | 1.0% |
| propylene glycol | diluent | 6.4% |
| poly(dimethylsiloxane) | antifoam agent | 0.6% |
| antimicrobial agent | | 0.1% |
| water | diluent | 51.9% |

The formulation ingredients are mixed together as a syrup, Compound 30 is added and the mixture is homogenized in a blender. The resulting slurry is then wet-milled to form a suspension concentrate.

EXAMPLE K

| | | |
|---|---|---|
| Compound 31 | | 20.0% |
| polyethoxylated fatty alcohol | nonionic surfactant | 15.0% |
| ester derivative of montan wax | | 3.0% |
| calcium lignosulfonate | anionic surfactant | 2.0% |
| polyethoxylated/polypropoxylated polyglycol block copolymer | surfactant | 1.0% |
| propylene glycol | diluent | 6.4% |
| poly(dimethylsiloxane) | antifoam agent | 0.6% |
| antimicrobial agent | | 0.1% |
| water | diluent | 51.9% |

The formulation ingredients are mixed together as a syrup, Compound 31 is added and the mixture is homogenized in a blender. The resulting slurry is then wet-milled to form a suspension concentrate.

EXAMPLE L

| | | |
|---|---|---|
| Compound 35 | | 20.0% |
| polyethoxylated fatty alcohol | nonionic surfactant | 15.0% |
| ester derivative of montan wax | | 3.0% |
| calcium lignosulfonate | anionic surfactant | 2.0% |
| polyethoxylated/polypropoxylated polyglycol block copolymer | surfactant | 1.0% |
| propylene glycol | diluent | 6.4% |
| poly(dimethylsiloxane) | antifoam agent | 0.6% |
| antimicrobial agent | | 0.1% |
| water | diluent | 51.9% |

The formulation ingredients are mixed together as a syrup, Compound 35 is added and the mixture is homogenized in a blender. The resulting slurry is then wet-milled to form a suspension concentrate.

EXAMPLE M

| | | |
|---|---|---|
| Compound 36 | | 20.0% |
| polyethoxylated fatty alcohol | nonionic surfactant | 15.0% |
| ester derivative of montan wax | | 3.0% |
| calcium lignosulfonate | anionic surfactant | 2.0% |
| polyethoxylated/polypropoxylated polyglycol block copolymer | surfactant | 1.0% |
| propylene glycol | diluent | 6.4% |
| poly(dimethylsiloxane) | antifoam agent | 0.6% |
| antimicrobial agent | | 0.1% |
| water | diluent | 51.9% |

The formulation ingredients are mixed together as a syrup, Compound 35 is added and the mixture is homogenized in a blender. The resulting slurry is then wet-milled to form a suspension concentrate.

EXAMPLE N

| | | |
|---|---|---|
| Compound 37 | | 20.0% |
| polyethoxylated fatty alcohol | nonionic surfactant | 15.0% |
| ester derivative of montan wax | | 3.0% |
| calcium lignosulfonate | anionic surfactant | 2.0% |
| polyethoxylated/polypropoxylated polyglycol block copolymer | surfactant | 1.0% |
| propylene glycol | diluent | 6.4% |
| poly(dimethylsiloxane) | antifoam agent | 0.6% |
| antimicrobial agent | | 0.1% |
| water | diluent | 51.9% |

The formulation ingredients are mixed together as a syrup, Compound 35 is added and the mixture is homogenized in a blender. The resulting slurry is then wet-milled to form a suspension concentrate.

The compounds of this invention are useful as plant disease control agents. The present invention therefore further comprises a method for controlling plant diseases caused by frugal plant pathogens comprising applying to the plant or portion thereof to be protected, or to the plant seed or seedling to be protected, an effective amount of a compound of the invention or a fungicidal composition containing said compound. The compounds and compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, vegetable, field, cereal, and fruit crops. These pathogens include *Plasmopara viticola, Phytophthora infestans, Peronospora tabacina, Pseudoperonospora cubensis, Pythium aphanidermatum, Alternaria brassicae, Septoria nodorum, Septoria tritici, Cercosporidium personatum, Cercospora arachidicola, Pseudocercosporella herpotrichoides, Cercospora beticola, Botrytis cinerea, Monilinia fructicola, Pyricularia oryzae, Podosphaera leucotricha, Venturia inaequalis, Erysiphe graminis, Uncinula necatur, Puccinia recondita, Puccinia graminis, Hemileia vastatrix, Puccinia striiformis, Puccinia arachidis, Rhizoctonia solani, Sphaerotheca fuliginea, Fusarium oxysporum, Verticillium dahliae, Pythium aphanidermatum, Phytophthora megasperma, Sclerotinia sclerotiorum, Sclerotium rolfsii, Eysiphe polygoni, Pyrenophora teres, Gaeunannomyces graminis, Rynchosporium secalis, Fusarium roseum, Bremia lactucae* and other generea and species closely related to these pathogens.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorfenapyr, chlorpyrifos, chlorpyrifos-methyl, cyfluthrin, beta-cyfluthrin, cyhalothrin, lambda-cyhalothrin, deltamethrin, diafenthiuron, diazinon, diflubenzuron, dimethoate, esfenvalerate, fenoxycarb, fenpropathrin, fenvalerate, fipronil, flucythrinate, tau-fluvalinate, fonophos, imidacloprid, isofeuphos, malathion, metaldehyde, methamidophos, methidathion, methomyl, methoprene, methoxychlor, methyl 7-chloro-2,5-dihydro-2-[[N-(methoxycarbonyl)-N-[4-(trifluoromethoxy)phenyl]amino]carbonyl]indeno[1,2-e][1,3,4]oxadiazine-4a(3H)-carboxylate (indoxacarb), monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; fiugicides such as acibenzolar, azoxystrobin, benomyl, blasticidin-S, Bordeaux mixture (tribasic copper sulfate), bromuconazole, carpropamid (KTU 3616), captafol, captan, carbendazim, chloroneb, chlorothalonil, copper oxychloride, copper salts such as copper sulfate and copper hydroxide, cyazofamid, cymoxanil, cyproconazole, cyprodinil (CGA 219417), (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, dimethomorph, diniconazole, diniconazole-M, dodine, edifenphos, epoxiconazole (BAS 480F), famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, firalaxyl, furametapyr (S-82658), hexaconazole, ipconazole, iprobenfos, iprodione, isoprothiolane, iprovalicarb, kasugamycin, kresoxim-methyl, mancozeb, maneb, mefenoxam, mepronil, metalaxyl, metconazole, metominostrobin/fenominostrobin (SSF-126), myclobutanil, neo-asozin (ferric methanearsonate), oxadixyl, penconazole, pencycuron, probenazole, prochloraz, propamocarb, propiconazole, propineb, pyrclostrobin, pyrifenox, pyrimethanil, pyroquilon, quinoxyfen, spiroxamine, sulfur, tebuconazole, tetraconazole, thiabendazole, thifluzamide, thiophanate-methyl, thiram, triadimefon, triadimenol, tricyclazole, trifloxystrobin, triticonazole, validamycin, vinclozolin, zineb and zoxamid; nematocides such as aldoxycarb and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathriu, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi. The weight ratios of these various mixing partners to compounds of this invention typically are between 100:1 and 1:100, preferably between 30:1 and 1:30, more preferably between 10:1 and 1:10 and most preferably between 4:1 and 1:4.

Of note are combinations with other fungicides giving an even broader spectrum of agricultural protection including azoxystrobin, kresoxim-methyl, pyrclostrobin, trifloxystrobin, benomyl, carbendazim, chlorothalonil, dimethomorph, folpet, mancozeb, maneb, quinoxyfen, validamycin, vinclozolin, fenpropidine, fenpropimorph, bromuconazole, cyproconazole, difenoconazole, epoxyconazole, flusilazole, ipconazole, metconazole, propiconazole, tebuconazole and triticonazole.

Of note are combinations with other fungicides of a different mode of action (e.g. mitochondrial respiration inhibition, inhibition of protein synthesis by interference of the synthesis of ribosomal RNA or inhibition of beta-tubulin synthesis) that can be particularly advantageous for resistance management. Examples include combinations of compounds of Formula I and/or Formula II (e.g. Compound 8) with azoxystrobin, kresoxim-methyl, pyrclostrobin, trifloxystrobin, carbendazim, famoxadone, fenamidone, benomyl, cymoxanil, dimethomorph, folpet, fosetyl-aluminum, metalaxyl, mancozeb, maneb. These combinations can be particularly advantageous for resistance management, especially where the fungicides of the combination control the same or similar diseases.

Of note are combinations with other fungicides for controlling grape diseases including dithiocarbamates such as mancozeb, maneb, propineb and zineb, phthalimids such as folpet, copper salts such as copper sulfate and copper hydroxide, strobilurins such as azoxystrobin, pyrclostrobin and trifloxystrobin, phenylamides such as metalaxyl, phosphonates such as fosetyl-Al, morpholines such as dimethomorph, and other fungicides such as cymoxanil, famoxadone and fenamidone.

Of note are combinations with other fungicides for controlling potato diseases including dithiocarbamates such as mancozeb, maneb, propineb and zineb, copper salts such as copper sulfate and copper hydroxide, strobilurins such as pyrclostrobin and trifloxystrobin, phenylamides such as metalaxyl, carbamates such as propamocarb, phenylpyriylamines such as fluazinam, morpholines such as dimethomorph, and other fungicides such as chlorothalonil, cyazofamid, cymoxanil, famoxadone, fenamidone, zoxamid and iprovalicarb.

Of particular note are combinations of Compound 2, Compound 5, Compound 8, Compound 28, Compound 29, Compound 30, Compound 31, Compound 35, Compound 36 or Compound 37 with azoxystrobin, combinations of Compound 2, Compound 5, Compound 8, Compound 28, Compound 29, Compound 30, Compound 31, Compound 35, Compound 36 or Compound 37 with kresoxim-methyl, combinations of Compound 2, Compound 5, Compound 8, Compound 28, Compound 29, Compound 30, Compound 31, Compound 35, Compound 36 or Compound 37 with pyrclostrobin, combinations of Compound 2, Compound 5, Compound 8, Compound 28, Compound 29, Compound 30, Compound 31, Compound 35, Compound 36 or Compound 37 with trifloxystrobin, combinations of Compound 2, Compound 5, Compound 8, Compound 28, Compound 29, Compound 30, Compound 31, Compound 35, Compound 36 or Compound 37 with carbendazim, combinations of Compound 2, Compound 5, Compound 8, Compound 28, Compound 29, Compound 30, Compound 31, Compound 35, Compound 36 or Compound 37 with chlorothalonil, combinations of Compound 2, Compound 5, Compound 8, Compound 28, Compound 29, Compound 30, Compound 31, Compound 35, Compound 36 or Compound 37 with dimethomorph, combinations of Compound 2, Compound 5, Compound 8, Compound 28, Compound 29, Compound 30, Compound 31, Compound 35, Compound 36 or Compound 37 with folpet, combinations of Compound 2, Compound 5, Compound 8, Compound 28, Compound 29, Compound 30, Compound 31, Compound 35, Compound 36 or Compound 37 with mancozeb, combinations of Compound 2, Compound 5, Compound 8, Compound 28, Compound 29, Compound 30, Compound 31, Compound 35, Compound 36 or Compound 37 with maneb, combinations of Compound 2, Compound 5, Compound 8, Compound 28, Compound 29, Compound 30, Compound 31, Compound 35, Compound 36 or Compound 37 with quinoxyfen, combinations of Compound 2, Compound 5, Compound 8, Compound 28, Compound 29, Compound 30, Compound 31, Compound 35, Compound 36 or Compound 37 with validamycin, combinations of Compound 2, Compound 5, Compound 8, Compound 28, Compound 29, Compound 30, Compound 31, Compound 35, Compound 36 or Compound 37 with vinclozolin, Compound 2, Compound 5, Compound 8, Compound 28, Compound 29, Compound 30, Compound 31, Compound 35, Compound 36 or Compound 37 with fenpropidine, Compound 2, Compound 5, Compound 8, Compound 28, Compound 29, Compound 30, Compound 31, Compound 35, Compound 36 or Compound 37 with fenpropimorph, Compound 2, Compound 5, Compound 8, Compound 28, Compound 29, Compound 30, Compound 31, Compound 35, Compound 36 or Compound 37 with bromuconazole, Compound 2, Compound 5, Compound 8, Compound 28, Compound 29, Compound 30, Compound 31, Compound 35, Compound 36 or Compound 37 with cyproconazole, Compound 2, Compound 5, Compound 8, Compound 28, Compound 29, Compound 30, Compound 31, Compound 35, Compound 36 or Compound 37 with difenoconazole, Compound 2, Compound 5, Compound 8, Compound 28, Compound 29, Compound 30, Compound 31, Compound 35, Compound 36 or Compound 37 with epoxyconazole, Compound 2, Compound 5, Compound 8, Compound 28, Compound 29, Compound 30, Compound 31, Compound 35, Compound 36 or Compound 37 with flusilazole, Compound 2, Compound 5, Compound 8, Compound 28, Compound 29, Compound 30, Compound 31, Compound 35, Compound 36 or Compound 37 with ipconazole, Compound 2, Compound 5, Compound 8, Compound 28, Compound 29, Compound 30, Compound 31, Compound 35, Compound 36 or Compound 37 with metconazole, Compound 2, Compound 5, Compound 8, Compound 28, Compound 29, Compound 30, Compound 31, Compound 35, Compound 36 or Compound 37 with propiconazole, Compound 2, Compound 5, Compound 8, Compound 28, Compound 29, Compound 30, Compound 31, Compound 35, Compound 36 or Compound 37 with tebuconazole, Compound 2, Compound 5, Compound 8, Compound 28, Compound 29, Compound 30, Compound 31, Compound 35, Compound 36 or Compound 37 with triticonazole, Compound 2, Compound 5, Compound 8, Compound 28, Compound 29, Compound 30, Compound 31, Compound 35, Compound 36 or Compound 37 with famoxadone, Compound 2, Compound 5, Compound 8, Compound 28, Compound 29, Compound 30, Compound 31, Compound 35, Compound 36 or Compound 37 with fenamidone, Compound 2, Compound 5, Compound 8, Compound 28, Compound 29, Compound 30, Compound 31, Compound 35, Compound 36 or Compound 37 with benomyl, Compound 2, Compound 5, Compound 8, Compound 28, Compound 29, Compound 30, Compound 31, Compound 35, Compound 36 or Compound 37 with cymoxanil, Compound 2, Compound 5, Compound 8, Compound 28, Compound 29, Compound 30, Compound 31, Compound 35, Compound 36 or Compound 37 with dimethomorph, Compound 2, Compound 5, Compound 8, Compound 28, Compound 29, Compound 30, Compound 31, Compound 35, Compound 36 or Compound 37 with folpet, Compound 2, Compound 5, Compound 8, Compound 28, Compound 29, Compound 30, Compound 31, Compound 35, Compound 36 or Compound 37 with fosetyl-aluminum, Compound 2, Compound 5, Compound 8, Compound 28, Compound 29, Compound 30, Compound 31, Compound 35, Compound 36 or Compound 37 with metalaxyl, Compound 2, Compound 5, Compound 8, Compound 28, Compound 29, Compound 30, Compound 31, Compound 35, Compound 36 or Compound 37 with Compound 2, Compound 5, Compound 8, Compound 28, Compound 29, Compound 30, Compound 31, Compound 35, Compound 36 or Compound 37 with propineb, Compound 2, Compound 5, Compound 8, Compound 28, Compound 29, Compound 30, Compound 31, Compound 35, Compound 36 or Compound 37 with zineb, Compound 2, Compound 5, Compound 8, Compound 28, Compound 29, Compound 30, Compound 31, Compound 35, Compound 36 or Compound 37 with copper sulfate, Compound 2, Compound 5, Compound 8, Compound 28, Compound 29, Compound 30, Compound 31, Compound 35, Compound 36 or Compound 37 with copper hydroxide, Compound 2, Compound 5, Compound 8, Compound 28, Compound 29, Compound 30, Compound 31, Compound 35, Compound 36 or Compound 37 with propamocarb, Compound 2, Compound 5, Compound 8, Compound 28, Compound 29, Compound 30, Compound 31, Compound 35, Compound 36 or Compound 37 with cyazofamid, Compound 2, Compound 5, Compound 8, Compound 28, Compound 29, Compound 30, Compound 31, Compound 35, Compound 36 or Compound 37 with zoxamid and Compound 2, Compound 5, Compound 8, Compound 28, Compound 29, Compound 30, Compound 31, Compound 35, Compound 36 or Compound 37 with iprovalicarb.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling.

Rates of application for these compounds can be influenced by many factors of the environment and should be determined under actual use conditions. Foliage can normally be protected when treated at a rate of from less than 1 g/ha to 5,000 g/ha of active ingredient. Seed and seedlings can normally be protected when seed is treated at a rate of from 0.1 to 10 g per kilogram of seed.

The following TESTS demonstrate the control efficacy of compounds of this invention on specific pathogens. The pathogen control protection afforded by the compounds is not limited, however, to these species. See Index Tables A-E for compound descriptions. The following abbreviations are used in the Index Tables that follow: Me is methyl, Et is ethyl, Ph is phenyl, OMe is methoxy, OEt is ethoxy. The abbreviation "dec" indicates that the compound appeared to decompose on melting. The abbreviation "Ex." stands for "Example" and is followed by a number indicating in which example the compound is prepared.

INDEX TABLE A

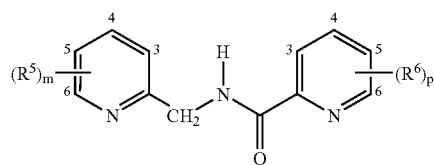

| Compound Number | $(R^5)_m$ | $(R^6)_m$ | m.p. (° C.) |
|---|---|---|---|
| 1 | 3-Cl-5-CF$_3$ | 3-Cl | 108–109 |
| 2 | 3-Cl-5-CF$_3$ | 3-Cl-5-Me | |
| 3 | 3-Cl-5-CF$_3$ | 3-OH | |

INDEX TABLE B

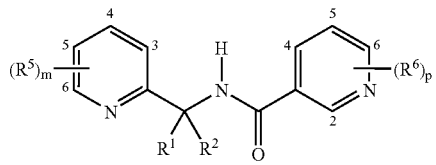

| Compound Number | $R^1$ | $R^2$ | $(R^5)_m$ | $(R^6)_p$ | m.p. (° C.) |
|---|---|---|---|---|---|
| 4 | H | H | 3-Cl-5-CF$_3$ | 2,6-Cl$_2$ | 110–111 |
| 5 | H | H | 3-Cl-5-CF$_3$ | 2-Cl | * |
| 6 | H | H | 3-Cl-5-CF$_3$ | 6-Cl | |
| 7 | H | H | 3-Cl-5-CF$_3$ | 5,6-Cl$_2$ | * |
| 8 (Ex. 1) | H | H | 3-Cl-5-CF$_3$ | 2,4-Cl$_2$-6-Me | * |
| 9 | H | H | 3-Cl-5-CF$_3$ | 2-NH$_2$ | |
| 10 | H | H | 3-Cl-5-CF$_3$ | 5-Br | |
| 11 | H | H | 3-Cl-5-CF$_3$ | 2-OH | |
| 12 | H | H | 3-Cl-5-CF$_3$ | 2-OMe | |
| 13 | H | H | 3-Cl-5-CF$_3$ | 2-OEt | |
| 14 | H | H | 3-Cl-5-CF$_3$ | 2-Cl-6-Me | |
| 15 | H | H | 3-Cl-5-CF$_3$ | 2-OPh | |
| 16 | H | H | 3-Cl-5-CF$_3$ | 2-SPh | |
| 17 | H | H | 3-Cl-5-CF$_3$ | 5-C≡C-Ph | |
| 18 | H | H | 3-Cl-5-CF$_3$ | 2-Br-6-CF$_3$ | * |
| 19 | H | H | 3-Cl-5-CF$_3$ | 2-OH-6-Me | * |
| 20 | H | H | 3-Cl-5-CF$_3$ | 2-Me-6-CF$_3$ | * |
| 21 | H | H | 3-Cl-5-CF$_3$ | 2-Me-6-CF$_2$CF$_3$ | * |
| 22 | H | H | 3-Cl-5-CF$_3$ | 2-OMe-6-CF$_3$ | * |
| 23 | H | H | 3-Cl-5-CF$_3$ | 2-CH$_2$OMe-6-CF$_3$ | * |
| 24 | H | H | 3-Cl-5-CF$_3$ | 2-Ph-6-CF$_3$ | * |
| 25 | H | H | 3-Cl-5-CF$_3$ | 2-Me-6-Cl | * |
| 26 | H | H | 3-Cl-5-CF$_3$ | 6-CF$_3$ | * |
| 27 | H | H | 3-Cl-5-CF$_3$ | 2-NH—C$_6$H$_4$(3-CF$_3$) | * |
| 28 (Ex. 2) | H | H | 3-Cl-5-CF$_3$ | 2,4-Cl$_2$ | 122–124 |
| 29 | H | H | 3-Cl-5-CF$_3$ | 2,4-Cl$_2$-5-Me | * |
| 30 (Ex. 3) racemic | H | CH$_3$ | 3-Cl-5-CF$_3$ | 2,4-Cl$_2$ | * |
| 31 (Ex. 4) (+)-enantiomer | H | CH$_3$ | 3-Cl-5-CF$_3$ | 2,4-Cl$_2$ | 110–111 |
| 36 (Ex. 6) racemic | H | CH$_3$ | 3,5-Cl$_2$ | 2,4-Cl$_2$ | * |
| 37 (Ex. 5) racemic | H | CH$_3$ | 3-Cl-5-Br | 2,4-Cl$_2$ | * |
| 38 (−)-enantiomer | H | CH$_3$ | 3-Cl-5-CF$_3$ | 2,4-Cl$_2$ | * |

*See Index Table E for $^1$H NMR data.

INDEX TABLE C

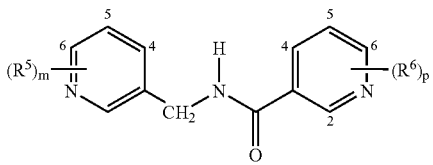

| Compound Number | $(R^5)_m$ | $(R^6)_p$ | m.p. (° C.) |
|---|---|---|---|
| 32 | 6-Cl | 2-Me | 105–106 |
| 33 | 6-OC$_6$H$_4$(3-CF$_3$) | 2-Me | 90–91 |

INDEX TABLE D

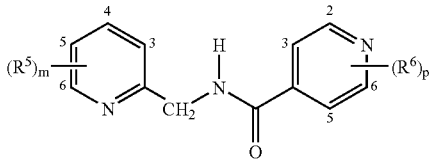

| Compound Number | $(R^5)_m$ | $(R^6)_p$ | m.p. (° C.) |
|---|---|---|---|
| 34 | 3-Cl-5-CF$_3$ | 2-Cl-6-OMe | * |
| 35 | 3-Cl-5-CF$_3$ | 3,5-Cl$_2$ | * |

*See Index Table E for $^1$H NMR data.

INDEX TABLE E

Cmpd No.  $^1$H NMR Data(300mHz; CDCl$_3$ solution unless indicated otherwise)$^a$

| | |
|---|---|
| 5 | δ 4.95(m, 2H), 7.44(m, 1H), 8.0(s, 1H), 8.2–8.3(m, 2H), 8.5(m, 1H), 8.8(m, 1H) |
| 7 | (DMSO-d$_6$) δ 4.8(m, 2H), 8.54(s, 1H), 8.55(s, 1H), 8.84(s, 1H), 8.9(s, 1H), 9.5(bs, 1H) |
| 8 | δ 2.57(s, 3H), 4.96(m, 2H), 7.22(s, 1H), 7.48(bs, 1H), 8.00(s, 1H), 8.71(s, 1H) |
| 18 | δ 4.95(m, 2H), 7.76(m, 1H), 7.94(bs, 1H), 8.00(s, 1H), 8.16(m, 1H), 8.74(s, 1H) |
| 19 | (DMSO-d$_6$) δ 2.30(s, 3H), 4.8(m, 2H), 6.3(m, 1H), 8.2(m, 1H), 8.47(s, 1H), 8.93(s, 1H), 10.4 (m, 1H), 12.4(bs, 1H) |
| 20 | δ 2.80(s, 3H), 4.94(m, 2H), 7.4(bs, 1H), 7.6(m, 1H), 8.0(m, 2H), 8.73(s, 1H) |
| 21 | δ 2.80(s, 3H), 4.95(m, 2H), 7.4(bs, 1H), 7.6(m, 1H), 8.0(m, 2H), 8.72(s, 1H) |
| 22 | δ 4.97(m, 2H), 7.44(m, 1H), 7.99(s, 1H), 8.71(m, 1H), 8.80(s, 1H), 9.42(bs, 1H) |
| 23 | δ 3.50(s, 3H), 4.87,(s, 2H), 4.98(m, 2H), 7.79(m, 1H), 7.98(s, 1H), 8.38(m, 1H), 8.74(s, 1H), 8.88(bs, 1H) |
| 24 | δ 4.70(m, 2H), 7.0(bs, 1H), 7.3–4(m, 3H), 7.7–7.8(m, 3H), 7.9(s, 1H), 8.25(m, 1H), 8.4(s, 1H) |
| 25 | δ 2.73(s, 3H), 4.91(m, 2H), 7.25(m, 1H), 7.4(bs, 1H), 7.8(m, 1H), 8.00(s, 1H), 8.73(s, 1H) |
| 26 | δ 4.94(m, 2H), 7.80(m, 1H), 7.9(bs, 1H), 8.0(s, 1H), 8.40(m, 1H), 8.77(s, 1H), 9.22(s, 1H) |
| 27 | (DMSO-d$_6$) δ 4.8(m, 2H), 7.0(m, 1H), 7.3(m, 1H), 7.3(m, 1H), 7.5(m, 1H), 7.8(m, 1H), 8.3 (m, 2H), 8.4(m, 1H), 8.5(s, 1H), 8.9(s, 1H), 9.5(m, 1H) |
| 30 | δ 1.62(d, 3H, J is 6.7Hz), 5.84(m, 1H), 7.35(d, 1H, J is 5.2Hz), 7.40(d, 1H, J is 6.9Hz), 7.99 (d, 1H, J is 1.8Hz), 8.34(d, 1H, J is 5.2Hz), 8.70(s, 1H) |
| 34 | δ 4.00(s, 3H), 4.88,(m, 2H), 7.09(s, 1H), 7.33(m, 1H), 7.80(bs, 1H), 8.00(s, 1H), 8.78(s, 1H) |
| 35 | δ 4.98(d, 2H, J is 3.8), 7.5(bs, 1H), 8.00(s, 1H), 8.58(s, 2H), 8.71(s, 1H). |
| 36 | δ 1.58(d, 3H, J is 6.6Hz), 5.7–5.8(m, 1H), 7.4(m, 2H), 7.77(m, 1H), 8.35(m, 1H), 8.40(m, 1H). |
| 37 | δ 1.59(d, 3H, J is 6.6Hz), 5.75(m, 1H), 7.3(bs, 1H), 7.34(d, 1H, J is 5.2Hz), 7.91(d, 1H, J is 1.9Hz), 8.33(d, 1H, J is 5.4Hz), 8.49(d, 1H, J is 1.9Hz). |
| 38 | δ 1.62(d, 3H, J is 6.7Hz), 5.48(m, 1H), 7.35(d, 1H, J is 5.2Hz), 7.40(d, 1H, J is 6.9), 7.99(d, 1H, J is 1.8Hz), 8.34(d, 1H, J is 5.2), 8.70(s, 1H). |

$^a$$^1$H NMR data are in ppm downfield from tetramethylsilane. Couplings are designated by(s)-singlet,(d)-doublet, (t)-triplet,(q)-quartet,(m)-multiplet,(dd)-doublet of doublets,(dt)-doublet of triplets,(brs)-broad singlet.

BIOLOGICAL EXAMPLES OF THE INVENTION

General protocol for preparing test suspensions: Test compounds are first dissolved in acetone in an amount equal to 3% of the final volume and then suspended at the desired concentration (in ppm) in acetone and purified water (50/50 mix) containing 250 ppm of the surfactant Trem® 014 (polyhydric alcohol esters). The resulting test suspensions are then used in the following tests. Spraying a 200 ppm test suspension to the point of run-off on the test plants is the equivalent of a rate of 500 g/ha.

TEST A

The test suspension was sprayed to the point of run-off on wheat seedlings. The following day the seedlings were inoculated with a spore dust of *Erysiphe graminis f. sp. tritici*, (the causal agent of wheat powdery mildew) and incubated in a growth chamber at 20° C. for 7 days, after which disease ratings were made.

TEST B

The test suspension was sprayed to the point of run-off on wheat seedlings. The following day the seedlings were inoculated with a spore suspension of *Puccinia recondita* (the casual agent of wheat leaf rust) and incubated in a saturated atmosphere at 20° C. for 24 h, and then moved to a growth chamber at 20° C. for 6 days, after which disease ratings were made.

TEST C

The test suspension was sprayed to the point of run-off on rice seedlings. The following day the seedlings were inoculated with a spore suspension of *Pyricularia oryzae* (the causal agent of rice blast) and incubated in a saturated atmosphere at 27° C. for 24 h, and then moved to a growth chamber at 30° C. for 5 days, after which disease ratings were made.

TEST D

The test suspension was sprayed to the point of run-off on tomato seedlings. The following day the seedlings were inoculated with a spore suspension of *Phytophthora infestans* (the causal agent of potato and tomato late blight) and incubated in a saturated atmosphere at 20° C. for 24 h, and then moved to a growth chamber at 20° C. for 5 days, after which disease ratings were made.

TEST E

The test suspension was sprayed to the point of run-off on grape seedlings. The following day the seedlings were inoculated with a spore suspension of *Plasmopara viticola* (the causal agent of grape downy mildew) and incubated in a saturated atmosphere at 20° C. for 24 h, moved to a growth chamber at 20° C. for 6 days, and then incubated in a saturated atmosphere at 20° C. for 24 h, after which disease ratings were made.

TEST F

Tomato (or potato) seedlings are inoculated with a spore suspension of *Phytophthora infestans* (the causal agent of potato and tomato late blight) and incubated in a saturated atmosphere at 20° C. for 24 h. The next day, test suspension is sprayed to the point of run-off and the treated plants are moved to a growth chamber at 20° C. for 5 days, after which disease ratings are made.

TEST G

Grape seedlings are inoculated with a spore suspension of *Plasmopara viticola* (the causal agent of grape downy mildew) and incubated in a saturated atmosphere at 20° C. for 24 h. The next day, test suspension is sprayed to the point of run-off and the treated plants are moved to a growth chamber at 20° C. for 6 days, and then incubated in a saturated atmosphere at 20° C. for 24 h, after which disease ratings are made.

Results for Tests A–E are given in Table A. In the table, a rating of 100 indicates 100% disease control and a rating of 0 indicates no disease control (relative to the controls). A dash (–) indicates no test results. ND indicates disease control not determined due to phytotoxicity. In addition to the Tests shown below, compounds of this invention (e.g. compounds 2, 5, 8, 28, 29, 30, 31, 35, 36 and 37) are considered to have significant curative utility, especially for grape downy mildew.

TABLE A

| Cmpd No. | Test A | Test B | Test C | Test D | Test E | Test F | Test G |
|---|---|---|---|---|---|---|---|
| 1 | 0 | 0 | 0 | 90 | 29 | | |
| 2 | 0 | ND | — | 100 | — | | 99 |
| 3 | 21 | 28 | 0 | 7 | 8 | | |
| 4 | — | — | — | 99 | — | | |
| 5 | — | 19 | — | — | 98 | | 99 |
| 6 | 0 | 0 | — | 19 | — | | |
| 7 | 0 | 0 | — | — | — | | |
| 8 | 0 | 8 | — | 100 | 100 | | 96 |
| 9 | 0 | 28 | 0 | 7 | 0 | | |
| 10 | 0 | 9 | 74 | 16 | 0 | | |
| 11 | 0 | 9 | 0 | 7 | 8 | | |
| 12 | 0 | 19 | 0 | 7 | 24 | | |
| 13 | 0 | 9 | 0 | 3 | 23 | | |
| 14 | 0 | 19 | 90 | 100 | 98 | | |
| 15 | 0 | 38 | 30 | 7 | 8 | | |
| 16 | 0 | 9 | 100 | 34 | 8 | | |
| 17 | 13 | 0 | 0 | 25 | 0 | | |
| 18 | 0 | 9 | 80 | 32 | 0 | | |
| 19 | 0 | 9 | 0 | 7 | 8 | | |
| 20 | 0 | 28 | 87 | 25 | 8 | | |
| 21 | 69 | 68 | 88 | 16 | 8 | | |
| 22 | 0 | 0 | 0 | 7 | 0 | | |
| 23 | 72 | 9 | 7 | 32 | 8 | | |
| 24 | 0 | 0 | 7 | 25 | 8 | | |
| 25 | 0 | 9 | 13 | 79 | 16 | | |
| 26 | 0 | 32 | 0 | 25 | 0 | | |
| 27 | 0 | 0 | 0 | 32 | 16 | | |
| 28 | — | — | 0 | 100 | 100 | 97# | 37* |
| 29 | — | — | 0 | 100 | 100 | | 100* |
| 30 | — | — | 0 | 100 | 100 | | 100* |
| 31 | — | — | 0 | 100 | 100 | | 100** |
| 32 | 0 | 0 | 0 | 32 | — | | |
| 33 | 91 | — | — | 71 | — | | |
| 34 | 0 | 44 | — | 31 | — | | |
| 35 | 0 | 30 | — | 100 | 100 | | 100* |
| 36 | 0 | 38 | 0 | 100 | 100 | | 100 |
| 37 | 0 | 19 | 0 | 100 | 100 | | 100 |
| 38 | — | — | — | — | 69* | | 0** |

100 ppm on potato seedlings
*100 ppm
**20 ppm.

What is claimed is:

1. A fungicidal composition comprising:
   (1) at least one compound selected from Formula I and Formula II, N-oxides and agriculturally suitable salts thereof,

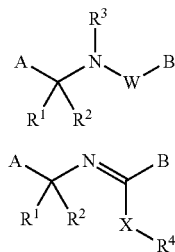

wherein:
   A is a substituted pyridinyl ring;
   B is a substituted pyridinyl ring;
   W is C=L or $SO_n$;
   L is O or S;
   $R^1$ and $R^2$ are each independently H; or $C_1$–$C_6$ alkyl, $C_2$–$C_6$ alkenyl, $C_2$–$C_6$ alkynyl or $C_3$–$C_6$ cycloalkyl, each optionally substituted;
   $R^3$ is H; or $C_1$–$C_6$ alkyl, $C_2$–$C_6$ alkenyl, $C_2$–$C_6$ alkynyl or $C_3$–$C_6$ cycloalkyl, $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl;
   $R^4$ is $C_1$–$C_6$ alkyl, $C_2$–$C_6$ alkenyl, $C_2$–$C_6$ alkynyl or $C_3$–$C_6$ cycloalkyl, each optionally substituted;
   X is O or S; and
   n is 1 or 2; provided that when W is C=O and $R^1$, $R^2$ and $R^3$ are H; then B is other than 4-trifluoromethyl-3-pyridinyl, 2-chloro-4-pyridinyl and 2,6-dihalo-4-pyridinyl; and
   (2) at least one other fungicide having a different mode of action selected from the group consisting of fungicides inhibiting mitochondrial respiration, fungicides inhibiting protein synthesis by interference of the synthesis of ribosomal RNA, and fungicides inhibiting beta-tubulin synthesis.

2. A fungicidal composition of claim 1 wherein
   A is a pyridinyl ring substituted with from 1 to 4 $R^5$;
   B is a pyridinyl ring substituted with from 1 to 4 $R^6$;
   $R^1$ and $R^2$ are each independently H; or $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino;

$R^4$ is $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino;

$R^5$ and $R^6$ are each independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or $R^5$ and $R^6$ are each independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl $C_1$–$C_4$ alkoxycarbonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

3. A fungicidal composition of claim 2 of Formula I wherein W is C=O.

4. A fungicidal composition of claim 3 wherein A is a 2-pyridinyl ring substituted with from 1 to 4 $R^5$; and B is substituted with from 1 to 4 $R^6$, with at least one $R^6$ located in a position ortho to the link with W.

5. A fungicidal composition of claim 1 comprising a component (1) compound and a fungicide selected from the group consisting of azoxystrobin, kresoxim-methyl, pyrclostrobin, trifloxystrobin, carbendazim, famoxadone, fenamidone, benomyl, cymoxanil, dimethomorph, folpet, fosetyl-aluminum, metalaxyl, mancozeb, and maneb.

6. A compound selected from Formula I and Formula II, N-oxides and agriculturally suitable salts thereof,

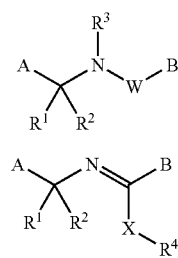

wherein:
A is a 3-pyridinyl ring substituted with from 1 to 4 $R^5$;
B is a pyridinyl ring substituted with from 1 to 4 $R^6$;
W is C=O;
$R^1$ and $R^2$ are each independently H; or $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino;

$R^3$ is H; or $C_1$–$C_6$ alkyl, $C_2$–$C_6$ alkenyl, $C_2$–$C_6$ alkynyl or $C_3$–$C_6$ cycloalkyl, $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl;

$R^4$ is $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino;

$R^5$ and $R^6$ are each independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or $R^5$ and $R^6$ are each independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl $C_1$–$C_4$ alkoxycarbonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl; and X is O or S; provided that when $R^1$, $R^2$ and $R^3$ are H; then B is other than 4-trifluoromethyl-3-pyridinyl, 2-chloro-4-pyridinyl and 2,6-dihalo-4-pyridinyl.

7. A compound selected from Formula I and Formula II, N-oxides and agriculturally suitable salts thereof,

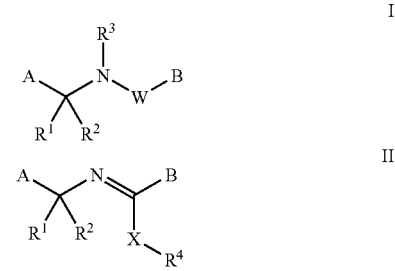

wherein:
A is a 2-pyridinyl ring substituted with from 1 to 4 $R^5$;
B is a 3-pyridinyl ring or 4-pyridinyl ring substituted with from 2 to 4 $R^6$; having an at each position ortho to the link with W and optionally 1 to 2 additional $R^6$;

W is C=O;

R¹ and R² are each independently H; or $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino;

R³ is H; or $C_1$–$C_6$ alkyl, $C_2$–$C_6$ alkenyl, $C_2$–$C_6$ alkynyl or $C_3$–$C_6$ cycloalkyl, $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl;

R⁴ is $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino;

R⁵ and R⁶ are each independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or R⁵ and R⁶ are each independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl $C_1$–$C_4$ alkoxycarbonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl; and X is O or S.

8. A compound of claim 7 wherein each R⁶ is either halogen or methyl.

9. A compound of claim 8 wherein B is a 3-pyridinyl ring wherein one R⁶ is Cl and is located at the 2-position ortho to the link with W, another R⁶ is selected from Cl or methyl and is located at the 4-position ortho to the link with W and a third optional R⁶ is methyl at the 6-position.

10. The compound of claim 9 wherein A is 3-chloro-5-$CF_3$-2-pyridinyl.

11. The compound of claim 9 selected from the group consisting of 2,4-Dichloro-N-[[3-chloro-5-(trifluoromethyl)-2-pyridinyl]methyl]-3-pyridinecarboxamide, and 2,4-Dichloro-N-[[3-chloro-5-(trifluoromethyl)-2-pyridinyl]methyl]-6-methyl-3-pyridinecarboxamide.

12. The compound of claim 8 wherein R¹ is H and R² is $CH_3$.

13. A compound selected from Formula I and Formula II, N-oxides and agriculturally suitable salts thereof,

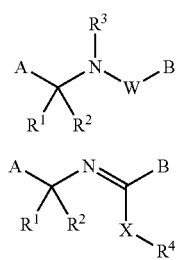

wherein:

A is a 2-pyridinyl ring substituted with from 1 to 4 R⁵;

B is a pyridinyl ring substituted with from 1 to 4 R⁶, with at least one R⁶ located in a position ortho to the link with W;

W is C=O;

R¹ is H;

R² is $CH_3$;

R³ is H; or $C_1$–$C_6$ alkyl, $C_2$–$C_6$ alkenyl, $C_2$–$C_6$ alkynyl or $C_3$–$C_6$ cycloalkyl, $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl;

R⁴ is $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino;

R⁵ and R⁶ are each independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or R⁵ and R⁶ are each independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl $C_1$–$C_4$ alkoxycarbonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl; and X is O or S.

14. The compound of claim 13 selected from the group consisting of 2,4-Dichloro-N-[1-[3-chloro-5-(trifluoromethyl)-2-pyridinyl]ethyl]-3-pyridinecarboxamide, and 2,4-Dichloro-N-[1-[3-chloro-5-(trifluoromethyl)-2-pyridinyl]ethyl]-6-methyl-3-pyridinecarboxamide.

15. A compound selected from Formula I, N-oxides and agriculturally suitable salts thereof,

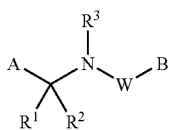

wherein:

A is a pyridinyl ring substituted with from 1 to 4 $R^5$;
B is a pyridinyl ring substituted with from 1 to 4 $R^6$;
W is C=L or $SO_n$;
L is O or S;
$R^1$ and $R^2$ are each independently H; or $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino;
$R^3$ is H; or $C_1$–$C_6$ alkyl, $C_2$–$C_6$ alkenyl, $C_2$–$C_6$ alkynyl or $C_3$–$C_6$ cycloalkyl, $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl;
$R^4$ is $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino;
each $R^5$ is independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; provided that when A is 2-pyridinyl, then $R^5$ is other than $C_1$ to $C_6$ haloalkyl; and
each $R^6$ is independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or
$R^5$ and $R^6$ are each independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl $C_1$–$C_4$ alkoxycarbonyl, $C_1$–$C_4$ alkylamino, $C_2$–$C_8$ dialkylamino, $C_3$–$C_6$ cycloalkylamino, $C_3$–$C_6$ (alkyl) cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl; and n is 1 or 2; provided that when W is C=O and $R^1$, $R^2$ and $R^3$ are H; then B is other than 4-trifluoromethyl-3-pyridinyl, 2-chloro-4-pyridinyl and 2,6-dihalo-4-pyridinyl.

16. A compound of claim 15 wherein

W is C=O; and each $R^5$ is independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; provided that when A is 2-pyridinyl, then $R^5$ is other than $C_1$ to $C_6$ haloalkyl.

17. A compound of claim 16 wherein $R^5$ is Cl, Br, $CH_3$, $OCF_3$, $OCHF_2$, $OCH_2CF_3$, $OCF_2CF_3$, $OCF_2CF_2H$, $OCHFCF_3$, $SCF_3$, $SCHF_2$, $SCH_2CF_3$, $SCF_2CF_3$, $SCF_2CF_2H$, $SCHFCF_3$, $SOCF_3$, $SOCHF_2$, $SOCH_2CF_3$, $SOCF_2CF_3$, $SOCF_2CF_2H$, $SOCHFCF_3$, $SO_2CF_3$, $SO_2CHF_2$, $SO_2CH_2CF_3$, $SO_2CF_2CF_3$, $SO_2CF_2CF_2H$ or $SO_2CHFCF_3$.

18. The compound of claim 15 selected from the group consisting of 2,4-Dichloro-N-[(3,5-dichloro-2-pyridinyl)methyl]-3-pyridinecarboxamide, 2,4-Dichloro-N-[1-(3,5-dichloro-2-pyridinyl)ethyl]-3-pyridinecarboxamide, 2,4-Dichloro-N-[(3,5-dichloro-2-pyridinyl)methyl]-6-methyl-3-pyridinecarboxamide, 2,4-Dichloro-N-[1-(3,5-dichloro-2-pyridinyl)ethyl]-6-methyl-3-pyridinecarboxamide, N-[(5-bromo-3-chloro-2-pyridinyl)methyl]-2,4-dichloro-3-pyridinecarboxamide, N-[1-(5-bromo-3-chloro-2-pyridinyl)ethyl]-2,4-dichloro-3-pyridinecarboxamide, N-[(5-bromo-3-chloro-2-pyridinyl)methyl]-2,4-dichloro-6-methyl-3-pyridinecarboxamide, and N-[1-(5-bromo-3-chloro-2-pyridinyl)ethyl]-2,4-dichloro-6-methyl-3-pyridinecarboxamide.

19. A fungicidal composition comprising a fungicidally effective amount of a compound of claim 6, claim 7, claim 13, or claim 15 and at least one additional component selected from the group consisting of surfactants, solid diluents and liquid diluents.

20. A method for controlling plant diseases caused by fungal plant pathogens comprising applying to the plant or portion thereof, or to the plant seed or seedling, a fungicidally effective amount of a compound of claim 6, claim 7, claim 13, or claim 15.

* * * * *